(12) United States Patent
Nakajima et al.

(10) Patent No.: US 7,176,208 B2
(45) Date of Patent: Feb. 13, 2007

(54) QUINOXALINYL MACROCYCLIC HEPATITIS C SERINE PROTEASE INHIBITORS

(75) Inventors: Suanne Nakajima, Cambridge, MA (US); Zhenwei Miao, Medway, MA (US); Ying Sun, Waltham, MA (US); Datong Tang, Malden, MA (US); Guoyou Xu, Auburndale, MA (US); Brian Porter, Cambridge, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 31 days.

(21) Appl. No.: 10/826,743

(22) Filed: Apr. 16, 2004

(65) Prior Publication Data

US 2004/0266668 A1 Dec. 30, 2004

Related U.S. Application Data

(60) Provisional application No. 60/509,071, filed on Apr. 18, 2003.

(51) Int. Cl.
C07D 401/12 (2006.01)
C07D 409/14 (2006.01)
A61K 31/38 (2006.01)
A61K 31/395 (2006.01)
A61P 31/12 (2006.01)

(52) U.S. Cl. .................. 514/255.05; 540/455; 540/460
(58) Field of Classification Search ............... 540/455, 540/460; 514/255.05
See application file for complete search history.

(56) References Cited

U.S. PATENT DOCUMENTS

| 6,329,379 B1 | 12/2001 | Llinas-Brunet et al. |
| 6,608,027 B1 | 8/2003 | Tsantrizos et al. |
| 2002/0037998 A1 | 3/2002 | Llinas-Brunet et al. |

FOREIGN PATENT DOCUMENTS

| WO | WO-00/09543 | 2/2000 |
| WO | WO-00/59929 | 10/2000 |
| WO | WO-2003/053349 A3 | 7/2003 |
| WO | WO-2004/072243 A2 | 8/2004 |

OTHER PUBLICATIONS

M. Llinás-Burnet, et al., "Peptide-Based Inhibitors of the Hepatitis C Virus Serine Protease," Bioorganic & Medicinal Chemistry Letters 8, (1998), pp. 1713-1718.
A. Spatola, "Peptide Backbone Modifications: A Structure-Activity Analysis of Peptides Containing Amide Bond Surrogates, Conformational Constraints, and Rela, " Department of Chemistry, University of Louisville, Louisville Kentucky, pp. 267-357, XP 002032461.

*Primary Examiner*—Bruck Kifle
(74) *Attorney, Agent, or Firm*—Edwards Angell Palmer & Dodge LLP; Jeffrey D. Hsi

(57) ABSTRACT

The present invention relates to compounds of Formula I or II, or a pharmaceutically acceptable salt, ester, or prodrug, thereof:

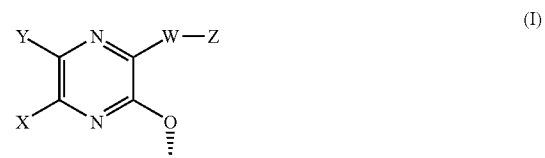

OR

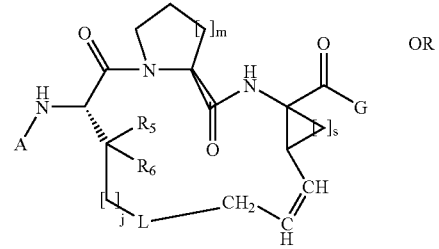

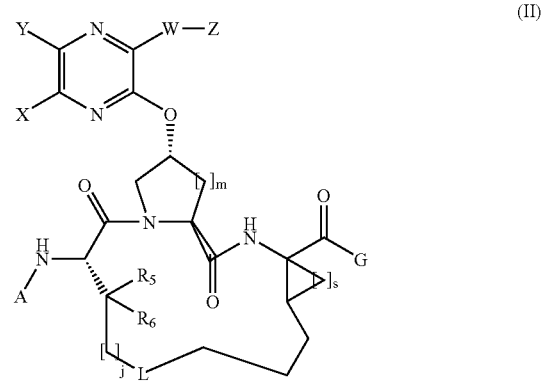

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

10 Claims, No Drawings

QUINOXALINYL MACROCYCLIC HEPATITIS C SERINE PROTEASE INHIBITORS

CROSS-REFERENCE TO RELATED APPLICATIONS

This applications claims benefit of U.S. provisional application 60/509,071 (conversion of U.S. Ser. No. 10/418,759) filed Apr. 18, 2003, the entire contents of which is herein incorporated by reference.

TECHNICAL FIELD

The present invention relates to novel macrocycles having activity against the hepatitis C virus (HCV) and useful in the treatment of HCV infections. More particularly, the invention relates to macrocyclic compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3–12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug would desirably possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3.4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, *Nature Rev. Drug Discov.*, 1, 867–881 (2002). Other patent disclosures describing the synthesis of HCV protease inhibitors are: WO 00/59929 (2000); WO 99/07733 (1999); WO 00/09543 (2000); WO 99/50230 (1999); U.S. Pat. No. 5,861,297 (1999); and US2002/0037998 (2002).

SUMMARY OF THE INVENTION

The present invention relates to novel macrocyclic compounds and methods of treating a hepatitis C infection in a subject in need of such therapy with said macrocyclic compounds. The present invention further relates to pharmaceutical compositions comprising the compounds of the present invention, or pharmaceutically acceptable salts, esters, or prodrugs thereof, in combination with a pharmaceutically acceptable carrier or excipient.

In one embodiment of the present invention there are disclosed compounds represented by Formulas I and II, or pharmaceutically acceptable salts, esters, or prodrugs thereof:

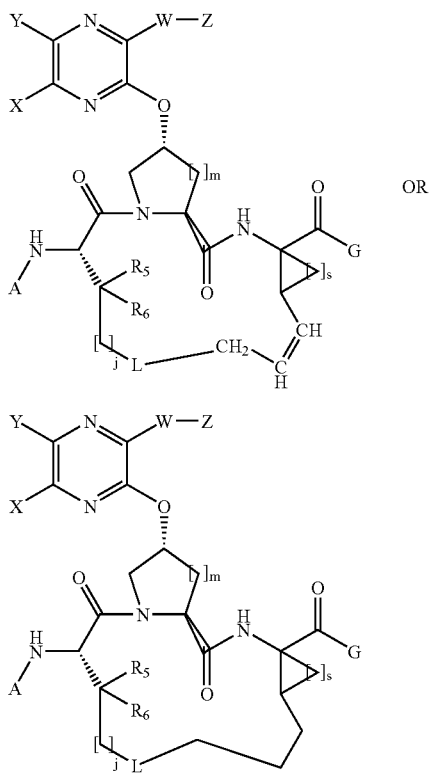

Wherein

A is independently selected from hydrogen; —(C=O)—O—R₁, —(C=O)—R₂, —C(=O)—NH—R₂, —C(=S)—NH—R₂, or —S(O)₂—R₂;

G is independently selected from —OH, —O—(C₁–C₁₂ alkyl), —NHS(O)₂—R₁, —(C=O)—R₂, —(C=O)—O—R₁, or —(C=O)—NH—R₂;

L is independently selected from —S—, —SCH₂—, —SCH₂CH₂—, —S(O)₂—, —S(O)₂CH₂CH₂—, —S(O)—, —S(O)CH₂CH₂—, —O—, —OCH₂—, —OCH₂CH₂—, —(C=O)—CH₂—, —CH(CH₃)CH₂—, —CFHCH₂—, or —CF₂CH₂—;

X and Y taken together with the carbon atoms to which they are attached form a cyclic moiety selected from aryl, substituted aryl, heteroaryl, or substituted heteroaryl;

W is absent, or independently selected from —O—, —S—, —NH—, —C(O)NR₁— or —NR₁—;

Z is independently selected from hydrogen, —CN, —SCN, —NCO, —NCS, —NHNH₂, —N₃, halogen, —R₄, —C₃–C₁₂ cycloalkyl, substituted —C₃–C₁₂ cycloalkyl, aryl, substituted aryl, heteroaryl, substituted heteroaryl, heterocycloalkyl, substituted heterocycloalkyl, or —NH—N=CH (R₁);

Each R₁ is independently selected from hydrogen, C₁–C₆ alkyl, substituted C₁–C₆ alkyl, C₁–C₆ alkenyl, substituted C₁–C₆ alkenyl, C₁–C₆ alkynyl, substituted C₁–C₆ alkynyl, C₃–C₁₂ cycloalkyl, substituted C₃–C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;

Each R₂ is independently selected from hydrogen, C₁–C₆ alkyl, C₁–C₆ alkyl, substituted C₁–C₆ alkyl, C₁–C₆ alkenyl, substituted C₁–C₆ alkenyl, C₁–C₆ alkynyl, substituted C₁–C₆ alkynyl, C₃–C₁₂ cycloalkyl, substituted C₃–C₁₂ cycloalkyl, alkylamino, dialkylamino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;

Each R₄ is independently selected from:
(i) —C₁–C₆ alkyl containing 0, 1, 2, or 3 heteroatoms selected from O, S, or N, optionally substituted with one or more substituent selected from halogen, aryl, substituted aryl, heteroaryl, or substituted heteroaryl,
(ii) —C₂–C₆ alkenyl containing 0, 1, 2, or 3 heteroatoms selected from O, S, or N, optionally substituted with one or more substituent selected from halogen, aryl, substituted aryl, heteroaryl, or substituted heteroaryl;
(iii) —C₂–C₆ alkynyl containing 0, 1, 2, or 3 heteroatoms selected from O, S, or N, optionally substituted with one or more substituent selected from halogen, aryl, substituted aryl, heteroaryl, or substituted heteroaryl;

R₅ and R₆ are each independently selected from hydrogen or methyl;

j=0, 1, 2, 3, or 4;

m=0, 1, or 2; and s=0, 1 or 2.

DETAILED DESCRIPTION OF THE INVENTION

A first embodiment of the invention is a compound represented by Formula I as described above, or a pharmaceutically acceptable salt, ester or prodrug thereof, alone or in combination with a pharmaceutically acceptable carrier or excipient.

A second embodiment of the invention is a compound represented by Formula II as described above, or a pharmaceutically acceptable salt, ester or prodrug thereof, alone or in combination with a pharmaceutically acceptable carrier or excipient.

Representative subgenera of the invention include, but are not limited to:

A compound of Formula III:

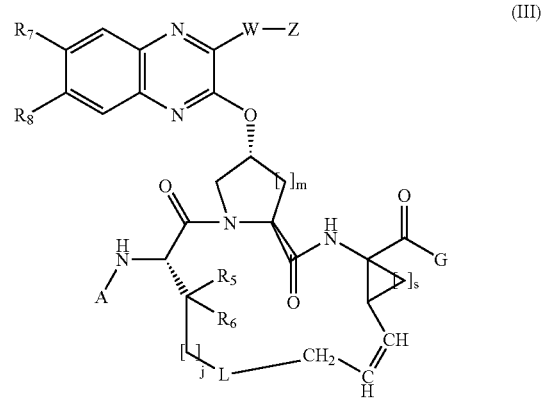

wherein R₇ and R₈ are independently selected from R₄; and

A compound of Formula IV:

$$\text{(IV)}$$

wherein $R_7$ and $R_8$ are independently selected from $R_4$;

A compound of Formula I, II, III, or IV wherein W is absent and Z is thiophenyl;

A compound of Formula I, II, III or IV wherein W is —CH═CH— and Z is thiophenyl;

A compound of Formula I, III, or IV wherein L is absent, $R_5$ and $R_6$ are hydrogen, j=3, m=1, and s=1;

Representative compounds of the invention include, but are not limited to, the following compounds:

- Compound of Formula I, wherein A=tBOC, G=OH, L=absent, X and Y taken together with the carbon atoms to which they are attached are phenyl, W is absent, Z=thiophen-2-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=2-(formamido)-thiazol-4-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=ethyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=phenyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=4-methoxyphenyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=4-ethoxyphenyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=5-bromothiophen-2-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=2-pyrid-3-yl ethylenyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=3,4-Dimethoxy-phenyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=2-thiophen-2-yl ethylenyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, Z=indole-2-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=1H-indol-3-yl methyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=furan-2-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=1H-benzoimidazol-2-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=1H-imidazol-2-ylmethyl, j=3, m=s=1, and $R_5$=$R_6$=hydrogen;
- Compound of Formula I, wherein A=tBOC, G=OEt, L=absent, X and Y taken together with the carbon atoms to which they are attached are phenyl, W is absent, Z=chloro, j=3, m=s=1, and $R_5$=$R_6$=hydrogen;
- Compound of Formula I, wherein A=tBOC, G=OH, L=absent, X and Y taken together with the carbon atoms to which they are attached are phenyl, Z=thiophen-3-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=2-pyrid-3-yl acetylenyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W is absent, Z=2,3-dihydrobenzofuran-5-yl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W=—NH—, Z=propargyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W=—N(ethyl)-, Z=benzyl, j=3, m=s=1, and $R_5$=$R_6$=hydrogen;
- Compound of Formula I, wherein A=tBOC, G=OH, L=absent, X and Y taken together with the carbon atoms to which they are attached are phenyl, W=—NH—, Z=pyrid-3-yl, j=3, m=s=1, and $R_5$=$R_6$=hydrogen;

Compound of Formula I, wherein A=tBOC, G=OH, L=absent, X and Y taken together with the carbon atoms to which they are attached are phenyl, W is absent, Z=tetrazolyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=morpholino, j=3, m=s=1, and $R_5=R_6$=hydrogen;

Compound of Formula I, wherein A=tBOC, G=OH, L=absent, X and Y taken together with the carbon atoms to which they are attached are phenyl, W=—O—, Z=thiophen-3-yl-methyl, j=3, m=s=1, and $R_5=R_6$=hydrogen;

Compound of Formula I, wherein A=tBOC, G=OH, L=absent, X and Y taken together with the carbon atoms to which they are attached are

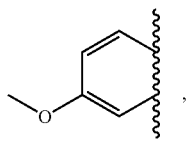
,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

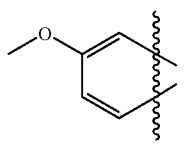
,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

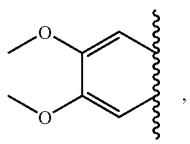
,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

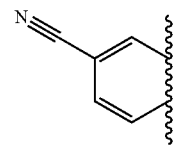
,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

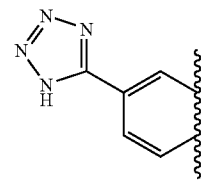
,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

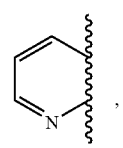
,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

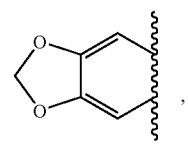
,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

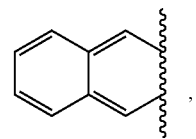
,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: methylsulfonyl-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: HO-sulfonyl-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: HO-CH$_2$-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: piperidinyl-CH$_2$-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: nitro-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: H$_2$N-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: phenyl-CH$_2$-C(=O)-NH-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: dimethylamino-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

[structure: HO-phenyl]

,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

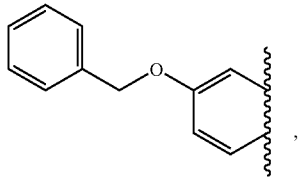,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

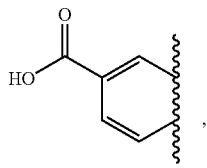,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

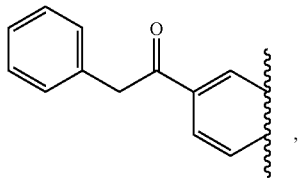,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

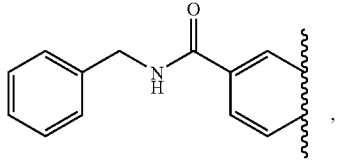,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

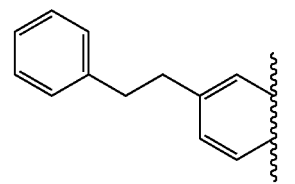,

W is absent, Z=thiophen-2-yl, j=3, m=s=1, and $R_5=R_6$=hydrogen;

Compound of Formula I, wherein A=tBOC, G=OEt, L=absent, X and Y taken together with the carbon atoms to which they are attached are

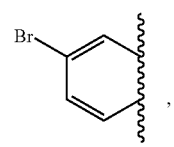,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

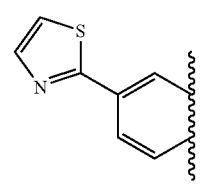,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

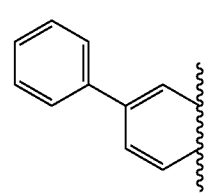,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

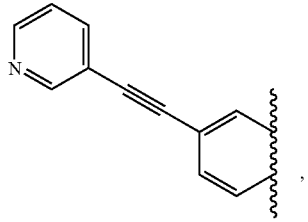

W is absent, Z=thiophen-2-yl, j=3, m=s=1, $R_5=R_6$=hydrogen;

Compound of Formula I, wherein A=tBOC, G=OH, L=absent, X and Y taken together with the carbon atoms to which they are attached are

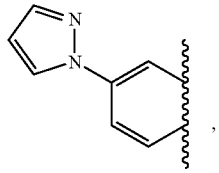

W is absent, Z=thiophen-2-yl, j=3, m=s=1, $R_5=R_6$=hydrogen;

Compound of Formula I, wherein A=—(C=O)—O—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, wherein $R^1$=cyclobutyl, G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, wherein $R^1$=cyclohexyl, G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, wherein $R^1$=

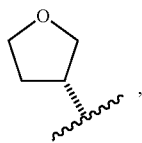

G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, wherein $R^1$=

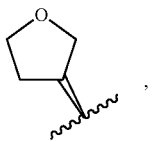

G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, wherein $R^1$=

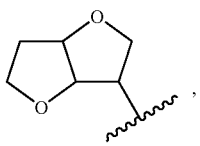

G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—NH—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5$=R=hydrogen;

Compound of Formula I, wherein A=—(C=S)—NH—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5=R_6$ hydrogen;

Compound of Formula I, wherein A=—S(O)$_2$—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, $R^1$=cyclopentyl, G=—O-phenethyl, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, $R^1$=cyclopentyl, G=—NH-phenethyl, L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—$R^1$, $R^1$=cyclopentyl, G=—NHS(O)$_2$-phenethyl L=absent, X and Y taken together with the carbon atoms to which they are attached are phenyl, W is absent, Z=thiophen-2-yl, j=3, m=s=1, and $R_5=R_6$=hydrogen;

Compound of Formula I, wherein A=—(C=O)—O—R$^1$, R$^1$=cyclopentyl, G=—(C=O)—OH, L=absent, X and Y taken together with the carbon atoms to which they are attached are phenyl, W is absent, Z=thiophen-2-yl, j=3, m=s=1, and R$_5$=R$_6$=hydrogen;

Compound of Formula I, wherein A=—(C=O)—O—R$^1$, R$^1$=cyclopentyl, G=—(C=O)—O-phenethyl, L=absent, X and Y taken together with the carbon atoms to which they are attached are phenyl, W is absent, Z=thiophen-2-yl, j=3, m=s=1, and R$_5$=R$_6$=hydrogen;

Compound of Formula I, wherein A=—(C=O)—O—R$^1$, R$^1$=cyclopentyl, G=—(C=O)—NH-phenethyl, L=absent, X and Y taken together with the carbon atoms to which they are attached are phenyl, W is absent, Z=thiophen-2-yl, j=3, m=s=1, and R$_5$=R$_6$=hydrogen;

Compound of Formula I, wherein A=—(C=O)—O—R$^1$, R$^1$=cyclopentyl, G=—(C=O)—NH—S(O)$_2$-benzyl, L=absent, X and Y taken together with the carbon atoms to which they are attached are phenyl, W is absent, Z=thiophen-2-yl, j=3, m=s=1, and R$_5$=R$_6$=hydrogen;

Compound of Formula I, wherein A=tBOC, G=OH, L=—(C=O)CH$_2$—, X and Y taken together with the carbon atoms to which they are attached are phenyl, W is absent, Z=thiophen-2-yl, j=3, m=s=1, and R$_5$=R$_6$=hydrogen;

Compound of Formula I, wherein A=tBOC, G=OH, L=—CH(CH$_3$)CH$_2$—, X and Y taken together with the carbon atoms to which they are attached are phenyl, W is absent, Z=thiophen-2-yl, j=3, m=s=1, and R$_5$=R$_6$=hydrogen;

Compound of Formula I, wherein A=tBOC, G=OH, L=—O—, X and Y taken together with the carbon atoms to which they are attached are phenyl, W is absent, Z=thiophen-2-yl, j=3, m=s=1, R$_5$=methyl, and R$_6$=hydrogen;

Compound of Formula I, wherein A=tBOC, G=OH, L=—S—, X and Y taken together with the carbon atoms to which they are attached are phenyl, W is absent, Z=thiophen-2-yl, j=3, m=s=1, R$_5$=methyl, and R$_6$=hydrogen;

Compound of Formula I, wherein A=tBOC, G=OH, L=—S(O)—, X and Y taken together with the carbon atoms to which they are attached are phenyl, W is absent, Z=thiophen-2-yl, j=3, m=s=1, R$_5$=methyl, and R$_6$=hydrogen;

Compound of Formula I, wherein A=tBOC, G=OH, L=—S(O)$_2$, X and Y taken together with the carbon atoms to which they are attached are phenyl, W is absent, Z=thiophen-2-yl, j=3, m=s=1, R$_5$=methyl, and R$_6$=hydrogen;

Compound of Formula I, wherein A=tBOC, G=OH, L=—SCH$_2$CH$_2$—, X and Y taken together with the carbon atoms to which they are attached are phenyl, W is absent, Z=thiophen-2-yl, j=3, m=s=1, R$_5$=methyl, and R$_6$=hydrogen;

Compound of Formula I, wherein A=tBOC, G=OH, L=CF$_2$CH$_2$, X and Y taken together with the carbon atoms to which they are attached are phenyl, W is absent, Z=thiophen-2-yl, j=3, m=s=1, and R$_5$=R$_6$=hydrogen;

Compound of Formula I, wherein A=tBOC, G=OH, L=—CHFCH$_2$—, X and Y taken together with the carbon atoms to which they are attached are phenyl, W is absent, Z=thiophen-2-yl, j=3, m=s=1, and R$_5$=R$_6$=hydrogen; and Compound of Formula II, wherein A=tBOC, G=OH, L=absent, X and Y taken together with the carbon atoms to which they are attached are phenyl, W is absent, Z=thiophen-2-yl, j=3, m=s=1, and R$_5$=R$_6$=hydrogen.

Additional compounds of the invention are those of Formula V:

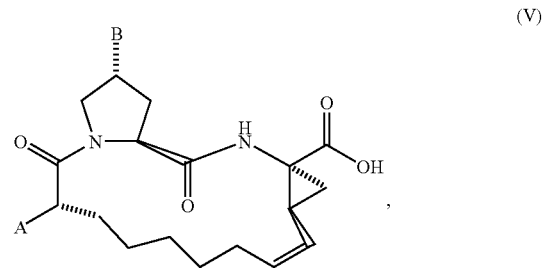

(V)

wherein A and B are as defined in the A-Matrix and B-Matrix tables herein. The A-Matrix and B-Matrix tables below set forth substituents present on the core ring structure shown in formula (V) which when one A substituent is selected from the A-Matrix and one B substituent is selected from the B-Matrix an additional compound of the invention is described. Compounds are formed by selecting any element from the A-Matrix with any element from the B-matrix to arrive upon an A, B-substituted macrocycle of formula V. For example, a compound of Formula V, wherein A is element 101 from the A-Matrix and B is element 301 from the B-Matrix, is designated by the number 101301.

Thus, the invention includes compounds of the formula V and the pharmaceutically acceptable salts thereof, wherein A is any element in the A-Matrix and B is any element of the B-Matrix.

Specific compounds include, but are not limited to, the following: 101301; 101358; 101306; 101302; 101322; 101311; 101325; 101303; 103304; 101326; 101327; 101330; 101331; 101332; 101335; 101336; 101348; 101340; 101334; 101348; 101359; 101328; 101360; 101361; 101362; 101329; 105301; 123301; 112301; 124301; 109301; 122301; 111301; 114301; 107301; 104301; 101324; 101304; 101355; 101356; 101307; 101357; 101347; 101352; 110301; 101364; 101308; 101309; 128301; 124301; 113301; 143301; 115301; 101367; 101368; 101323; 101317; 108301; 101318; 101319; 101351; 101353; 101349; 118301; 120301; 101333; 101320; 101321; 129301; 121301; 117301; 123352; 101347; 101350; 107365; 101313; 145301; 101366; 101354; 101343; 101314; 101339; 101341; 107341; 114341; 106301; 144301; 126301; 127301; 130301; 116301; 102301; 140301; 141301; 139301; 138301; 142301; 137301; 135301; 134301; 133301; 131301; 132301; 136301; 101345; 101344; 101342; 105316; 107316; 101315; 101346; 101337; 116365; and 101338.

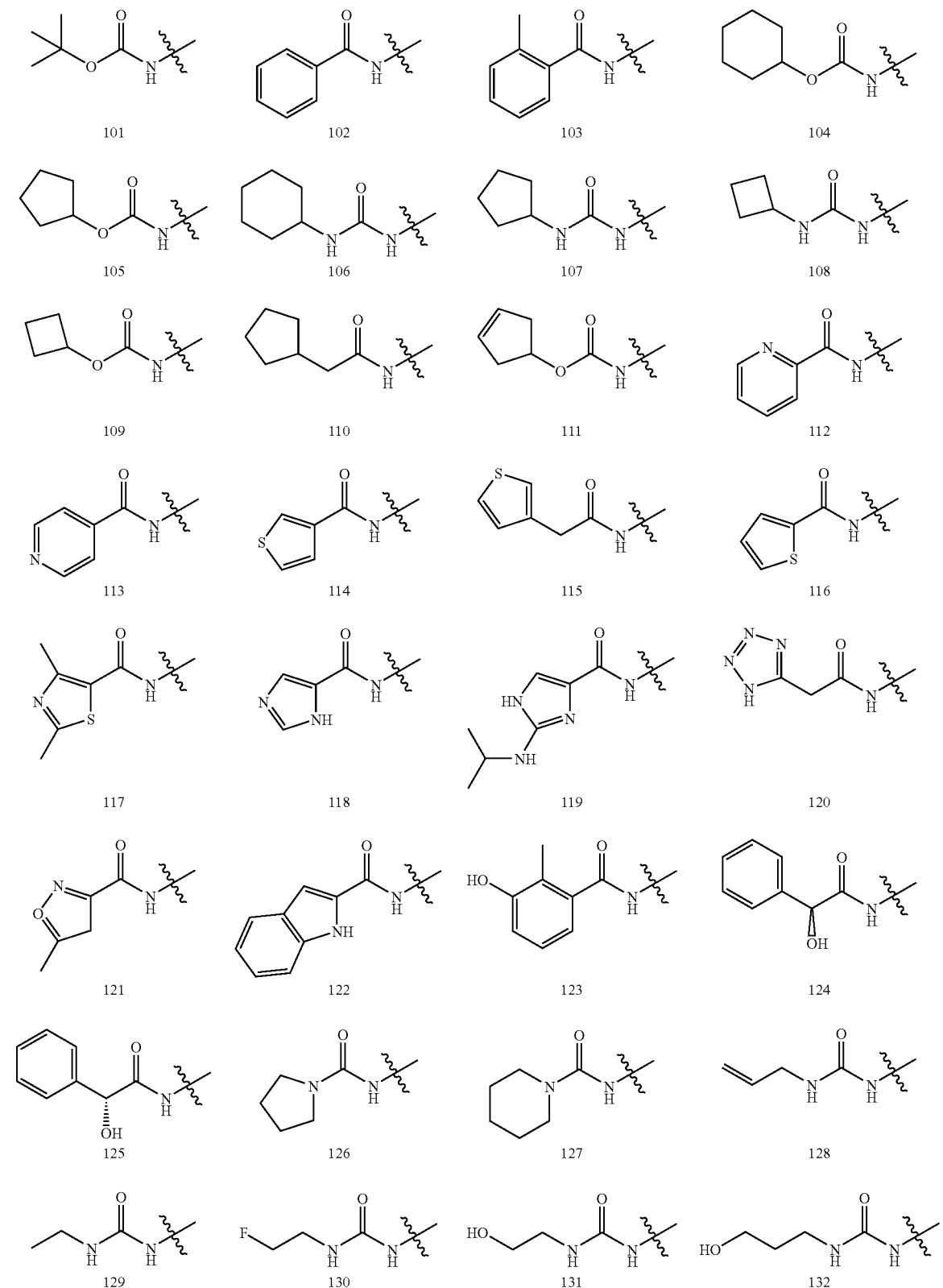

-continued
A-Matrix
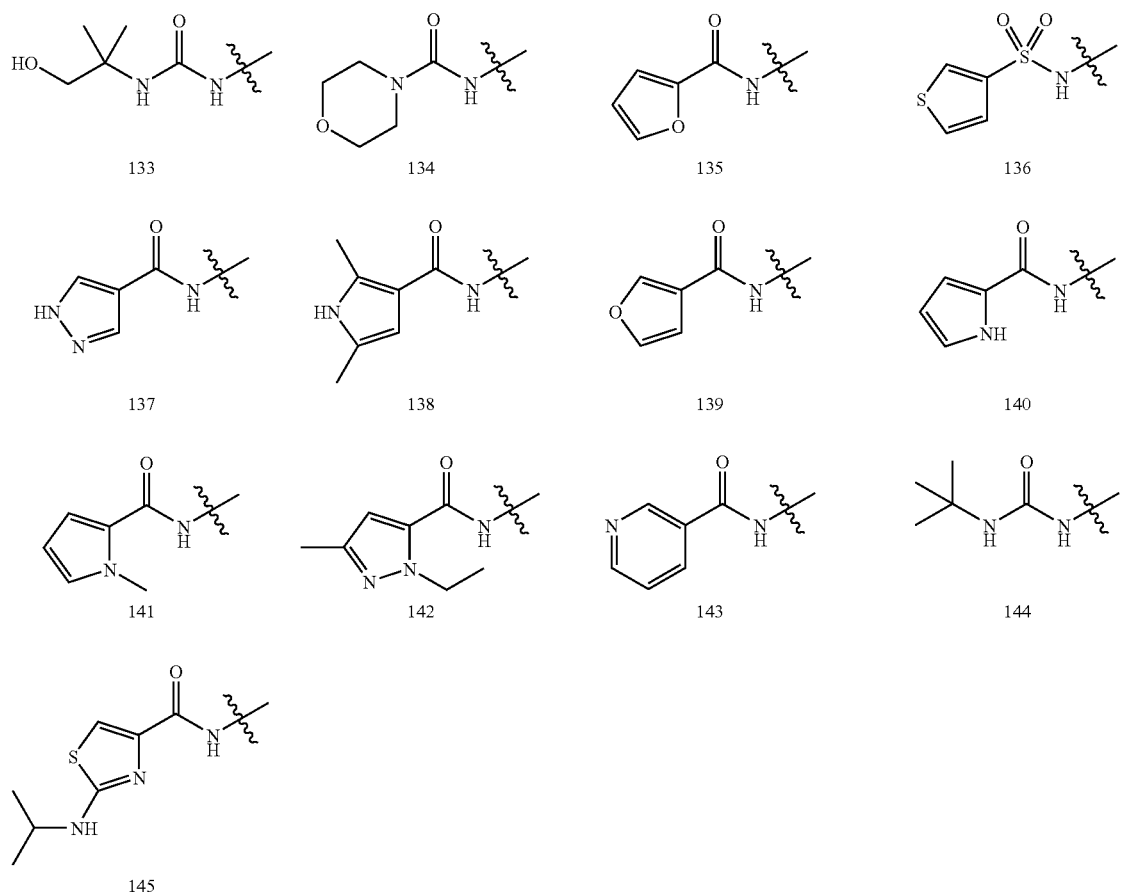
B-Matrix
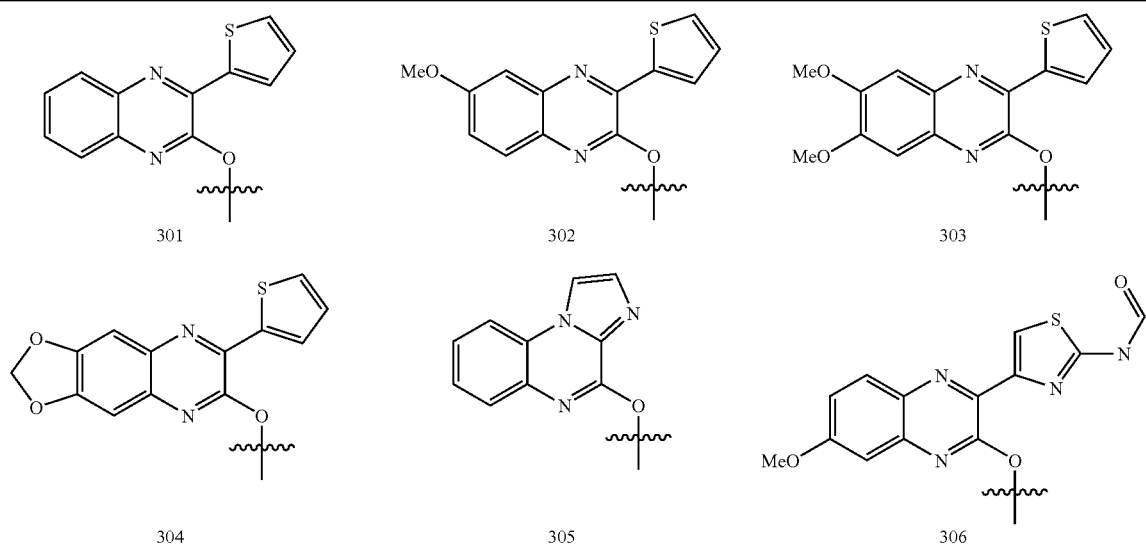

-continued
B-Matrix
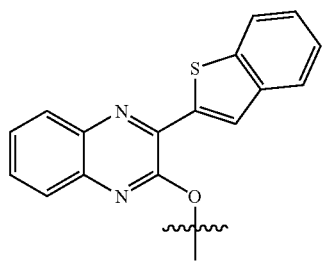
307
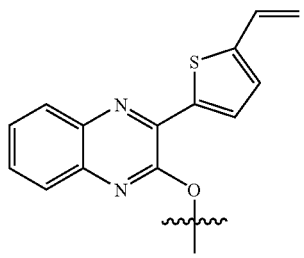
308
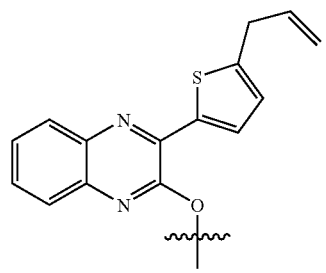
309
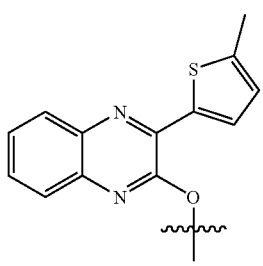
310
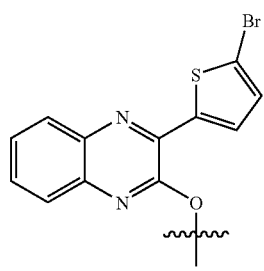
311
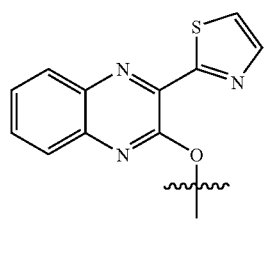
312
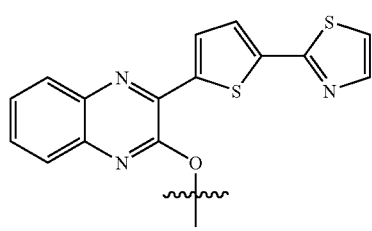
313
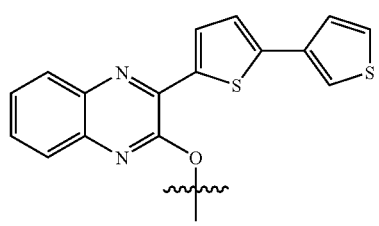
314
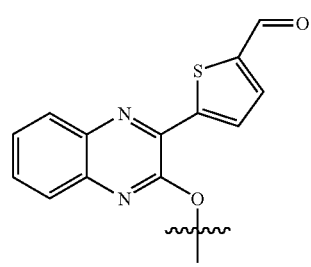
315
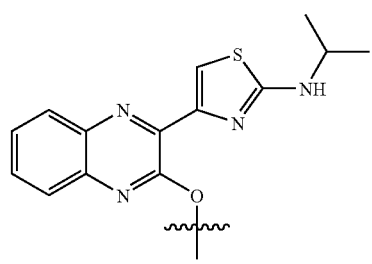
316
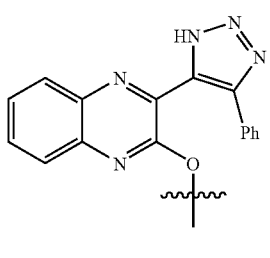
317
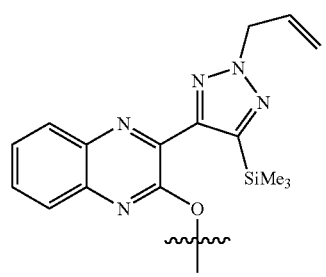
318
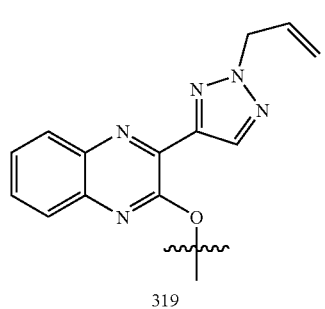
319
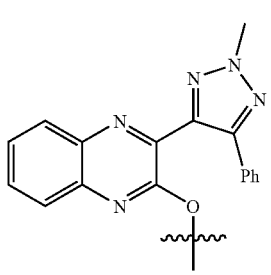
320
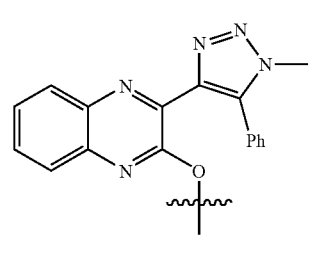
321

-continued
B-Matrix
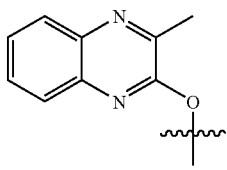
322
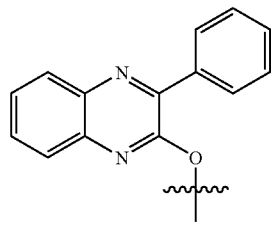
323
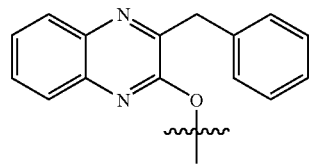
324
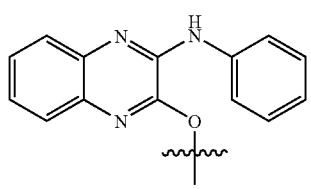
325
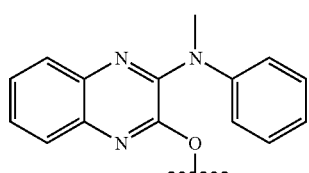
326
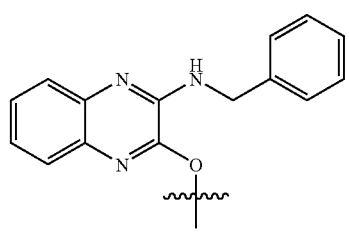
327
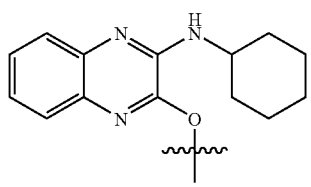
328
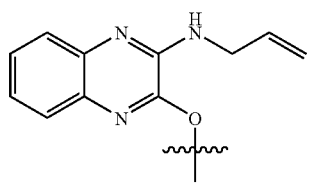
329
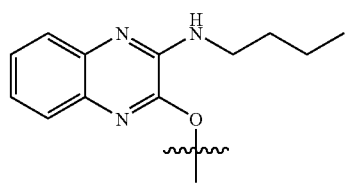
330
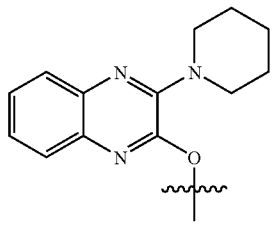
331
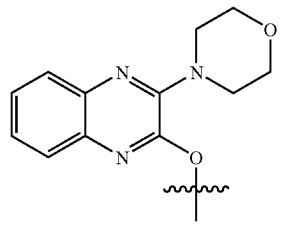
332
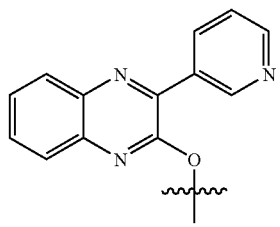
333
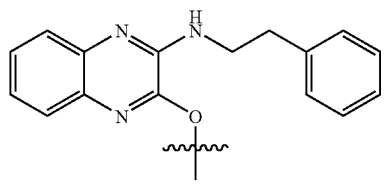
334
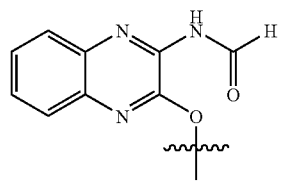
335
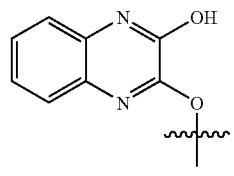
336
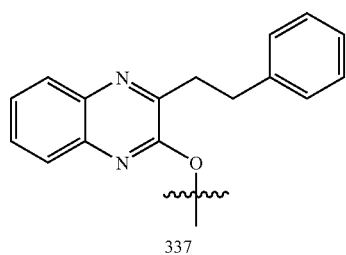
337
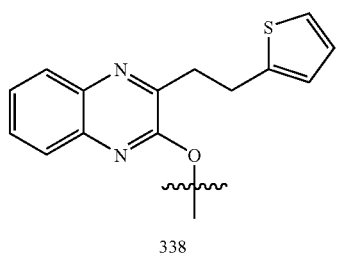
338
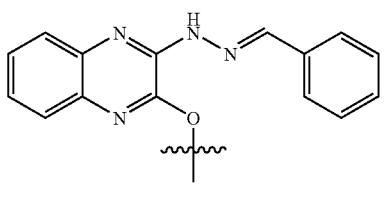
339

-continued
B-Matrix
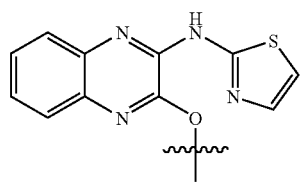
340
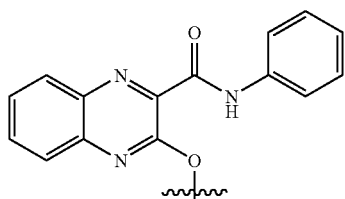
341
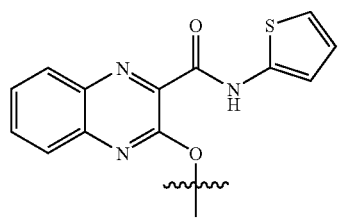
342
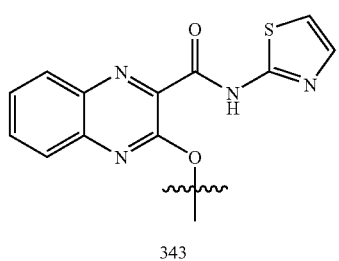
343
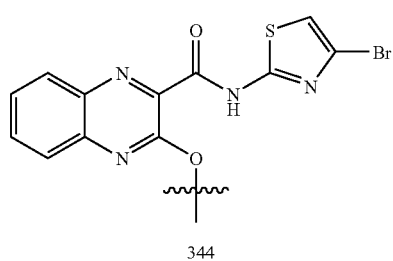
344
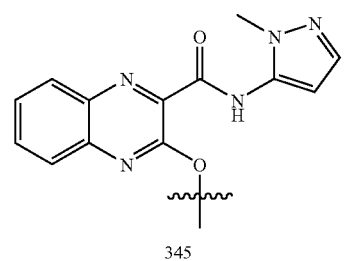
345
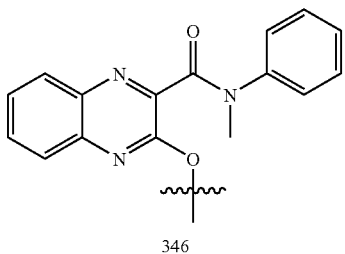
346
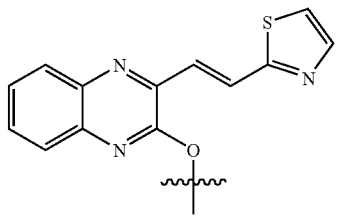
347
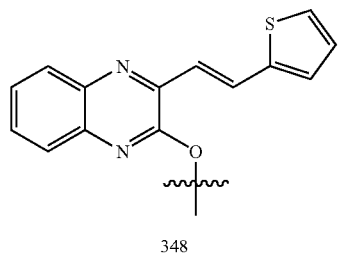
348
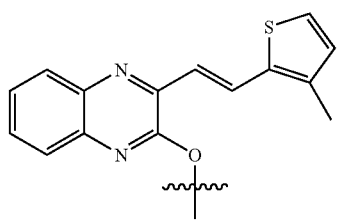
349
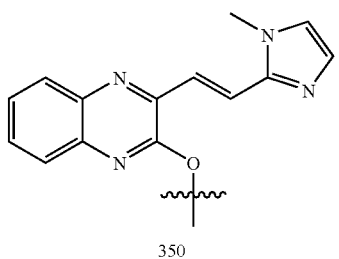
350
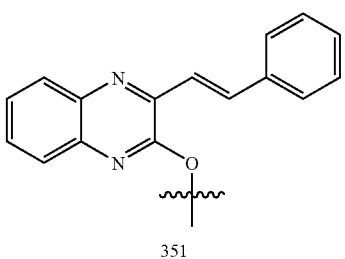
351
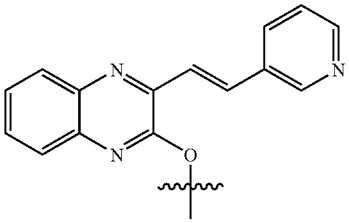
352
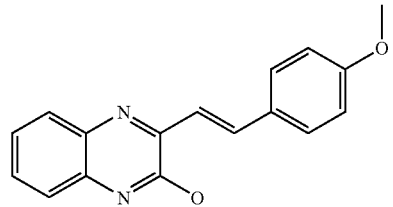
353
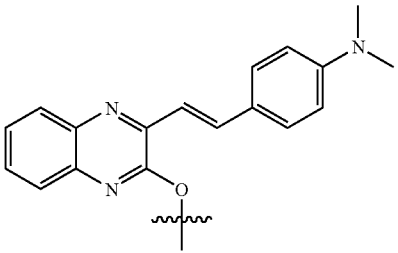
354

-continued
B-Matrix
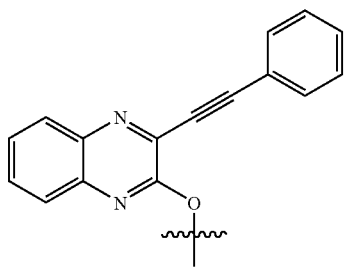
355
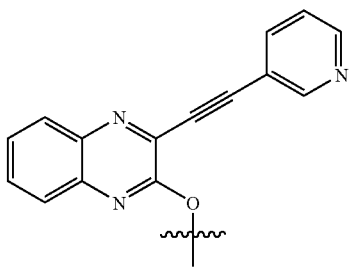
356
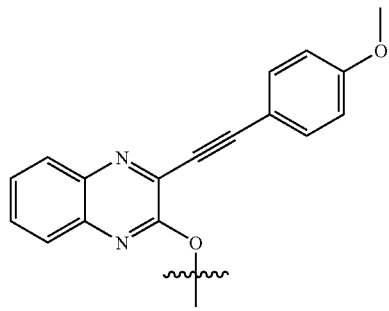
357
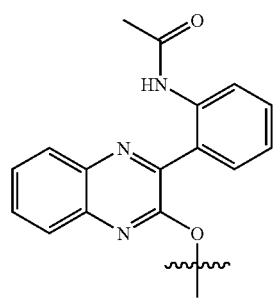
358
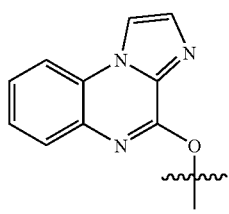
359
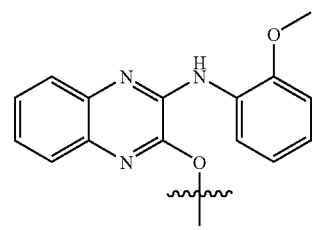
360
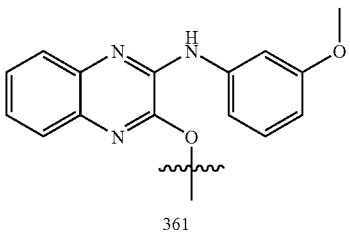
361
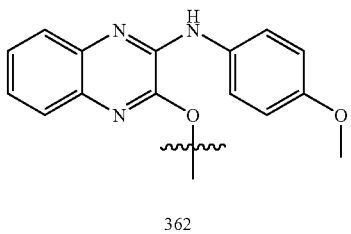
362
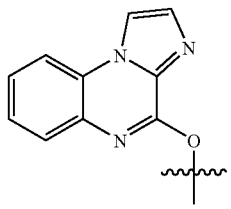
363
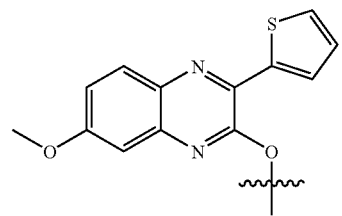
364
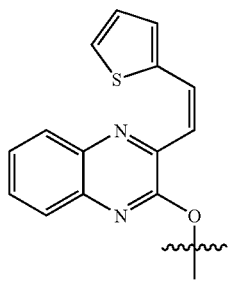
365
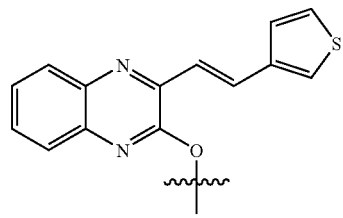
366
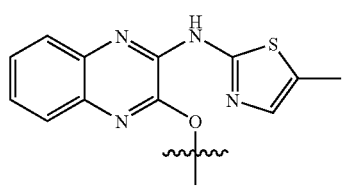
367
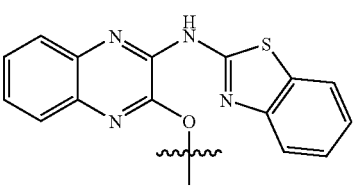
368

According to an alternate embodiment, the pharmaceutical compositions of the present invention may further contain other anti-HCV agents. Examples of anti-HCV agents include, but are not limited to, α-interferon, β-interferon, ribavirin, and amantadine. For further details see S. Tan, A. Pause, Y. Shi, N. Sonenberg, Hepatitis C Therapeutics: Current Status and Emerging Strategies, *Nature Rev. Drug Discov.*, 1, 867–881 (2002); WO 00/59929 (2000); WO 99/07733 (1999); WO 00/09543 (2000); WO 99/50230 (1999); U.S. Pat. No. 5,861,297 (1999); and US2002/0037998 (2002) which are herein incorporated by reference in their entirety.

According to an additional embodiment, the pharmaceutical compositions of the present invention may further contain other HCV protease inhibitors.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to a further embodiment, the present invention includes methods of treating hepatitis C infections in a subject in need of such treatment by administering to said subject an anti-HCV virally effective amount or an inhibitory amount of the pharmaceutical compositions of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The terms "$C_1$–$C_3$ alkyl," "$C_1$–$C_6$ alkyl" or "$C_1$–$C_{12}$ alkyl," as used herein, refer to saturated, straight- or branched-chain hydrocarbon radicals containing between one and three, one and twelve, or one and six carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, neopentyl and n-hexyl radicals; and examples of $C_1$–$C_{12}$ alkyl radicals include, but are not limited to, ethyl, propyl, isopropyl, n-hexyl, octyl, decyl, dodecyl radicals.

The term "substituted alkyl," as used herein, refers to a "$C_2$–$C_{12}$ alkyl" or "$C_1$–$C_6$ alkyl" group substituted by independent replacement of one, two or three of the hydrogen atoms thereon with F, Cl, Br, I, OH, $NO_2$, CN, $C_1$–$C_6$-alkyl-OH, C(O)—$C_1$–$C_6$-alkyl, C(O)H, $OCH_2$—$C_3$–$C_{12}$-cycloalkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The terms "$C_2$–$C_{12}$ alkenyl" or "$C_2$–$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "substituted alkenyl," as used herein, refers to a "$C_2$–$C_{12}$ alkenyl" or "$C_1$–$C_6$ alkenyl" group substituted by independent replacement of one, two or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The terms "$C_1$–$C_{12}$ alkynyl" or "$C_1$–$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$–$C_{12}$ alkynyl" or "$C_1$–$C_6$ alkynyl" group substituted by independent replacement of one, two or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as defined herein, substituted by independent replacement of one, two or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$ alkyl, $SO_2NH$-aryl, $S_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The term "arylalkyl," as used herein, refers to a $C_1$–$C_3$ alkyl or $C_1$–$C_6$ alkyl residue attached to an aryl ring. Examples include, but are not limited to, benzyl, phenethyl and the like.

The term "substituted arylalkyl," as used herein, refers to an arylalkyl group, as previously defined, substituted by independent replacement of one, two or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, NHC(O)H, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "substituted heteroaryl," as used herein, refers to a heteroaryl group as defined herein, substituted by independent replacement of one, two or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The term "$C_3$–$C_{12}$-cycloalkyl" denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl.

The term "substituted $C_3$–$C_{12}$-cycloalkyl," as used herein, refers to a $C_3$–$C_{12}$-cycloalkyl group as defined herein, substituted by independent replacement of one, two or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement or one, two, or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

The term "heteroarylalkyl," as used herein, refers to a $C_1$–$C_3$ alkyl or $C_1$–$C_6$ alkyl residue residue attached to a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement or one, two, or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

It shall be understood that any substituted group defined above (e.g. substituted $C_1$–$C_6$ alkyl, substituted $C_1$–$C_6$ alkenyl, substituted $C_1$–$C_6$ alkynyl, substituted $C_3$–$C_{12}$ cycloalkyl, substituted aryl, substituted arylalkyl, substituted heteroaryl, substituted heteroarylalkyl, or substituted heterocycloalkyl) may also be substituted with the following suitable substituents: —F, —Cl, —Br, —I, —OH, protected hydroxy, aliphatic ethers, aromatic ethers, oxo, —$NO_2$, —CN, —$C_1$–$C_{12}$-alkyl optionally substituted with halogen (such as perhaloalkyls), $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkynyl, —O—$C_3$–$C_{12}$-cycloalkyl, —O-aryl, —O-heteroaryl, —O-heterocycloalkyl, —C(O)H, —C(O)—$C_1$–$C_{12}$-alkyl, —C(O)—$C_2$–$C_{12}$-alkenyl, —C(O)—$C_2$–$C_{12}$-alkynyl, —C(O)—$C_3$–$C_{12}$-cycloalkyl, —C(O)-aryl, C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkynyl, —CONH—$C_3$–$C_{12}$-cycloalkyl, —CONH-aryl, —CONH-heteroaryl, —CONH-heterocycloalkyl, —$CO_2$—$C_1$–$C_{12}$-alkyl, —$CO_2$—$C_2$–$C_{12}$-alkenyl, —$CO_2$—$C_2$–$C_{12}$-alkynyl, —$CO_2$—$C_3$–$C_{12}$ cycloalkyl, —$CO_2$-aryl, —$CO_2$-heteroaryl, —$CO_2$-heterocycloalkyl, —$CO_2$—$C_1$–$C_{12}$-alkyl, —$OCO_2$—$C_2$–$C_{12}$-alkenyl, —$OCO_2$—$C_2$–$C_{12}$-alkynyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkynyl, —OCONH—$C_3$–$C_{12}$-cycloalkyl, —OCONH-aryl, —OCONH-heteroaryl, —OCONH-heterocycloalkyl, —NHC(O)H, —NHC(O)—$C_1$–$C_{12}$-alkyl, —NHC(O)—$C_2$–$C_{12}$-alkenyl, —NHC(O)—$C_2$–$C_{12}$-alkynyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkynyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$–$C_{12}$-alkyl, —NHC(O)NH—$C_2$–$C_{12}$-alkenyl, —NHC(O)NH—$C_2$–$C_{12}$-alkynyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$–$C_{12}$-alkyl, —NHC(S)NH—$C_2$–$C_2$-alkenyl, —NHC(S)NH—$C_2$–$C_{12}$-alkynyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$–$C_{12}$-alkyl, —NHC(NH)NH—$C_2$–$C_{12}$-alkenyl, —NHC(NH)NH—$C_2$–$C_{12}$-alkynyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, —NHC(NH)—$C_1$–$C_{12}$-alkyl, —NHC(NH)—$C_2$–$C_{12}$-alkenyl, —NHC(NH)—$C_2$–$C_{12}$-alkynyl, —NHC(NH)—$C_3$–$C_{12}$-cycloalkyl, —NHC(NH)-aryl, —NHC(NH)-heteroaryl, —NHC(NH)-heterocycloalkyl, —(NH)NH—$C_1$–$C_{12}$-alkyl, —C(NH)NH—$C_2$–$C_{12}$-alkenyl, —(NH)NH—$C_2$–$C_{12}$-alkynyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkynyl, —S(O)—$C_3$–$C_{12}$-cycloalkyl, —S(O)-aryl, —S(O)-heteroaryl, —S(O)-heterocycloalkyl, —$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkynyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkynyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, polyalkoxyalkyl, polyalkoxy, methoxymethoxy, methoxyethoxy, —SH, —S—$C_1$–$C_2$-alkyl, —S—$C_2$–$C_{12}$-alkenyl, —S—$C_2$–$C_{12}$-alkynyl, —S—$C_3$–$C_{12}$-cycloalkyl, —S-aryl, —S-heteroaryl, —S-heterocycloalkyl, or methylthiomethyl. It is understood that the aryls, heteroaryls, alkyls and the like can be further substituted.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl)$_2$ where $C_1$–$C_{12}$ alkyl is as previously defined. Examples of dialkylamino are, but not limited to, N,N-dimethylamino, N,N-diethylamino, N,N-methylethylamino, and the like.

The term "diarylamino" refers to a group having the structure —N(aryl)$_2$ or —N(substituted aryl)$_2$ where substituted aryl is as previously defined. Examples of diarylamino are, but not limited to, N,N-diphenylamino, N,N-dinaphthylamino, N,N-di(toluenyl)amino, and the like.

The term "diheteroarylamino" refers to a group having the structure —N(heteroaryl)$_2$ or —N(substituted heteroaryl)$_2$, where heteroaryl and substituted heteroaryl is as previously defined. Examples of diheteroarylamino are, but not limited to, N,N-difuranylamino, N,N-dithiazolidinylamino, N,N-di(imidazole)amino, and the like.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)-for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991); Bundgaard, et al., Journal of Drug Deliver Reviews, 8:1–38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof, or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:

ACN for acetonitrile;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino)azobenzene)-aminohexyl-1-O-(2-cyanoethyl)-(N,N-diisopropyl)-phosphoramidite;
DCM for dichloromethane;
DIAD for diisopropyl azodicarboxylate;
DIBAL-H for diisobutylaluminum hydride;
DIEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DUPHOS for

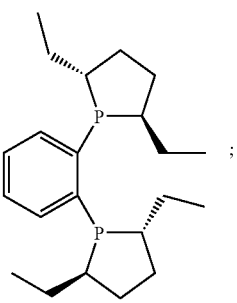

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
HATU for O(7-Azabenzotriazole-1-yl)-N,N,N',N'-tetramethyluronium hexafluorophosphate;
Hoveyda's Cat. for Dichloro(o-isopropoxyphenylmethylene) (tricyclohexylphosphine)ruthenium(II);
KHMDS is potassium bis(trimethylsilyl) amide;
Ms for mesyl;
NMM for N-4-methylmorpholine
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TEA for triethyl amine;
TFA for trifluoroacetic acid;
THF for tetrahydrofuran;
TLC for thin layer chromatography;
TPP or PPh$_3$ for triphenylphosphine;
tBOC or Boc for tert-butyloxy carbonyl; and
Xantphos for 4,5-Bis-diphenylphosphanyl-9,9-dimethyl-9H-xanthene.

Synthetic Methods

The compounds and processes of the present invention will be better understood in connection with the following synthetic schemes which illustrate the methods by which the compounds of the invention may be prepared.

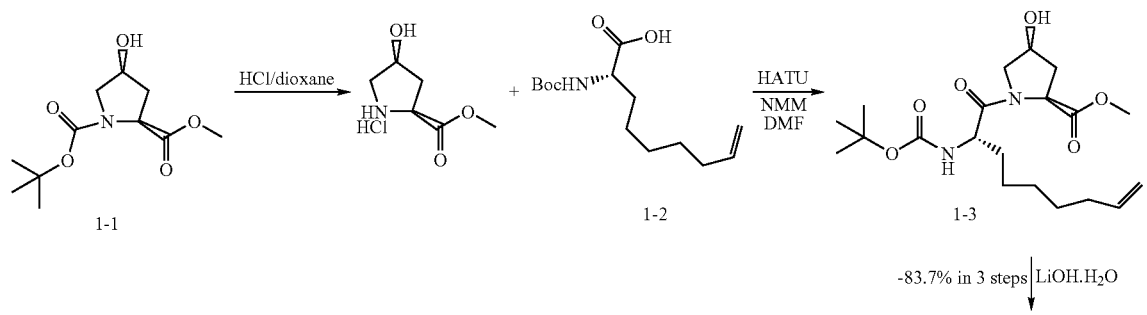

Scheme 1

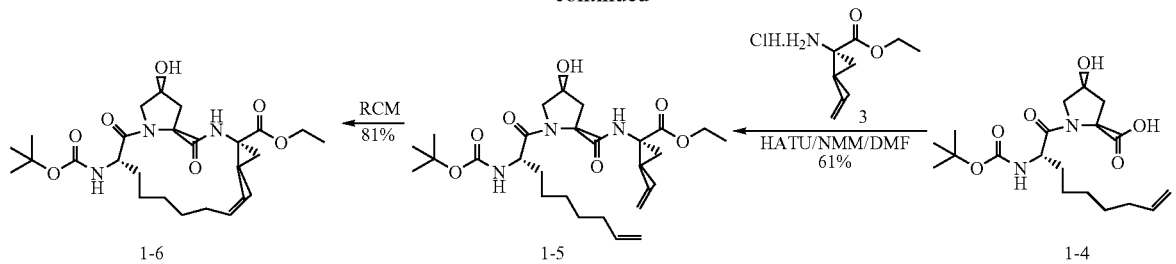

All of the quinoxaline analogs were prepared from the common intermediate If. The synthesis of compound (1-6) is outlined in Scheme 1. Commercially available boc-hydroxyproline (1-1) is treated with HCl in dioxane and is further coupled with acid (1-2) using HATU to afford intermediate (1-3). Other amino acid derivatives containing a terminal alkene may be used in place of (1-2) in order to create varied macrocyclic structures (for further details see WO/0059929). Hydrolysis of (1-3) with LiOH followed by another peptide coupling with cyclopropyl amine (1-4) yielded the tri-peptide (1-5). Finally, ring closure methathesis with a Ruthenium-based catalyst gave the desired key intermediate (1-6) (for further details on ring closing metathesis see recent reviews: Grubbs et al., *Acc. Chem. Res.*, 1995, 28, 446; Shrock et al., *Tetrahedron* 1999, 55, 8141; Furstner, A. *Angew. Chem. Int. Ed.* 2000, 39, 3012; Tmka et al., *Acc. Chem. Res.* 2001, 34, 18; and Hoveyda et al., *Chem. Eur. J.* 2001, 7, 945).

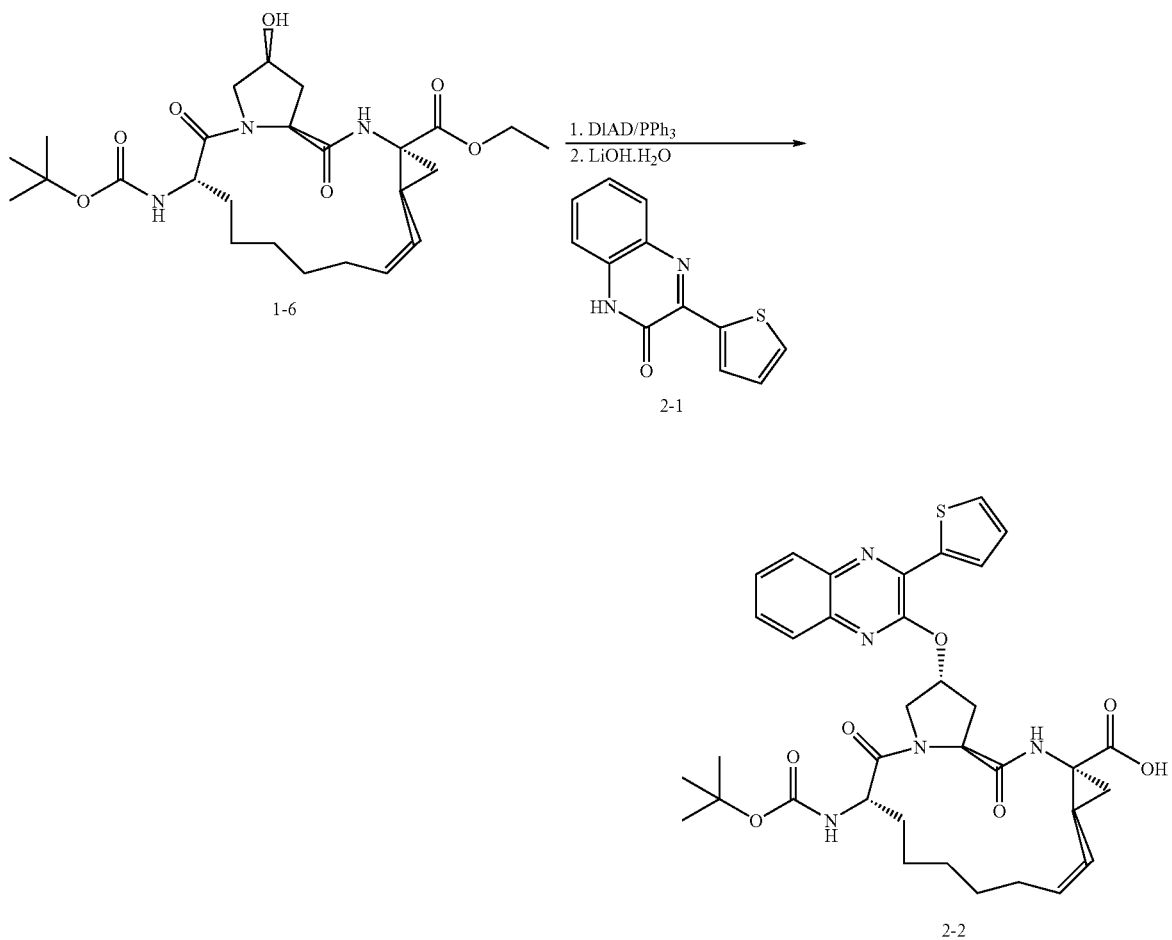

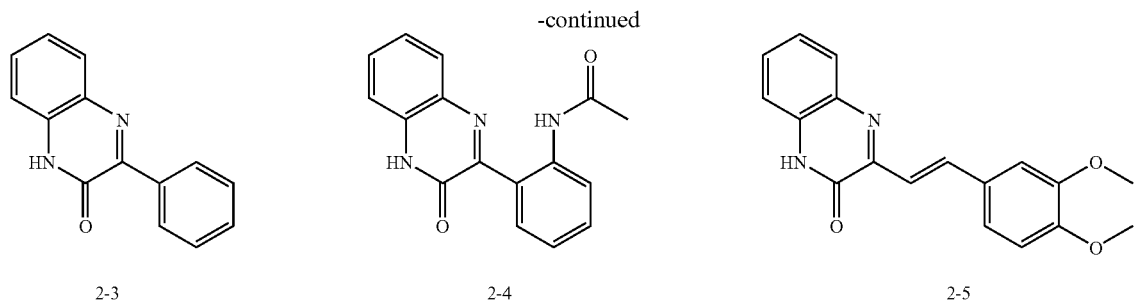

2-3    2-4    2-5

The quinoxaline analogs of the present invention were prepared via several different synthetic routes. The simplest method, shown in Scheme 2, is to condense commercially available 1H-quinoxalin-2-one analogs including, but not limited to, compounds 2-1–2-5 with key intermediate 1-6 by using Mitsunobu conditions followed by hydrolysis with LiOH. The existing literature predicts Mistonobu product formation at the 1 position nitrogen, however attachment at the carbonyl oxygen was observed to form compound 2-2. A detailed discussion of the identification and characterization of the unexpected oxo Mitosunobu addition product appears in the examples herein. For further details on the Mitsunobu reaction, see O. Mitsunobu, *Synthesis* 1981, 1–28; D. L. Hughes, *Org. React.* 29, 1–162 (1983); D. L. Hughes, *Organic Preparations and Procedures Int.* 28, 127–164 (1996); and J. A. Dodge, S. A. Jones, *Recent Res. Dev. Org. Chem.* 1, 273–283 (1997).

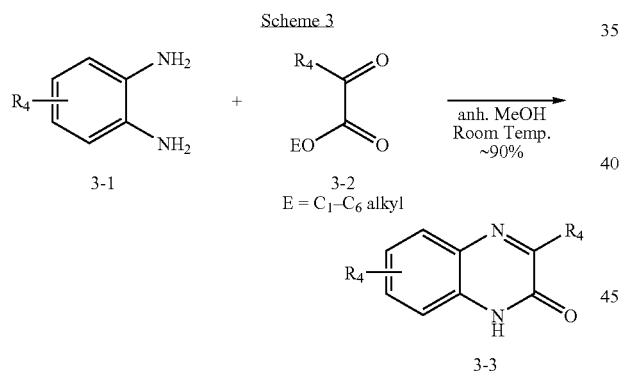

Various quinoxaline derivatives of formula (3-3) can be made with phenyl diamines of formula (3-1), wherein $R_4$ is previously defined, and keto acids or esters of formula (3-2), wherein $R_4$ is previously defined, in anhydrous methanol at room temperature (see Bekerman et al., *J. Heterocycl. Chem.* 1992, 29, 129–133 for further details of this reaction). Examples of phenyl diamines suitable for creating quinoxaline derivatives of formula (3-3) include, but are not limited to, 1,2-diamino-4-nitrobenze, o-phenylenediamine, 3,4-diaminotoluene, 4-chloro-1,2-phenylenediamine, methyl-3,4-diaminobenzoate, benzo[1,3]dioxole-5,6-diamine, 1,2-diamino-4,5-methylene dioxybenzene, 4-chloro-5-(trifluoromethyl)-1,2-benzenediamine, and the like. Examples of keto acids suitable for the reaction described in Scheme 3 include, but are not limited to, benzoylformic acid, phenylpyruvic acid, indole-3-glyoxylic acid, indole-3-pyruvic acid, nitrophenylpyruvic acid, (2-furyl)glyoxylic acid, and the like. Examples of keto esters suitable for the reaction described in Scheme 3 include, but are not limited to, ethyl thiophene-2-glyoxylate, ethyl 2-oxo-4-phenylbutyrate, ethyl 2-(formylamino)-4-thiazolyl glyoxylate, ethyl-2-amino-4-thiozolyl glyoxylate, ethyl-2-oxo-4-phenylbutyrate, ethyl-(5-bromothien-2-yl)glyoxylate, ethyl-3-indolylglyoxylate, ethyl-2-methylbenzoyl formate, ethyl-3-ethylbenzoyl formate, ethyl-3-ethylbenzoyl formate, ethyl-4-cyano-2-oxobutyrate, methyl(1-methylindolyl)-3-glyoxylate, and the like.

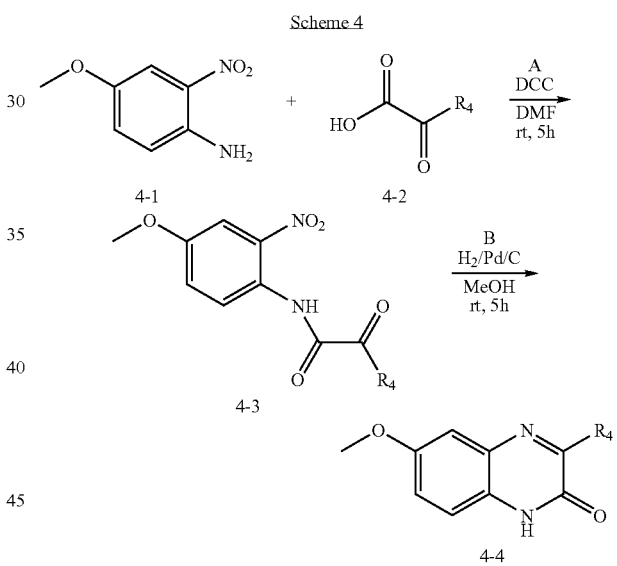

3,6 substituted quinoxalin-2-ones of formula (4-4), wherein $R_4$ is previously defined, can be made in a regioselective manner to favor the 6-positon substitution beginning with the amide coupling of 4-methoxy-2-nitro aniline (4-1) and substituted gloxylic acid (4-2) to yield compound (4-3). The 3,6-substituted quinoxalin-2-one (4-4) is created via catalytic reduction of the nitro of compound (4-3) followed by condensation to the 3,6-substituted quinoxalin-2-one (4-4). Other substituents may be introduced into (4-4) through the use of other 2-nitroanilines. Examples of keto acids suitable for the reaction described in Scheme 4 include, but are not limited to, benzoylformic acid, phenylpyruvic acid, indole-3-glyoxylic acid, indole-3-pyruvic acid, nitrophenylpyruvic acid, (2-furyl)glyoxylic acid, and the like. Examples of 2-nitro anilines suitable for the reaction described in Scheme 4 include, but are not limited to, 4-ethoxy-2-nitroaniline, 4-amino-3-nitrobenzotrifluoride, 4,5-dimethyl-2-nitroaniline, 4-fluoro-2-nitroaniline, 4-chloro-2-nitroaniline, 4-amino-3-nitromethylbenzoate, 4-benzoyl-2-nitroaniline, 3-bromo-4-methoxy-2-nitroaniline, 3'-amino-4'-methyl-2-nitroacetophenone, 5-ethoxy-4-fluoro-2-nitroaniline, 4-bromo-2-nitroaniline, 4-(trifluoromethoxy)-2-nitroaniline, ethyl-4-amino3-nitrobenzoate, 4-bromo-2-methyl-6-nitroaniline, 4-propoxy-2-nitroaniline, 5-(propylthio)-2-nitroaniline, and the like.
Scheme 5
A
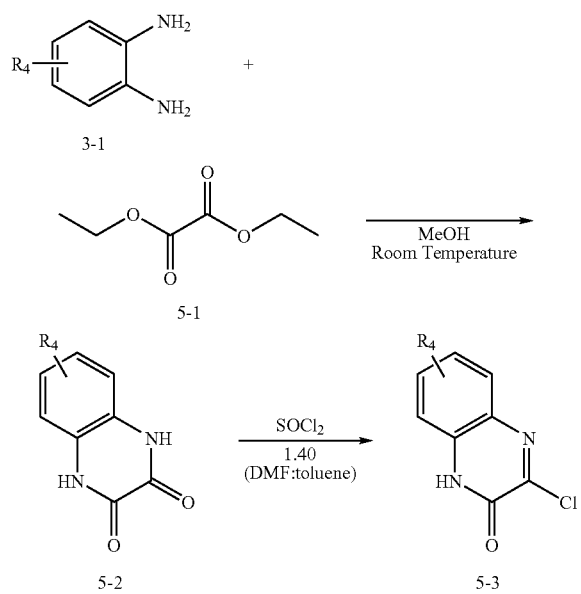
B
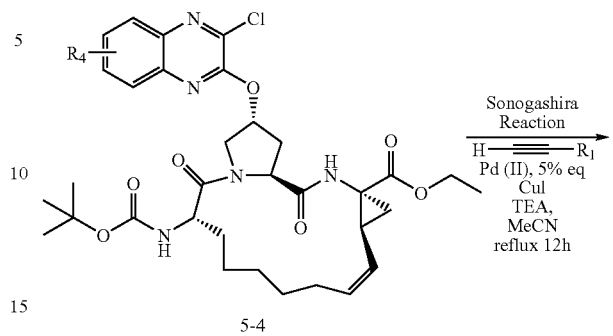
-continued
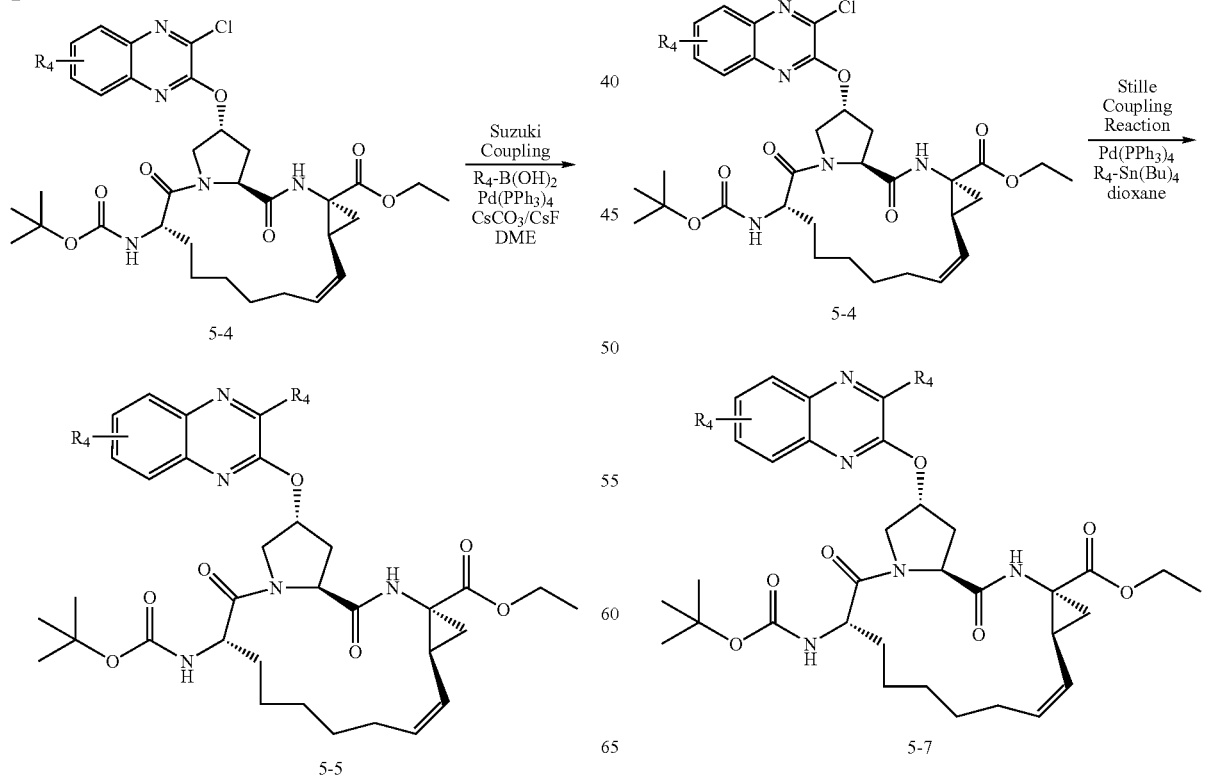

A. A key intermediate, 3-chloro-1H-quinoxalin-2-one (5-3), can be synthesized from phenyl diamines of formula (3-1), as previously defined, and oxalic acid diethyl ester (5-1) to yield 1,4-dihydro-quinoxaline-2,3-dione (5-2) under similar conditions as discussed in Scheme 3 (see Bekerman et al., *J. Heterocycl. Chem.* 1992, 29, 129–133) followed by treatment with $SOCl_2$ (1.37 equiv.) in (1:40 DMF:toluene) (see Loev et al, *J. Med Chem.* (1985), 28, 363–366 for further details).

B. The key 3-chloro-quinoxalin-2-one (5-3) is added to the macrocyclic precursor (1-6) via Mitsunobu conditions, adding via the carbonyl oxygen, rather than the expected 1-position nitrogen, to give the key macrocylic intermediate of formula (5-4). This intermediate facilitates the introduction of various substituents at the 3-position of the quinoxaline.

Suzuki Coupling

Compounds of formula (5-5), wherein $R_4$ is previously defined, can be synthesized via Suzuki coupling reaction with an aryl, substituted aryl, heteroaryl, or substituted heteroaryl boronic acid in DME in the presence of $Pd(PPh_3)_4$, and $CsCO_3$. For further details concerning the Suzuki coupling reaction see A. Suzuki, *Pure Appl. Chem.* 63, 419–422 (1991) and A. R. Martin, Y. Yang, *Acta Chem. Scand.* 47, 221–230 (1993). Examples of boronic acids suitable for Suzuki coupling to macrocyclic key intermediate (5-5) include, but are not limited to, 2-bromo thiophene, phenylboronic acid, 5-bromothiophene-3-boronic acid, 4-cyanophenylboronic acid, 4-trifluormethoxyphenylboronic acid, and the like.

Sonogashira Reaction

Compounds of formula (5-6), wherein $R_1$ is as previously defined, can be synthesized via Sonagashira reaction with the macrocyclic key intermediate a terminal alkyne in acetonitrile in the presence triethylamine, $PdCl_2(PPh_3)_2$, and CuI at 90° C. for 12 hours. For further details of the Sonogashira reaction see Sonogashira, *Comprehensive Organic Synthesis*, Volume 3, Chapters 2,4 and Sonogashira, *Synthesis* 1977, 777. Terminal alkenes suitable for the Sonogashira reaction with macrocyclic key intermediate (5-5) include, but are not limited to, ethynylbenzene, 4-cyano-ethynylbenzene, propargylbenzene, and the like.

Stille Coupling

Compounds of formula (5-7), wherein $R_4$ is previously defined, can be synthesized via Stille coupling reaction with key macrocyclic intermediate of formula (5-4) and aryl stannanes in dioxane in the presence of $Pd(PPh_3)_4$. For further details of the Stille Coupling reaction see J. K. Stille, *Angew. Chem. Int. Ed.* 25, 508–524 (1986), M. Pereyre et al., *Tin in Organic Synthesis* (Butterworths, Boston, 1987) pp 185–207 passim, and a review of synthetic applications in T. N. Mitchell, *Synthesis* 1992, 803–815. Organostannanes suitable for Stille coupling with key macrocyclic intermediate (5-4) include, but are not limited to, tributyltin cyanide, allyl-tri-n-butyltin, 2-tributyltin-pyridine, 2-tri-n-butyltin furan, 2-tri-n-butyltin thiophene, 2,3-dihydron-5-(tri-n-butyltin)benzofuran, and the like.

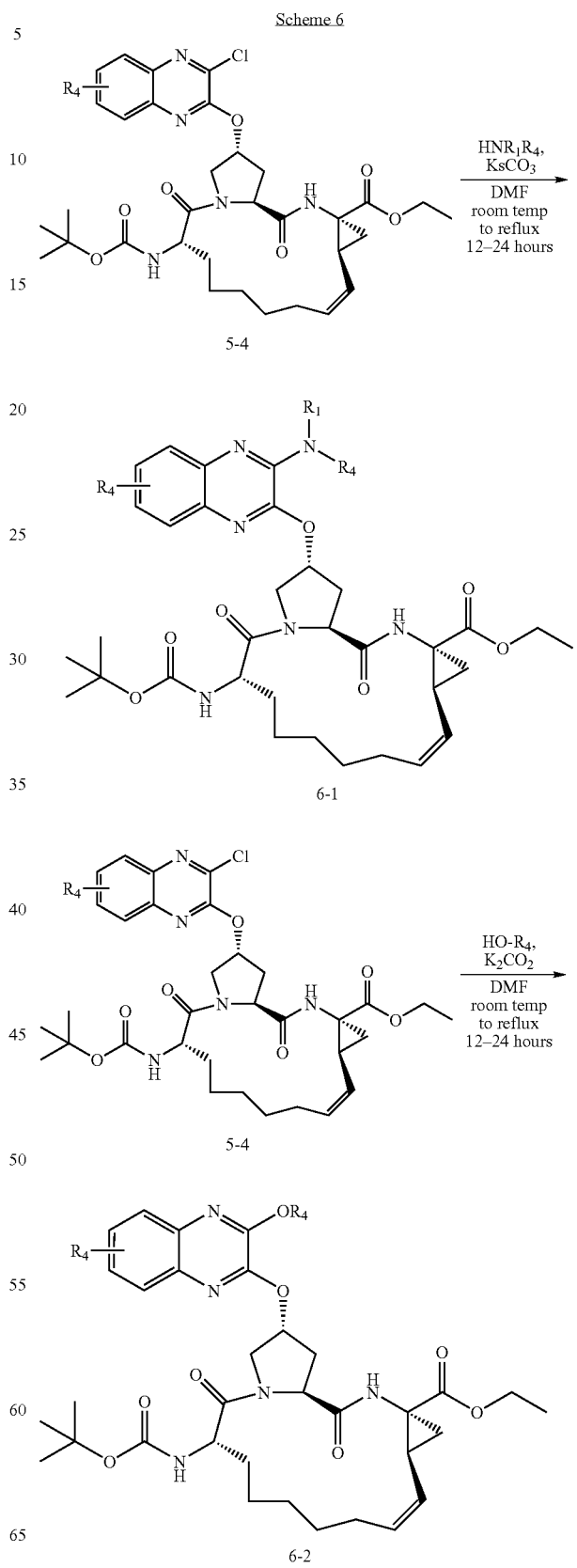

Scheme 6 the various groups that may be introduced are mono-substituted amino, di-substituted amino, ethers, and thio-ethers.

The amino-substituted quinoxaline (6-1), wherein $R_1$ and $R_4$ are as previously defined, can be formed through adding to a 0.1M solution of macrocyclic quinoxalinyl intermediate (5-4) in 10 ml DMF, $K_2CO_3$ (2 equiv.) and $HNR_1R_4$ (1.2 equiv.), and stirring the resulting reaction mixture at room temperature for 5–12 hours. Amines suitable for these conditions include, but are not limited to, ethyl amine, 2-phenyl ethyl amine, cyclohexylamine, ethylmethylamine, diisopropyl amine, benzylethyl amine, 4-pentenyl amine, propargyl amine and the like.

For amines wherein $R_1$ is hydrogen and $R_4$ is aryl, substituted aryl, heteroaryl, or substituted heteroaryl, a different set of conditions must be used to arrive on compound (6-1). Adding of NaH (2 equiv.) and $HNR_5R_6$ (1.2 equiv.) to a 0.1M solution of the macrocyclic quinoxalinyl intermediate (5-4) in THF and stirring the resulting reaction mixture for 5–12 hours affords the aniline substituted compound (6-1). Amines suitable for the instant conditions are aniline, 4-methoxy aniline, 2-amino-pyridine, and the like.

Introduction of ethers to the 2 position of the quinoxaline ring, can be achieved through treating a 0.1M solution of macrocyclic quinoxalinyl intermediate (5-4) in DMF with $K_2CO_3$ (2 equiv.) and $HOR_4$ (1.2 equiv.), wherein $R_4$ is previously defined. The resulting reaction mixture can then be stirred for 5–12 hours at room temperature to arrive at the desired ether moiety at the 3 postion. Alcohols suitable for these conditions include, but are not limited to, ethanol, propanol, isobutanol, trifluoromethanol, phenol, 4-methoxyphenol, pyridin-3-ol, and the like. Thioesters can be made via the same procedure.

Via the key macrocyclic 3-chloro-quinoxalinyl intermediate (5-4), three additional classes of substituents may be introduced at the 3 position of the quinoxaline ring. Among

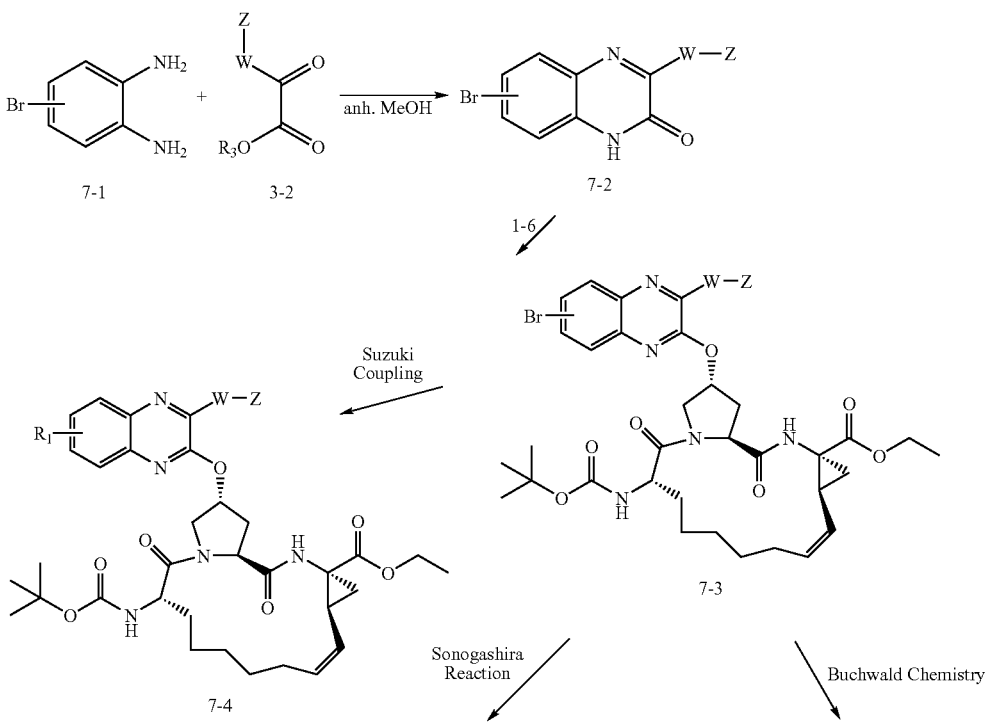

Scheme 7

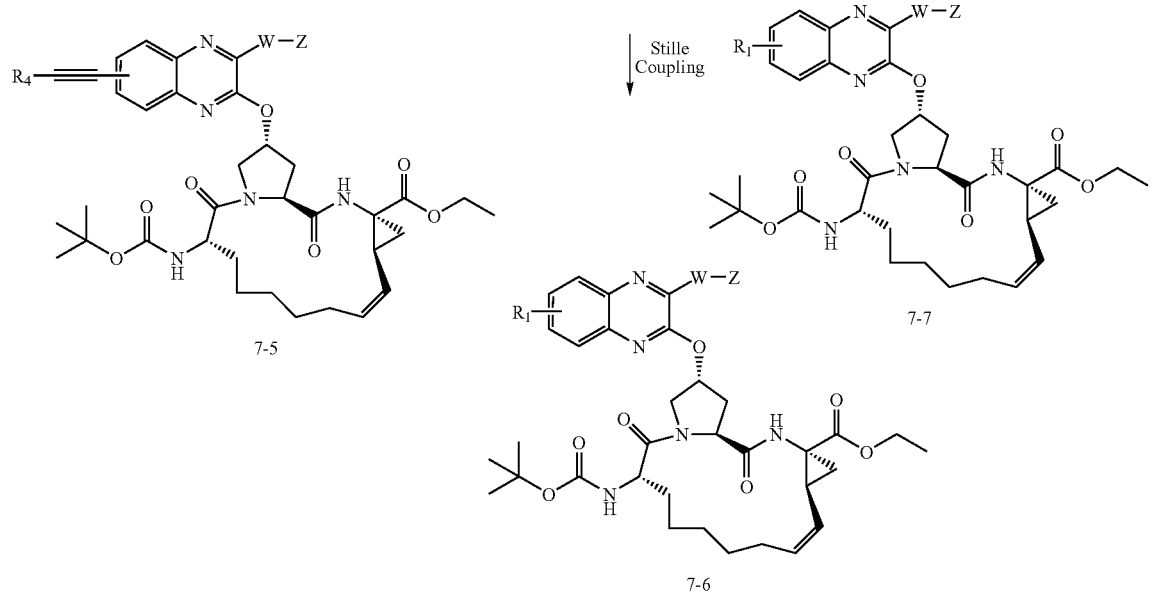

Derivation of the benzo portion of the quinoxaline ring may be achieved through the halogen-substituted quinoxaline of formula (7-2). Quinoxaline of formula (7-2) can be formed with chloro-substituted phenyldiamine (7-1) with diketo compound of formula (7-2), wherein W, Z, and R₃ are as previously defined, in anhydrous methanol as previously detailed. Intermediate (7-3) is formed under Mitsunobu conditions with macrocyclic precursor (7-6) and chlorosubstituted quinoxaline (7-2). Intermediate (7-3) may then undergo Suzuki coupling reactions, Sonogashira reactions, or Stille couplings at the position occupied by the chloro. See previous discussion of Suzuki couplings, Sonogashira reactions, and Stille couplings for further details. The Buchwald reaction allows for the substitution with amines, both primary and secondary, as well as 1H-nitrogen heterocycles at the aryl bromide. For further details of the Buchwald reaction see J. F. Hartwig, *Angew. Chem. Int. Ed.* 37, 2046–2067 (1998).

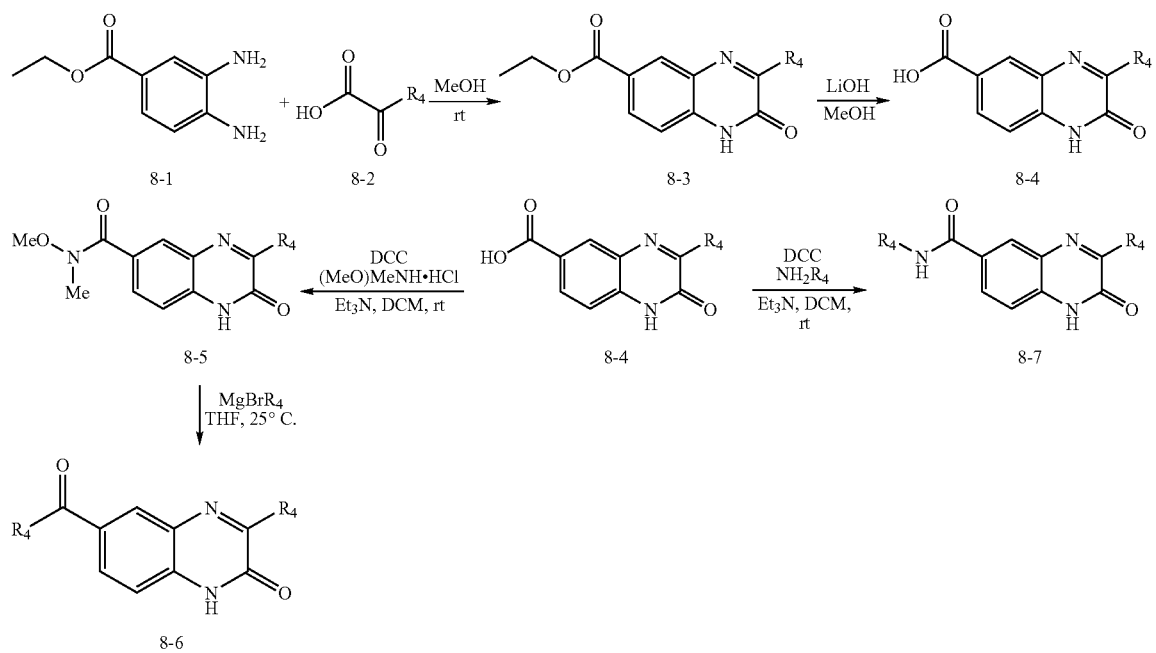

The 3-substituted 2-Oxo-1,2-dihydro-quinoxaline-6-carboxylic acid intermediate (8-4) can be formed via condensation of ethyl 3,4-diaminobenzoate (8-1) and oxo acetic acid of formula (8-2), wherein $R_4$ is previously defined, via the method described previously in Scheme 3 (see Bekerman et al., *J. Heterocycl. Chem.* 1992, 29, 129–133 for further details). The resulting ethyl ester (8-3) is then hydrolyzed with LiOH in MeOH at room temperature to yield carboxylic acid intermediate (8-4).

Carboxylic acid (8-4) then may be converted to substituted ketone (8-6) via Weinreb's amide (8-5) and subsequent treatment with various Grignard Reagents (see Weinreb et al. *Tetrahedron Lett.* 1977, 4171; Weinreb et al, *Synth. Commun.* 1982, 12, 989 for details of the formation and use of Weinreb's amide; and see B. S. Furniss, A. J. Hannaford, P. W. G. Smith, A. R. Tatchell, *Vogel's Textbook of Practical Organic Chemistry*, 5$^{th}$ ed., Longman, 1989). The addition is performed in an inert solvent, generally at low temperatures. Suitable solvents include, but are not limited to, tetrahydrofuran, diethylether, 1,4-dioxane, 1,2-dimethoxyethane, and hexanes. Preferably the solvent is tetrahydrofuran or diethylether. Preferably the reaction is run at −78° C. to 0° C.

In the alternative, carboxylic acid (8-4) may be used to form various amides of formula (8-7), wherein $R_1$ and $R_4$ are previously defined, in a manner generally described in Scheme 8. All of the various quinoxalin-2-one compounds described in Scheme 8 are further coupled to the macrocyclic precursor via the Mitsunobu conditions described above Scheme 9

A

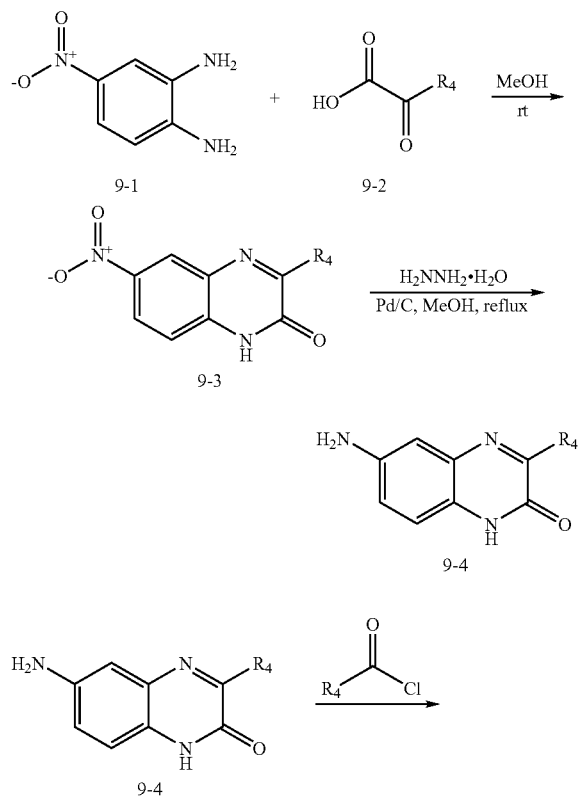

B

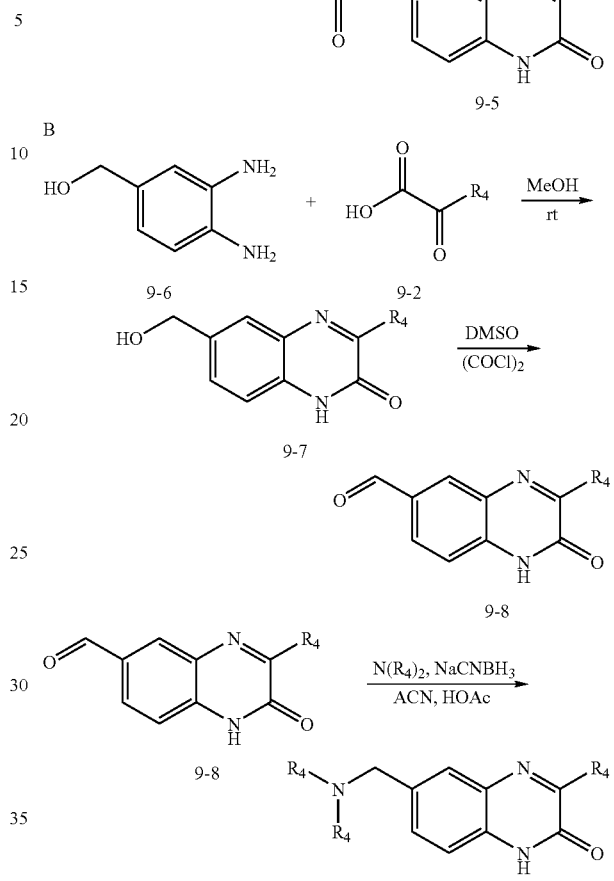

Further 6-substituted quinoxalin-2-one compounds can be made via the procedures set forth generally in Scheme 9.

A. Reduction of 6-nitro and Amide Formation 6-nitro-1H-quinoxalin-2-one (9-3) can be formed in the manner previously described from the 3,4-diaminonitrobenzene and the oxo acetic acid of formula (9-2), wherein $R_4$ is previously described. Reduction of the nitro group at the 6-position can be achieved via Pd/C with $H_2NNH_2 \cdot H_2O$ in refluxing MeOH. The 6-position amine (9-4) then can be treated with a wide array of acid chlorides to arrive upon various amides of formula (9-5).

B. Oxidation of Benzyl Alcohol and Reductive Amination

Quinoxalin-2-one of formula (9-7) can be formed via the condensation of 3,4-diaminobenzyl alcohol and various oxo acetic acids of formula (9-2), wherein $R_4$ is as previously defined as elucidated in previous schemes. The resulting benzyl alcohol (9-7) may then be oxidized under Swern conditions, or any other oxidation conditions to arrive on aldehyde of formula (9-8). For further details concerning the Swern reaction see A. J. Mancuso, D. Swern, *Synthesis* 1981, 165–185 passim; T. T. Tidwell, *Org. React.* 39, 297–572 passim (1990). For other oxidation conditions see B. S. Furniss, A. J. Hannaford, P. W. G Smith, A. R. Tatchell, *Vogel's Textbook of Practical Organic Chemistry*, 5$^{th}$ ed., Longman, 1989. Subsequent reductive amination with primary or secondary amines in the presence of NaCNBH$_3$ and acetic acid can yield compounds of formula (9-9).

Scheme 10

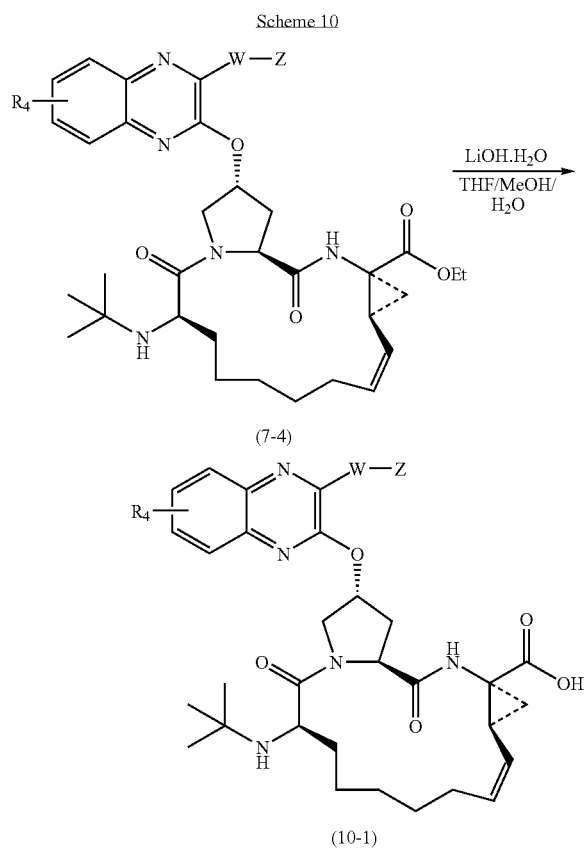

Reduction of the preceding quinoxalinyl macrocyclic compounds is performed by treating a solution of the ethyl ester (7-4) in THF/MeOH/H$_2$O with LiOH.H$_2$O to afford the corresponding free acid.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims

Example 1

Synthesis of the cyclic peptide precursor

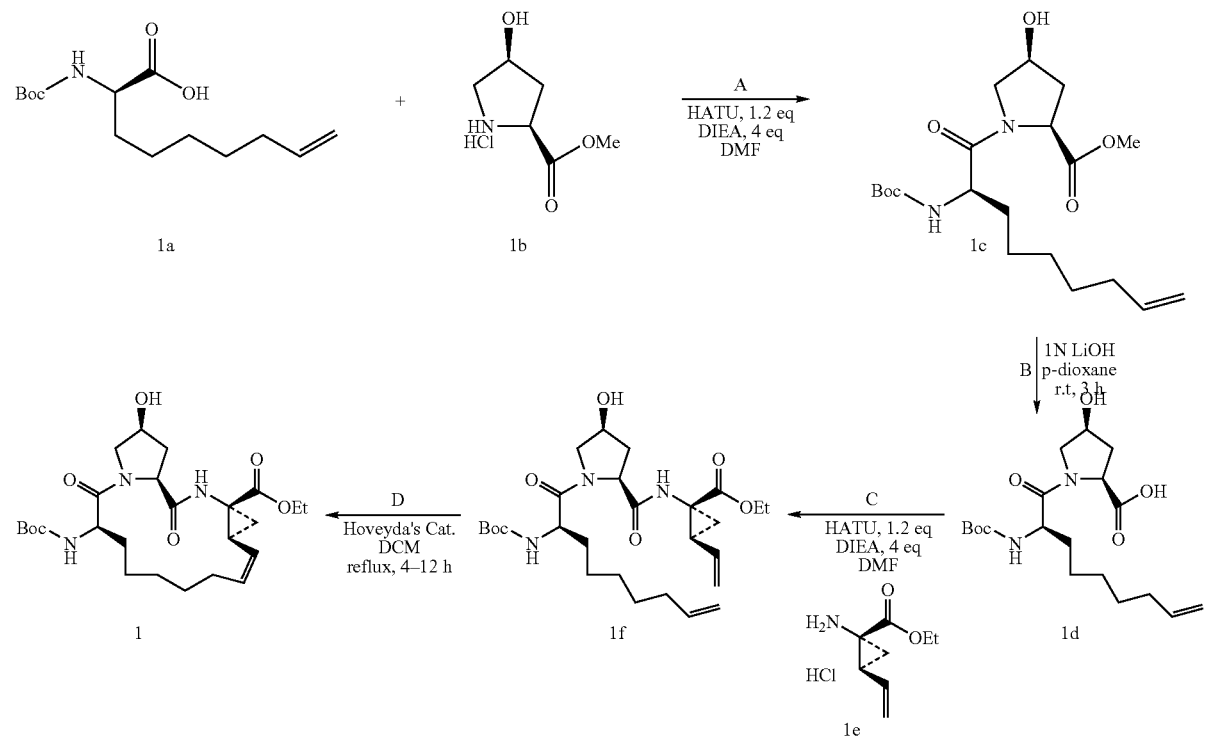

1A. To a solution of Boc-L-2-amino-8-nonenoic acid 1a (1.36 g, 5 mol) and the commercially available cis-L-hydroxyproline methyl ester 1b (1.09 g, 6 mmol) in 15 ml DMF, DIEA (4 ml, 4 eq.) and HATU (4 g, 2 eq) were added. The coupling is carried out at 0° C. over a period of 1 hour. The reaction mixture is diluted with 100 mL EtOAc, and followed by washing with 5% citric acid 2×20 ml, water 2×20 ml, 1M NaHCO$_3$ 4×20 ml and brine 2×10 ml, respectively. The organic phase is dried over anhydrous Na$_2$SO$_4$ and then is evaporated, affording the dipeptide 1c (1.91 g, 95.8%) that is identified by HPLC (Retention time=8.9 min, 30–70%, 90% B), and MS (found 421.37, M+Na$^+$).

1B. The dipeptide 1c (1.91 g) is dissolved in 15 mL of dioxane and 15 mL of 1 N LiOH aqueous solution and the hydrolysis reaction is carried out at room temperature for 4 hours. The reaction mixture is acidified by 5% citric acid and extracted with 100 mL EtOAc, and followed by washing with water 2×20 ml, 1M NaHCO$_3$ 2×20 ml and brine 2×20 ml, respectively. The organic phase is dried over anhydrous Na$_2$SO$_4$ and then removed in vacuum, yielding the free carboxylic acid compound 1d (1.79 g, 97%), which is used for next step synthesis without need for further purification.

1C. To a solution of the free acid obtained above (1.77, 4.64 mmol) in 5 ml DMF, D-β-vinyl cyclopropane amino acid ethyl ester 1e (0.95 g, 5 mmol), DIEA (4 ml, 4 eq.) and HATU (4 g, 2 eq) were added. The coupling is carried out at 0° C. over a period of 5 hour. The reaction mixture is diluted with 80 mL EtOAc, and followed by washing with 5% citric acid 2×20 ml, water 2×20 ml, 1M NaHCO$_3$ 4×20 ml and brine 2×10 ml, respectively. The organic phase is dried over anhydrous Na$_2$SO$_4$ and then evaporated. The residue is purified by silica gel flash chromatography using different ratios of hexanes:EtOAc as elution phase (5:1→3:1→1:1→1:2→1:5). The linear tripeptide 1f is isolated as an oil after removal of the elution solvents (1.59 g, 65.4%), identified by HPLC (Retention time=11.43 min) and MS (found 544.84, M+Na$^+$).

1D. Ring Closing Metathesis (RCM). A solution of the linear tripeptide 1f (1.51 g, 2.89 mmol) in 200 ml dry DCM is deoxygenated by bubbling N$_2$. Hoveyda's 1$^{st}$ generation catalyst (5 mol % eq.) is then added as solid. The reaction is refluxed under N$_2$ atmosphere 12 hours. The solvent is evaporated and the residue is purified by silica gel flash chromatography using different ratios of hexanes:EtOAc as elution phase (9:1→5:1→3:1→1:1→1:2→1:5). The cyclic peptide precursor 1 is isolated as a white powder after removal of the elution solvents (1.24 g, 87%), identified by HPLC (Retention time=7.84 min, 30–70%, 90% B), and MS (found 516.28, M+Na$^+$). For further details of the synthetic methods employed to produce the cyclic peptide precursor 1, see WO 00/059929 (2000).

Example 2

Compound of Formula I, wherein A=tBOC, G=OH, L=absent, X and Y taken together with the carbon atoms to which they are attached are phenyl, W is absent, Z=thiophen-2-yl, j=3, m=s=1, and R$_5$=R$_6$=hydrogen.

Step 2A.

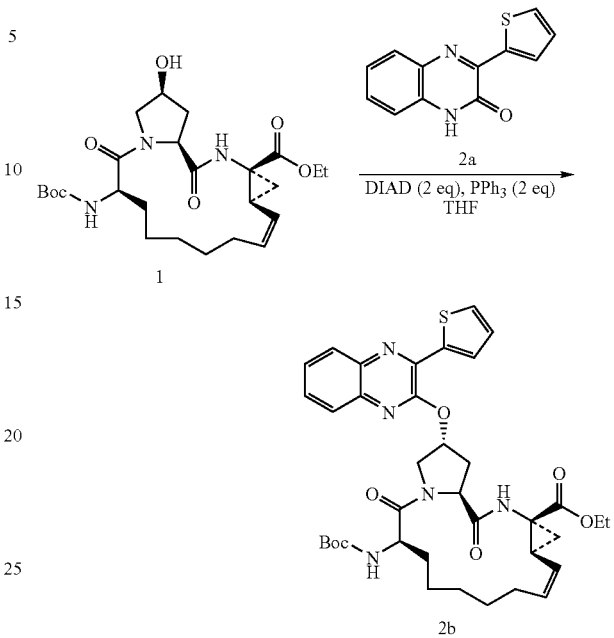

To a cooled mixture of macrocyclic precursor 1,3-(thiophen-2-yl)-1H-quinoxalin-2-one 2a (1.1 equiv.), and triphenylphosphine (2 equiv.) in THF was added DIAD (2 equiv.) dropwise at 0° C. The resulting mixture was held at 0° C. for 15 min. before being warmed to room temperature. After 18 hours, the mixture was concentrated under vacuum and the residue was purified by chromatography eluting with 60% ethyl acetate-hexane to give 2b as a clear oil (35 mg, 99%).

MS (found): 704.4 (M+H). H$^1$-NMR [CDCl$_3$, δ (ppm)]: 8.6 (d, 1H), 8.0 (d, 1H), 7.8 (d, 1H), 7.6 (m, 2H), 7.5 (d, 2H), 7.2 (t, 1H), 7.0 (brs, 1H), 6.0 (brt, 1H), 5.5 (m, 1H), 5.3 (brd, 1H), 5.2 (t, 1H), 5.0 (m. 1H), 4.6 (brt, 1H), 4.1–4.3 (m, 3H), 3.1 (m, 1H), 5.3 (m, 1H), 2.1–2.3 (m, 2H), 1.3 (brs, 9H), 1.2 (t, 3H).

Step 2B.

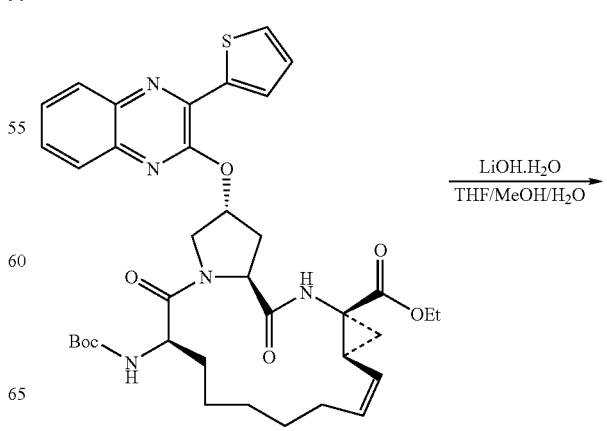

-continued

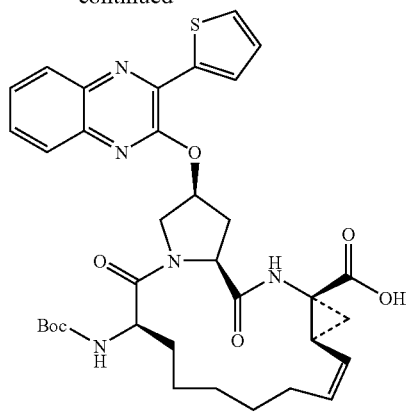

A solution of compound 2b and lithium hydroxide (10 equiv.) in THF/MeOH/H$_2$O (2:1:0.5) was stirred at room temperature for 20 hours. The excess solvents were evaporated in vacuo, the resulting residue was diluted with water, followed by acidification to pH ~5. The mixture was extracted 2 times with ethyl acetate. The combined organic extracts were washed once with brine, dried (MgSO4), filtered and concentrated in vacuo to give an oily residue, which was purified by column chromatography eluting with 2–10% methanol-chloroform (87%).

MS (found): 676.3 $^1$H-NMR [CD$_3$OD, δ (ppm)]: 8.14 (1H), 7.96 (1H), 7.86 (1H), 7.65 (1H), 7.62 (1H), 7.59 (1H), 7.19 (1H), 6.07 (1H), 5.53 (1H), 5.52 (1H), 4.81 (1H), 4.75 (1H), 4.23 (1H), 4.12 (1H), 2.65–2.75 (2H), 2.52 (1H), 2.21 (1H), 1.97 (1H), 1.80 (1H), 1.62 (2H), 1.54 (1H), 1.47 (2H), 1.44 (2H), 1.41 (2H), 1.09 (9H). $^{13}$C-NMR [CD$_3$OD, δ (ppm)]: 176.2, 174.1, 173.4, 156.0, 152.9, 141.0, 139.6, 138.9, 138.6, 131.5, 130.6, 130.0, 129.3, 128.1, 127.8, 127.1, 126.6, 78.6, 76.1, 59.8, 53.3, 52.3, 41.4, 34.5, 32.3, 30.0, 27.5, 27.4, 27.2 (3C), 26.1, 22.6, 22.4.

Example 3

Compound of Formula I, wherein A=tBOC, G=OH, L=absent, X and Y taken together with the carbon atoms to which they are attached are phenyl, W is absent, Z=2-(formamido)-thiazol-4-yl, j=3, m=s=1, and R$_5$=R$_6$=hydrogen.

Step 3A.

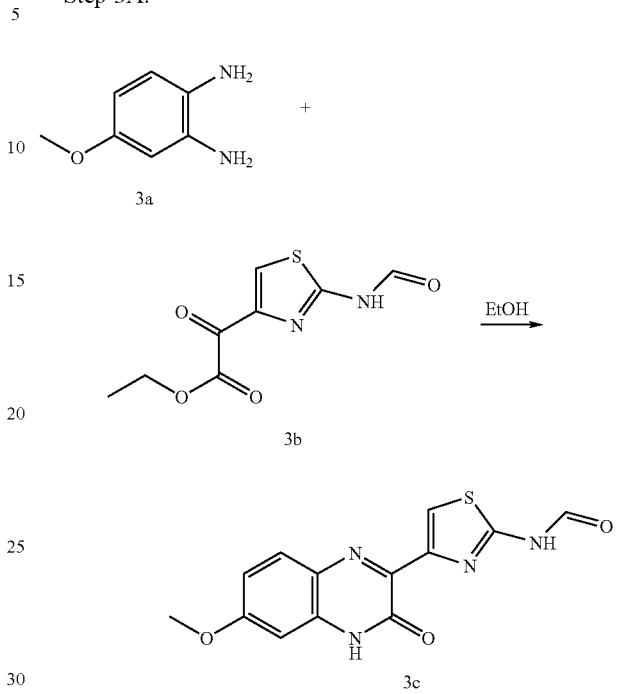

Commercially available 4-Methoxy-benzene-1,2-diamine 3a (3.6 mmol) and (2-Formylamino-thiazol-4-yl)-oxo-acetic acid ethyl ester 3b (1 equiv.) in ethanol (40 mL) was heated to reflux for 5 hours. After the mixture was cooled to room temperature, the excess ethanol was evaporated in vacuo, and the residue was placed under high vacuum for 2 hours to give compound 3c as a greenish yellow powder.

MS (found): 303.1 (M+H). H$^1$-NMR [DMSO-d, δ (ppm)]: 8.7 (s, 1H), 8.6 (m, 2H), 7.2–7.3 (m, 4H), 3.8 (s, 3H).

Step 3B.

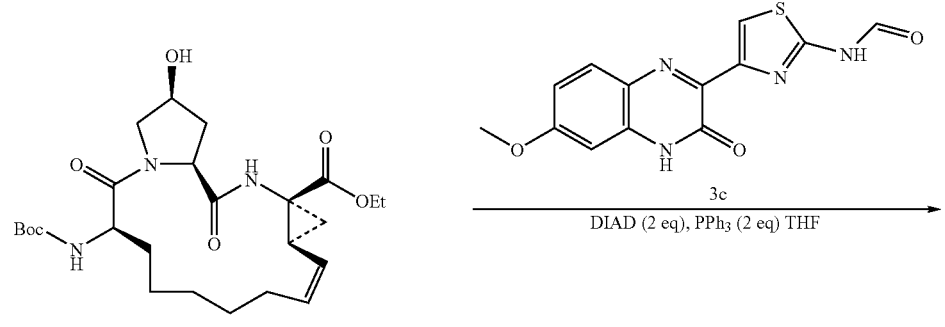

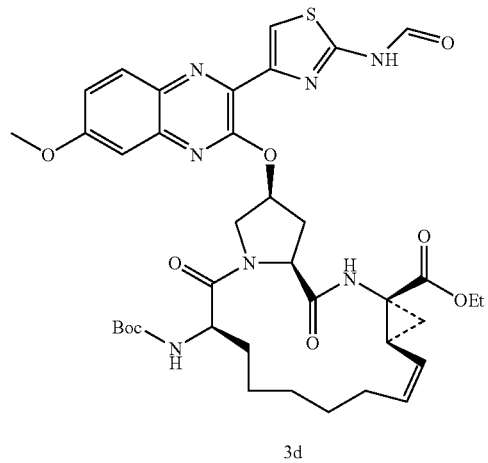

3d

To a cooled mixture of 1, quinoxalin-2-one 3c (1.1 equiv.), triphenylphosphine (2 equiv.) in THF was added DIAD (2 equiv.) dropwise at 0° C. The resulting mixture was kept at 0° C. for 15 min. before warming to room temperature. After 18 hours, the mixture was concentrated in vacuo and the residue was purified by chromatography eluting with 80–100% ethyl acetate-hexane to give 3d as a yellow oil.

MS (found): 778.5 (M+H).

Step 3C.

A solution of 3d and lithium hydroxide (10 equiv.) in THF/MeOH/H$_2$O (2:1:0.5) was stirred at room temperature for 20 hours. The excess solvent was evaporated in vacuo, the residue was diluted with water and followed by acidification to pH ~5. The mixture was extracted 2 times with ethyl acetate. The combined organic extracts were washed once with brine, dried (MgSO4), filtered and concentrated in vacuo to give a solid residue which was purified by HPLC to give.

MS (found): 750.4 (M+H). MS (found): 722.4 (M+H).

Example 4

Compound of Formula I, wherein A=tBOC, G=OH, L=absent, X and Y taken together with the carbon atoms to which they are attached are phenyl, W is absent, Z=ethyl, j=3, m=s=1, and R$_5$=R$_6$=hydrogen.

The title compound is prepared with 3-ethyl-1H-quinoxalin-2-one and the title compound from Example 1 under the Mitsunobu conditions described in Example 2, followed by the reduction of the ethyl ester via treatment with LiOH as elucidated in Example 2.

Example 5

Compound of Formula I, wherein A=tBOC, G=OH, L=absent, X and Y taken together with the carbon atoms to which they are attached are phenyl, W is absent, Z=phenyl, j=3, m=s=1, and R$_5$=R$_6$=hydrogen.

The title compound is prepared with 3-phenyl-1H-quinoxalin-2-one and the title compound from Example 1 under the Mitsunobu conditions described in Example 2, followed by the reduction of the ethyl ester via treatment with LiOH as elucidated in Example 2.

Example 6

Compound of Formula I, wherein A=tBOC, G=OH, L=absent, X and Y taken together with the carbon atoms to which they are attached are phenyl W is absent, Z=4-methoxyphenyl, j=3, m=s=1, and R$_5$ =R$_6$=hydrogen.

The title compound is prepared with 3-(4-methoxyphenyl)-1H-quinoxalin-2-one and the title compound from Example 1 under the Mitsunobu conditions described in Example 2, followed by the reduction of the ethyl ester via treatment with LiOH as elucidated in Example 2.

Example 7

Compound of Formula I, wherein A=tBOC, G=OH, L=absent, X and Y taken together with the carbon atoms to which they are attached are phenyl, W is absent, Z=4-ethoxyphenyl, j=3, m=s=1, and R$_5$=R$_6$=hydrogen.

The title compound is prepared with 3-(4-ethoxyphenyl)-1H-quinoxalin-2-one and the title compound from Example 1 under the Mitsunobu conditions described in Example 2, followed by the reduction of the ethyl ester via treatment with LiOH as elucidated in Example 2.

Example 8

Compound of Formula I, wherein A=tBOC, G=OH, L=absent, X and Y taken together with the carbon atoms to which they are attached are phenyl, W is absent, Z=5-bromothiophen-2-yl, j=3, m=s=1, and R$_5$=R$_6$=hydrogen.

The title compound is prepared with 3-(5-bromothiophen-2-yl)-1H-quinoxalin-2-one and the title compound from Example 1 under the Mitsunobu conditions described in Example 2, followed by the reduction of the ethyl ester via treatment with LiOH as elucidated in Example 2.

Example 9

Compound of Formula I, wherein A=tBOC, G=OH, L=absent X and Y taken together with the carbon atoms to which they are attached are phenyl, W is absent, Z=2-pyrid-3-yl ethylenyl j=3, m=s=1, and R$_5$=R$_6$=hydrogen.

The title compound is prepared with 3-[2-(pyrid-3-yl)-vinyl]-1H-quinoxalin-2-one and the title compound from Example 1 under the Mitsunobu conditions described in Example 2, followed by the reduction of the ethyl ester via treatment with LiOH as elucidated in Example 2.

Example 10

Compound of Formula I, wherein A=tBOC, G=OH, L=absent, X and Y taken together with the carbon atoms to which they are attached are phenyl, W is absent, Z=3,4-Dimethoxy-phenyl, j=3, m=s=1, and $R_5=R_6$=hydrogen.

The title compound is prepared with 3-[2-(3,4-Dimethoxy-phenyl)-vinyl]-1H-quinoxalin-2-one and the title compound from Example 1 under the Mitsunobu conditions described in Example 2, followed by the reduction of the ethyl ester via treatment with LiOH as elucidated in Example 2.

Example 11

Compound of Formula I, wherein A=tBOC, G=OH, L=absent, X and Y taken together with the carbon atoms to which they are attached are phenyl, W is absent, Z=2-thiophen-2-yl ethylenyl, j=3, m=s=1, and $R_5=R_6$=hydrogen.

The title compound is prepared with 3-[2-thiophen-2-yl-vinyl]-1H-quinoxalin-2-one and the title compound from Example 1 under the Mitsunobu conditions described in Example 2, followed by the reduction of the ethyl ester via treatment with LiOH as elucidated in Example 2.

Example 12

Compound of Formula I, wherein A=tBOC, G=OH, L=absent, X and Y taken together with the carbon atoms to which they are attached are phenyl, Z=indole-2-yl, j=3, m=s=1, and $R_5=R_6$=hydrogen.

Preparation of 3-(1H-Indol-3-yl)-1H-quinoxalin-2-one

The quinoxalin-2-one of the present example is prepared by heating the commercially available phenyl-1,2-diamine (3.6 mmol) and indole-3-glyoxylic acid (1 equiv.) in ethanol (40 mL) to reflux for 5 hours. After the mixture is cooled to room temperature, the excess ethanol was evaporated in vacuo, and the residue is placed under high vacuum for 2 hours to give 3-(1H-Indol-3-yl)-1H-quinoxalin-2-one.

Mitsunobu Coupling to Macrocycle

The title compound is prepared with 3-(1H-Indol-3-yl)-1H-quinoxalin-2-one and the title compound from Example 1 under the Mitsunobu conditions described in Example 2, followed by the reduction of the ethyl ester via treatment with LiOH as elucidated in Example 2.

Example 13

Compound of Formula I, wherein A=tBOC, G=OH, L=absent, X and Y taken together with the carbon atoms to which they are attached are phenyl, W is absent, Z=1H-indol-3-yl methyl, j=3, m=s=1, and $R_5=R_6$=hydrogen.

Preparation of 3-(1H-Indol-3-ylmethyl)-1H-quinoxalin-2-one

The quinoxalin-2-one of the present example is prepared with phenyl-1,2-diamine and indole-3-pyruvic acid via the method described in Example 12 to afford 3-(1H-Indol-3-ylmethyl)-1H-quinoxalin-2-one.

Mitsunobu Coupling to Macrocycle

The title compound is prepared with 3-(1H-Indol-3-ylmethyl)-1H-quinoxalin-2-one and the title compound from Example 1 under the Mitsunobu conditions described in Example 2, followed by the reduction of the ethyl ester via treatment with LiOH as elucidated in Example 2.

Example 14

Compound of Formula I, wherein A=tBOC, G=OH, L=absent, X and Y taken together with the carbon atoms to which they are attached are phenyl, W is absent, Z=furan-2-yl, j=3, m=s=1, and $R_5=R_6$=hydrogen.

Preparation of 3-(furan-2-yl)-1H-quinoxalin-2-one

The quinoxalin-2-one of the present example is prepared with phenyl-1,2-diamine and furan-2-yl glyoxylic acid via the method described in Example 12 to afford 3-(furan-2-yl)-1H-quinoxalin-2-one.

Mitsunobu Coupling to Macrocycle

The title compound is prepared with 3-(furan-2-yl)-1H-quinoxalin-2-one and the title compound from Example 1 under the Mitsunobu conditions described in Example 2, followed by the reduction of the ethyl ester via treatment with LiOH as elucidated in Example 2.

Example 15

Compound of Formula I, wherein A=tBOC, G=OH, L=absent, X and Y taken together with the carbon atoms to which they are attached are phenyl, W is absent, Z=1H-benzoimidazol-2-yl, j=3, m=s=1, and $R_5=R_6$=hydrogen.

Preparation of 3-(1H-benzoimidazol-2-yl)-1-H-quinoxalin-2-one

The quinoxalin-2-one of the present example is prepared with phenyl-1,2-diamine and (1H-benzoimidazol-2-yl) oxo-acetic acid via the method described in Example 12 to afford 3-(1H-benzoimidazol-2-yl)-1H-quinoxalin-2-one.

Mitsunobu Coupling to Macrocycle

The title compound is prepared with 3-(1H-benzoimidazol-2-yl)-1H-quinoxalin-2-one and the title compound from Example 1 under the Mitsunobu conditions described in Example 2, followed by the reduction of the ethyl ester via treatment with LiOH as elucidated in Example 2.

Example 16

Compound of Formula I, wherein A=tBOC, G=OH, L=absent, X and Y taken together with the carbon atoms to which they are attached are phenyl W is absent, Z=1H-imidazol-2-ylmethyl, j=3, m=s=1, and $R_5=R_6$=hydrogen.

Preparation of 3-(1H-Imidazol-2-ylmethyl)-1H-quinoxalin-2-one

The quinoxalin-2-one of the present example is prepared with phenyl-1,2-diamine and (1H-benzoimidazol-2-yl) oxo-acetic acid via the method described in Example 12 to afford 3-(1H-Imidazol-2-ylmethyl)-1H-quinoxalin-2-one.

Mitsunobu Coupling to Macrocycle

The title compound is prepared with 3-(1H-Imidazol-2-ylmethyl)-1H-quinoxalin-2-one and the title compound from Example 1 under the Mitsunobu conditions described in Example 2, followed by the reduction of the ethyl ester via treatment with LiOH as elucidated in Example 2.

Example 17

Compound of Formula I, wherein A=tBOC, G=OEt, L=absent, X and Y taken together with the carbon atoms to which they are attached are phenyl, W is absent, Z=chloro, j=3, m=s=1, and $R_5=R_6$=hydrogen.

Preparation of 3-chloro-1H-quinoxalin-2-one

The quinoxalin-2-one of the present example is prepared with phenyl-1,2-diamine and oxalic acid via the method described in Example 12 to afford the 1,4-Dihydro quinoaxline-2,3-dione. The 1,4-Dihydro quinoaxline-2,3-dione is then treated with SOCl$_2$ in 2.5% DMF:toluene, heated to 130° C., stirred for 2 h, filtered and concentrated to afford the 3-chloro-1H-quinoxalin-2-one in crude form.

Mitsunobu Coupling to Macrocycle

The title compound is prepared with 3-chloro-1H-quinoxalin-2-one and the title compound from Example 1 under the Mitsunobu conditions described in Example 2.

Example 18

Compound of Formula I, wherein A=tBOC, G=OH, L=absent, X and Y taken together with the carbon atoms to which they are attached are phenyl, Z=thiophen-3-yl, j=3, m=s=1, and $R_5=R_6$=hydrogen.

To a mixture of the title compound of Example 17 (0.055 mmol), 3-thiophene boronic acid (0.28 mmol), cesium carbonate (0.22 mmol), potassium fluoride monohydrate (0.44 mmol) is placed in a round bottom flask and is flushed twice with nitrogen. To this mixture is added DME and the resulting solution is flushed again with nitrogen before palladium tetrakis(triphenylphopshine) (10 mol %) is added. After flushing two more times with nitrogen, the mixture is heated to reflux for 20 hours. The mixture is then cooled and then diluted with water and extracted three times with EtOAc. The combined EtOAc layers are washed once with brine, dried (MgSO$_4$), filtered and concentrated in vacuo. The residue is purified by column chromatography eluting with 20–40% EtOAc-hexane to yield the ethyl ester precursor of the title compound. The ethyl ester is then hydrolyzed to the free acid via treatment with LiOH as elucidated in Example 2 to arrive at the title compound.

Example 19

Compound of Formula I, wherein A=tBOC, G=OH, L=absent, X and Y taken together with the carbon atoms to which they are attached are phenyl, W is absent, Z=2-pyrid-3-yl acetylenyl, j=3, m=s=1, and $R_5=R_6$=hydrogen.

The title compound is prepared by reaction of a degassed solution of the title compound from Example 17 (4 mmol), 2-pyrid-3-yl acetylene (4 mmol), and 1 ml of triethylamine and 10 ml of acetonitrile with PdCl$_2$(PPh$_3$)$_2$ (0.2 mmol) and CuI (0.1 mmol). The resulting reaction mixture is degassed and stirred for 5 minutes at room temperature. The reaction is then heated to 90° C. and stirred for 12 hours. Subsequently, the reaction mixture is concentrated in vacuo and purified by silica column to afford the ethyl ester of the title compound. The ethyl ester is then hydrolyzed to the free acid via treatment with LiOH as elucidated in Example 2 to arrive at the title compound.

Example 20

Compound of Formula I, wherein A=tBOC, G=OH, L=absent, X and Y taken together with the carbon atoms to which they are attached are phenyl, W is absent, Z=2,3-dihydrobenzofuran-5-yl, j=3, m=s=1, and $R_5=R_6$=hydrogen.

To a degassed solution of the title compound of Example 17 (1 mmol) and 2,3-dihydrobenzofuran-5-yl stannane (2 mmol) is added Pd(PPh$_3$)$_4$ (10 mol %). The mixture is degassed with nitrogen two additional times and heated to 100° C. for 3 hours. The cooled mixture is concentrated in vacuo and the residue is purified by column chromatography (30% EtOAc/Hexane) to give the ethyl ester of the title compound. The ethyl ester is then hydrolyzed via treatment with LiOH as elucidated in Example 2 to give the title compound.

Example 21

Compound of Formula I, wherein A=tBOC, G=OH, L=absent, X and Y taken together with the carbon atoms to which they are attached are phenyl, W=—NH—, Z=propargyl, j=3, m=s=1, and $R_5=R_6$=hydrogen.

The title compound is formed by reacting a 0.1M solution of the title compound from Example 17 in DMF with propargylamine (1.2 equiv.) in the presence of K$_2$CO$_3$ (2 equiv.) at room temperature for 5–12 hours. The resulting reaction mixture is then extracted with EtOAc, washed with NaHCO$_3$, water, and brine, and the washed extract is concentrated in vacuo. The residue is then purified by silica chromatography to yield the ethyl ester of the title compound. The ethyl ester is then hydrolyzed to the free acid via treatment with LiOH to arrive upon the title compound.

Example 22

Compound of Formula I, wherein A=tBOC, G=OH, L=absent, X and Y taken together with the carbon atoms to which they are attached are phenyl, W=—N(ethyl)-, Z=benzyl, j=3, m=s=1, and $R_5=R_6$=hydrogen.

The title compound is formed by reacting a 0.1M solution of the title compound from Example 17 in DMF with benzylethylamine (1.2 equiv.) in the presence of K$_2$CO$_3$ (2 equiv.) at room temperature for 5–12 hours. The resulting reaction mixture is then extracted with EtOAc, washed with NaHCO$_3$, water, and brine, and the washed extract is concentrated in vacuo. The residue is then purified by silica chromatography to yield the ethyl ester of the title compound. The ethyl ester is then hydrolyzed to the free acid via treatment with LiOH to arrive upon the title compound.

Example 23

Compound of Formula I, wherein A=tBOC, G=OH, L=absent, X and Y taken together with the carbon atoms to which they are attached are phenyl, W=—NH—, Z=pyrid-3-yl, j=3, m=s=1, and $R_5=R_6$=hydrogen.

The title compound is formed by reacting a 0.1M solution of the title compound from Example 17 in DMF with 3-aminopyridine (1.2 equiv.) in the presence of K$_2$CO$_3$ (2 equiv.) at room temperature for 5–12 hours. The resulting reaction mixture is then extracted with EtOAc, washed with NaHCO$_3$, water, and brine, and the washed extract is concentrated in vacuo. The residue is then purified by silica chromatography to yield the ethyl ester of the title compound. The ethyl ester is then hydrolyzed to the free acid via treatment with LiOH to arrive upon the title compound.

Example 24

Compound of Formula I, wherein A=tBOC, G=OH, L=absent, X and Y taken together with the carbon atoms to which they are attached are phenyl, W is absent, Z=tetrazolyl, j=3, m=s=1, and $R_5=R_6$=hydrogen.

The title compound is formed by reacting a 0.1M solution of the title compound from Example 17 in DMF with tetrazole (1.2 equiv.) in the presence of K$_2$CO$_3$ (2 equiv.) at room temperature for 5–12 hours. The resulting reaction mixture is then extracted with EtOAc, washed with NaHCO$_3$, water, and brine, and the washed extract is concentrated in vacuo. The residue is then purified by silica chromatography to yield the ethyl ester of the title compound. The ethyl ester is then hydrolyzed to the free acid via treatment with LiOH to arrive upon the title compound.

Example 25

Compound of Formula I, wherein A=tBOC, G=OH, L=absent, X and Y taken together with the carbon atoms to which they are attached are phenyl, W is absent, Z=morpholino, j=3, m=s=1, and $R_5=R_6$=hydrogen.

The title compound is formed by reacting a 0.1M solution of the title compound from Example 17 in DMF with morpholine (1.2 equiv.) in the presence of $K_2CO_3$ (2 equiv.) at room temperature for 5–12 hours. The resulting reaction mixture is then extracted with EtOAc, washed with $NaHCO_3$, water, and brine, and the washed extract is concentrated in vacuo. The residue is then purified by silica chromatography to yield the ethyl ester of the title compound. The ethyl ester is then hydrolyzed to the free acid via treatment with LiOH to arrive upon the title compound.

Example 26

Compound of Formula I, wherein A=tBOC, G=OH, L=absent, X and Y taken together with the carbon atoms to which they are attached are phenyl, W=—O—, Z=thiophen-3-yl-methyl, j=3, m=s=1, and $R_5=R_6$=hydrogen.

The title compound is formed by reacting a 0.1M solution of the title compound from Example 17 in DMF with thiophen-3-yl methanol (1.2 equiv.) in the presence of $K_2CO_3$ (2 equiv.) at room temperature for 5–12 hours. The resulting reaction mixture is then extracted with EtOAc, washed with $NaHCO_3$, water, and brine, and the washed extract is concentrated in vacuo. The residue is then purified by silica chromatography to yield the ethyl ester of the title compound. The ethyl ester is then hydrolyzed to the free acid via treatment with LiOH to arrive upon the title compound.

Example 27

Compound of Formula I, wherein A=tBOC, G=OH, L=absent, X and Y taken together with the carbon atoms to which they are attached are

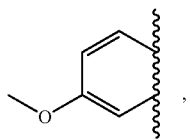

,

W is absent, Z=thiophen-2-yl, j=3, m=s=1, and $R_5=R_6$=hydrogen.

Preparation of 7-Methoxy-3-thiophen-2-yl-1H-quinoxalin-2-one

The quinoxalin-2-one of the present example is prepared with 4-Methoxy-benzene-1,2-diamine and (thiophen-2-yl) oxo-acetic acid via the method described in Example 12 to afford 7-Methoxy-3-thiophen-2-yl-1H-quinoxalin-2-one.

Mitsunobu Coupling to Macrocycle

The title compound is prepared with 7-Methoxy-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 28

Compound of Formula I, wherein A=tBOC, G=OH, L=absent, X and Y taken together with the carbon atoms to which they are attached are

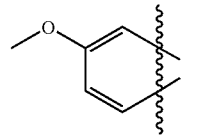

,

W is absent, Z=thiophen-2-yl, j=3, m=s=1, and $R_5=R_6$=hydrogen.

Preparation of 7-Methoxy-3-thiophen-2-yl-1H-quinoxalin-2-one

The 2-nitro amide precursor of the present example is prepared with 4-Methoxy-2-nitroaniline (1 equiv.) and 2-(thiophen-2-yl) oxoacetic acid (1 equiv.) in DMF in the presence of DCC at room temperature to 80° C. to arrive at the precursor 2-nitro amide (N-(4-Methoxy-2-nitro-phenyl)-2-oxo-2-thiophen-2-yl-acetamide). The precursor 2-nitro amide is subjected to catalytic hydrogenation conditions ($H_2$/Pd/C in MeOH) forming the amine followed by ring closure to form 6-Methoxy-3-thiophen-2-yl-1H-quinoxalin-2-one.

Mitsunobu Coupling to Macrocycle

The title compound is prepared with 6-Methoxy-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 29

Compound of Formula I, wherein A=tBOC, G=OH, L=absent, X and Y taken together with the carbon atoms to which they are attached are

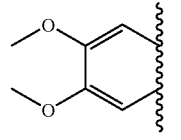

,

W is absent, Z=thiophen-2-yl, j=3, m=s=1, and $R_5=R_6$=hydrogen.

Preparation of 6,7-Methoxy-3-thiophen-2-yl-1-H-quinoxalin-2-one

The quinoxalin-2-one of the present example is prepared with 4,5-Dimethoxy-benzene-1,2-diamine and (thiophen-2-yl) oxo-acetic acid via the method described in Example 12 to afford 6,7-Methoxy-3-thiophen-2-yl-1H-quinoxalin-2-one.

Mitsunobu Coupling to Macrocycle

The title compound is prepared with 6,7-Methoxy-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 30

Compound of Formula I, wherein A=tBOC, G=OH, L=absent, X and Y taken together with the carbon atoms to which they are attached are

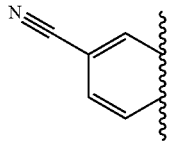

,

W is absent, Z=thiophen-2-yl, j=3, m=s=1, and $R_5=R_6$=hydrogen.

Preparation of 6-cyano-3-thiophen-2-yl-1H-quinoxalin-2-one

The quinoxalin-2-one of the present example is prepared with 4-cyano-benzene-1,2-diamine and (thiophen-2-yl) oxo-acetic acid via the method described in Example 12 to afford 6-cyano-3-thiophen-2-yl-1H-quinoxalin-2-one.

Mitsunobu Coupling to Macrocycle

The title compound is prepared with 6-cyano-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 31

Compound of Formula I, wherein A=tBOC, G=OH, L=absent, X and Y taken together with the carbon atoms to which they are attached are

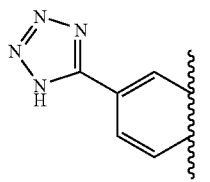

,

W is absent, Z=thiophen-2-yl, j=3, m=s=1, and $R_5=R_6$=hydrogen.

Preparation of 6-tetrazol-5-yl-3-thiophen-2-yl-1H-quinoxalin-2-one

The quinoxalin-2-one of the present example is prepared with 4-cyano-benzene-1,2-diamine and (thiophen-2-yl) oxo-acetic acid via the method described in Example 12 to afford 6-cyano-3-thiophen-2-yl-1H-quinoxalin-2-one. The cyano compound is then treated with $NaN_3$ (5 eqiv.), $Et_3N$ (3 equiv.), in Xylenes in a sealed tube and heated to 140° C. and stirred 12 hours to afford the 6-tetrazol-5-yl-3-thiophen-2-yl-1H-quinoxalin-2-one after extraction and purification.

Mitsunobu Coupling to Macrocycle

The title compound is prepared with 6-tetrazol-5-yl-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 32

Compound of Formula I, wherein A=tBOC, G=OH, L=absent, X and Y taken together with the carbon atoms to which they are attached are

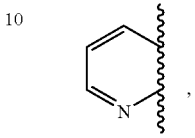

,

W is absent, Z=thiophen-2-yl, j=3, m=s=1, and $R_5=R_6$=hydrogen.

Preparation of 2-Thiophen-2-yl-4H-pyrido[2,3-b]pyrazin-3-one

The quinoxalin-2-one of the present example is prepared with 2,3-diamino pyridine and (thiophen-2-yl) oxo-acetic acid via the method described in Example 12 to afford 2-thiophen-2-yl-4H-pyrido[2,3-b]pyrazin-3-one.

Mitsunobu Coupling to Macrocycle

The title compound is prepared with 2-thiophen-2-yl-4H-pyrido[2,3-b]pyrazin-3-one and the title compound from Example 1 under the Mitsunobu conditions described in Example 2, followed by the reduction of the ethyl ester via treatment with LiOH as elucidated in Example 2.

Example 33

Compound of Formula I, wherein A=tBOC, G=OH, L=absent, X and Y taken together with the carbon atoms to which they are attached are

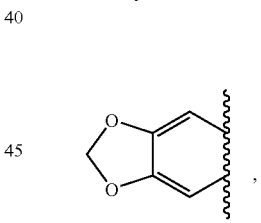

,

W is absent, Z=thiophen-2-yl, j=3, m=s=1, and $R_5=R_6$=hydrogen

Preparation of 7-Thiophen-2-yl-5H-1,3-dioxa-5,8-diaza-cyclopenta[b]naphthalen-6-one The quinoxalin-2-one of the present example is prepared with Benzo[1,3]dioxole-5,6-diamine and (thiophen-2-yl) oxo-acetic acid via the method described in Example 12 to afford 7-thiophen-2-yl-5H-1,3-dioxa-5,8-diaza-cyclopenta[b]naphthalen-6-one.

Mitsunobu Coupling to Macrocycle

The title compound is prepared with 7-thiophen-2-yl-5H-1,3-dioxa-5,8-diaza-cyclopenta[b]naphthalen-6-one and the title compound from Example 1 under the Mitsunobu conditions described in Example 2, followed by the reduction of the ethyl ester via treatment with LiOH as elucidated in Example 2.

Example 34

Compound of Formula I, wherein A=tBOC, G=OH, L=absent, X and Y taken together with the carbon atoms to which they are attached are

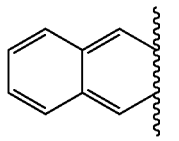

,

W is absent, Z=thiophen-2-yl, j=3, m=s=1, and $R_5=R_6$=hydrogen.

Preparation of 3-Thiophen-2-yl-1H-benzo[g]quinoxalin-2-one

The quinoxalin-2-one of the present example is prepared with napthylene-2,3-diamine and (thiophen-2-yl) oxo-acetic acid via the method described in Example 12 to afford 3-Thiophen-2-yl-1H-benzo[g]quinoxalin-2-one.

Mitsunobu Coupling to Macrocycle

The title compound is prepared with 3-Thiophen-2-yl-1H-benzo[g]quinoxalin-2-one and the title compound from Example 1 under the Mitsunobu conditions described in Example 2, followed by the reduction of the ethyl ester via treatment with LiOH as elucidated in Example 2.

Example 35

Compound of Formula I, wherein A=tBOC, G=OH, L=absent, X and Y taken together with the carbon atoms to which they are attached are

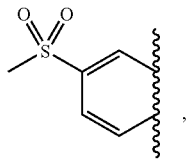

,

W is absent, Z=thiophen-2-yl, j=3, m=s=1, and $R_5=R_6$=hydrogen.

Preparation of 6-Methanesulfonyl-3-thiophen-2-yl-1H-quinoxalin-2-one

The quinoxalin-2-one of the present example is prepared with 4-Methanesulfonyl-benzene-1,2-diamine and (thiophen-2-yl) oxo-acetic acid via the method described in Example 12 to afford 6-Methanesulfonyl-3-thiophen-2-yl-1H-quinoxalin-2-one.

Mitsunobu Coupling to Macrocycle

The title compound is prepared with 6-Methanesulfonyl-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 36

Compound of Formula I, wherein A=tBOC, G=OH, L=Wbsent, X and Y taken together with the carbon atoms to which they are attached are

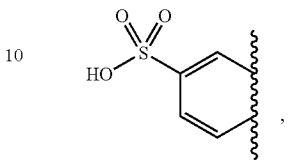

,

W is absent, Z=thiophen-2-yl, j=3, m=s=1, and $R_5=R_6$=hydrogen.

Preparation of 2-Oxo-3-thiophen-2-yl-1,2-dihydro-quinoxaline-6-sulfonic acid

The quinoxalin-2-one of the present example is prepared with 3,4-Diamino-benzenesulfonic acid and (thiophen-2-yl) oxo-acetic acid via the method described in Example 12 to afford 2-Oxo-3-thiophen-2-yl-1,2-dihydro-quinoxaline-6-sulfonic acid.

Mitsunobu Coupling to Macrocycle

The title compound is prepared with 2-Oxo-3-thiophen-2-yl-1,2-dihydro-quinoxaline-6-sulfonic acid and the title compound from Example 1 under the Mitsunobu conditions described in Example 2, followed by the reduction of the ethyl ester via treatment with LiOH as elucidated in Example 2.

Example 37

Compound of Formula I, wherein A=tBOC, G=OH, L=absent X and Y taken together with the carbon atoms to which they are attached are

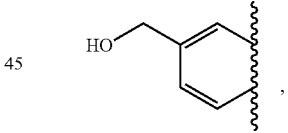

,

W is absent, Z=thiophen-2-yl, j=3, m=s=1, and $R_5=R_6$=hydrogen.

Preparation of 6-Hydroxymethyl-3-thiophen-2-yl-1H-quinoxalin-2-one

The quinoxalin-2-one of the present example is prepared with (3,4-Diamino-phenyl)-methanol and (thiophen-2-yl) oxo-acetic acid via the method described in Example 12 to afford 6-Hydroxymethyl-3-thiophen-2-yl-1H-quinoxalin-2-one.

Mitsunobu Coupling to Macrocycle

The title compound is prepared with 6-Hydroxymethyl-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 38

Compound of Formula I, wherein A=tBOC, G=OH, L=absent, X and Y taken together with the carbon atoms to which they are attached are

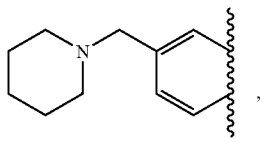,

W is absent, Z=thiophen-2-yl, j=3, m=s=1, and $R_5=R_6$=hydrogen.

Preparation of 6-Piperidin-1-ylmethyl-3-thiophen-2-yl-1H-quinoxalin-2-one

The quinoxalin-2-one of the present example is prepared first via Swern oxidation with DMSO and $(COCl)_2$ of 6-Hydroxymethyl-3-thiophen-2-yl-1H-quinoxalin-2-one to form 2-Oxo-3-thiophen-2-yl-1,2-dihydro-quinoxaline-6-carbaldehyde. The 6-carboxaldehyde compound then undergoes reductive amination with piperidine in acetonitrile in the presence of $NaCNBH_3$ and acetic acid to afford, after an aqueous workup and purification, 6-Piperidin-1-ylmethyl-3-thiophen-2-yl-1H-quinoxalin-2-one.

Mitsunobu Coupling to Macrocycle

The title compound is prepared with 6-Piperidin-1-ylmethyl-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 39

Compound of Formula I, wherein A=tBOC, G=OH, L=absent, X and Y taken together with the carbon atoms to which they are attached are

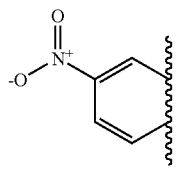,

W is absent, Z=thiophen-2-yl, j=3, m=s=1, and $R_5=R_6$=hydrogen.

Preparation of 6-Nitro-3-thiophen-2-yl-1H-quinoxalin-2-one

The quinoxalin-2-one of the present example is prepared with 4-Nitro-benzene-1,2-diamine and (thiophen-2-yl) oxoacetic acid via the method described in Example 12 to afford 6-Nitro-3-thiophen-2-yl-1H-quinoxalin-2-one.

Mitsunobu Coupling to Macrocycle

The title compound is prepared with 6-Nitro-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 40

Compound of Formula I, wherein A=tBOC, G=OH, L=absent, X and Y taken together with the carbon atoms to which they are attached are

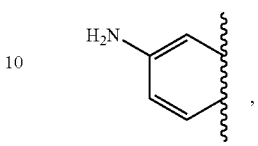,

W is absent, Z=thiophen-2-yl, j=3, m=s=1, and $R_5=R_6$=hydrogen.

Preparation of 6-amino-3-thiophen-2-yl-1H-quinoxalin-2-one

The quinoxalin-2-one of the present example is prepared by reducing 6-nitro-3-thiophen-2-yl-1H-quinoxalin-2-one of Example 39 with $H_2NNH_2 \cdot H_2O$ in the presence of Pd/C in refluxing MeOH.

Mitsunobu Coupling to Macrocycle

The title compound is prepared with 6-amino-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 41

Compound of Formula I, wherein A=tBOC, G=OH, L=absent, X and Y taken together with the carbon atoms to which they are attached are

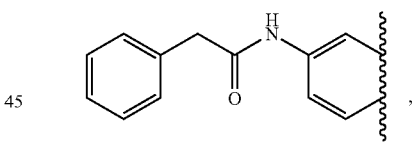,

W is absent, Z=thiophen-2-yl, j=3, m=s=1, and $R_5=R_6$=hydrogen.

Preparation of N-(2-Oxo-3-thiophen-2-yl-1,2-dihydro-quinoxalin-6-yl)-2-phenyl-acetamide The quinoxalin-2-one of the present example is prepared by treating 6-amino-3-thiophen-2-yl-1H-quinoxalin-2-one of Example 40 with phenethyl acid chloride to afford, after workup and purification, N-(2-Oxo-3-thiophen-2-yl-1,2-dihydro-quinoxalin-6-yl)-2-phenyl-acetamide.

Mitsunobu Coupling to Macrocycle

The title compound is prepared with N-(2-Oxo-3-thiophen-2-yl-1,2-dihydro-quinoxalin-6-yl)-2-phenyl-acetamide and the title compound from Example 1 under the Mitsunobu conditions described in Example 2, followed by the reduction of the ethyl ester via treatment with LiOH as elucidated in Example 2.

Example 42

Compound of Formula I, wherein A=tBOC, G=OH, L=absent, X and Y taken together with the carbon atoms to which they are attached are

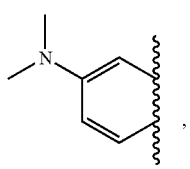

,

W is absent, Z=thiophen-2-yl, j=3, m=s=1, and $R_5=R_6$=hydrogen.

Preparation of 6-Nitro-3-thiophen-2-yl-1H-quinoxalin-2-one

The quinoxalin-2-one of the present example is prepared with 4-Nitro-benzene-1,2-diamine and (thiophen-2-yl) oxoacetic acid via the method described in Example 12 to afford 6-Nitro-3-thiophen-2-yl-1H-quinoxalin-2-one.

Mitsunobu Coupling to Macrocycle

The title compound is prepared with 6-Nitro-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 43

Compound of Formula I, wherein A=tBOC, G=OH, L=absent, X and Y taken together with the carbon atoms to which they are attached are

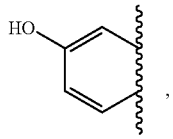

,

W is absent, Z=thiophen-2-yl, j=3, m=s=1, and $R_5=R_6$=hydrogen.

Preparation of 6-hydroxy-3-thiophen-2-yl-1H-quinoxalin-2-one

The quinoxalin-2-one of the present example is prepared with 3,4-diaminophenol (which is prepared by treating 3,4-dinitrophenol with $H_2NNH_2.H_2O$, Pd/C refluxed in MeOH), and (thiophen-2-yl) oxo-acetic acid via the method described in Example 12 to afford 6-hydroxy-3-thiophen-2-yl-1H-quinoxalin-2-one.

Mitsunobu Coupling to Macrocycle

The title compound is prepared with 6-hydroxy-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 44

Compound of Formula I, wherein A=tBOC, G=OH, L=absent, X and Y taken together with the carbon atoms to which they are attached are

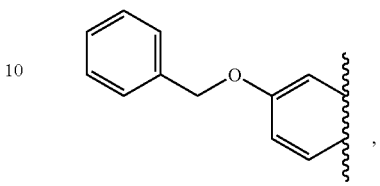

,

W is absent, Z=thiophen-2-yl, j=3, m=s=1, and $R_5=R_6$=hydrogen.

Preparation of 6-Benzyloxy-3-thiophen-2-yl-1H-quinoxalin-2-one

The quinoxalin-2-one of the present example is prepared treating 6-hydroxy-3-thiophen-2-yl-1H-quinoxalin-2-one from Example 43 in DMF with bromomethyl benzene in the presence of $K_2CO_3$ at a temperature between 25° C. to 80° C. The resulting reaction mixture, after workup and purification, affords 6-benzyloxy-3-thiophen-2-yl-1H-quinoxalin-2-one.

Mitsunobu Coupling to Macrocycle

The title compound is prepared with 6-benzyloxy-3-thiophen-2-yl-1H-quinoxalin-2-one and the title compound from Example 1 under the Mitsunobu conditions described in Example 2, followed by the reduction of the ethyl ester via treatment with LiOH as elucidated in Example 2.

Example 45

Compound of Formula I, wherein A=tBOC, G=OH, L=absent, X and Y taken together with the carbon atoms to which they are attached are

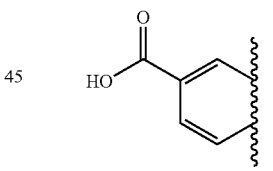

,

W is absent, Z=thiophen-2-yl, j=3, m=s=1, and $R_5=R_6$=hydrogen.

Preparation of 2-Oxo-3-thiophen-2-yl-1,2-dihydro-quinoxaline-6-carboxylic acid ethyl ester The quinoxalin-2-one of the present example is prepared with 3,4-Diamino-benzoic acid ethyl ester and (thiophen-2-yl) oxo-acetic acid via the method described in Example 12 to afford 2-Oxo-3-thiophen-2-yl-1,2-dihydro-quinoxaline-6-carboxylic acid ethyl ester.

Mitsunobu Coupling to Macrocycle

The title compound is prepared with 2-Oxo-3-thiophen-2-yl-1,2-dihydro-quinoxaline-6-carboxylic acid ethyl ester and the title compound from Example 1 under the Mitsunobu conditions described in Example 2, followed by the reduction of the ethyl esters via treatment with LiOH as elucidated in Example 2.

Example 46

Compound of Formula I, wherein A=tBOC, G=OH, L=absent, X and Y taken together with the carbon atoms to which they are attached are

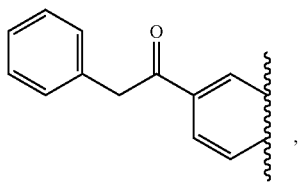

W is absent, Z=thiophen-2-yl, j=3, m=s=1, and R$_5$=R$_6$=hydrogen.

Preparation of 6-Phenylacetyl-3-thiophen-2-yl-1H-quinoxalin-2-one

Step 40a

The quinoxalin-2-one of the present example is prepared with 2-Oxo-3-thiophen-2-yl-1,2-dihydro-quinoxaline-6-carboxylic acid ethyl ester from Example 45 via the hydrolysis of the ethyl ester according to the procedure of Example 2 to afford the carboxylic acid.

Step 40b

The carboxylic acid is then dissolved in DMF in the presence of DCC and triethylamine and to the resulting reaction mixture is added (MeO)NHMe to form Weinreb's amide. The Weinreb's amide is then treated with magnesium benzyl bromide in THF at −75° C. to afford, after extraction and purification, the 6-Phenylacetyl-3-thiophen-2-yl-1H-quinoxalin-2-one.

Mitsunobu Coupling to Macrocycle

The title compound is prepared with 6-Phenylacetyl-3-thiophen-2-yl-1H-quinoxalin-2-one and the title compound from Example 1 under the Mitsunobu conditions described in Example 2, followed by the reduction of the ethyl esters via treatment with LiOH as elucidated in Example 2.

Example 47

Compound of Formula I, wherein A=tBOC, G=OH, L=absent, X and Y taken together with the carbon atoms to which they are attached are

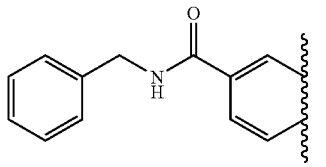

W is absent, Z=thiophen-2-yl, j=3, m=s=1, and R$_5$=R$_6$=hydrogen.

Preparation of 2-Oxo-3-thiophen-2-yl-1,2-dihydro-quinoxaline-6-carboxylic acid benzylamide Step 41a The quinoxalin-2-one of the present example is prepared with 2-Oxo-3-thiophen-2-yl-1,2-dihydro-quinoxaline-6-carboxylic acid benzylamide from Example 45 via the hydrolysis of the ethyl ester according to the procedure of Example 2 to afford the carboxylic acid.

Step 41b

The carboxylic acid is then dissolved in DMF in the presence of DCC and triethylamine and to the resulting reaction mixture is added benzyl amine to afford, after extraction and purification, 2-Oxo-3-thiophen-2-yl-1,2-dihydro-quinoxaline-6-carboxylic acid benzylamide.

Mitsunobu Coupling to Macrocycle

The title compound is prepared with 2-Oxo-3-thiophen-2-yl-1,2-dihydro-quinoxaline-6-carboxylic acid benzylamide and the title compound from Example 1 under the Mitsunobu conditions described in Example 2, followed by the reduction of the ethyl esters via treatment with LiOH as elucidated in Example 2.

Example 48

Compound of Formula I, wherein A=tBOC, G=OH, L=absent, X and Y taken together with the carbon atoms to which they are attached are

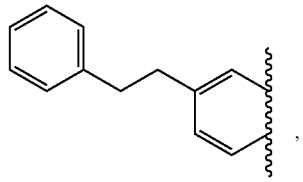

W is absent, Z=thiophen-2-yl, j=3, m=s=1, and R$_5$=R$_6$=hydrogen.

Preparation of 6-Phenethyl-3-thiophen-2-yl-1H-quinoxalin-2-one

The quinoxalin-2-one of the present example is prepared with 6-Phenylacetyl-3-thiophen-2-yl-1H-quinoxalin-2-one from Example 46 via treatment with H$_2$/Pd—C in the presence of acetic acid to form the 6-phenethyl compound.

Mitsunobu Coupling to Macrocycle

The title compound is prepared with 6-Phenethyl-3-thiophen-2-yl-1H-quinoxalin-2-one and the title compound from Example 1 under the Mitsunobu conditions described in Example 2, followed by the reduction of the ethyl esters via treatment with LiOH as elucidated in Example 2.

Example 49

Compound of Formula I, wherein A=tBOC, G=OEt, L=absent, X and Y taken together with the carbon atoms to which they are attached are

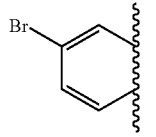

W is absent, Z=thiophen-2-yl, j=3, m=s=1, and R$_5$=R$_6$=hydrogen.

Preparation of 6-bromo-3-thiophen-2-yl-1H-quinoxalin-2-one

The quinoxalin-2-one of the present example is prepared with 4-bromo-2-nitroaniline and (thiophen-2-yl) oxo-acetic acid via the method described in Example 12 to afford 6-bromo-3-thiophen-2-yl-1H-quinoxalin-2-one.

Mitsunobu Coupling to Macrocycle

The title compound is prepared with 6-bromo-3-thiophen-2-yl-1H-quinoxalin-2-one and the title compound from Example 1 under the Mitsunobu conditions described in Example 2 to afford the title compound.

Example 50

Compound of Formula I, wherein A=tBOC, G=OH, L=absent, X and Y taken together with the carbon atoms to which they are attached are

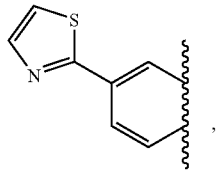

,

W is absent, Z=thiophen-2-yl, j=3, m=s=1, and $R_5=R_6$=hydrogen.

To a degassed solution of the title compound of Example 49 (1 mmol) and thiazol-2yl stannane (2 mmol) is added $Pd(PPh_3)_4$ (10 mol %). The mixture is degassed with nitrogen two additional times and heated to 100° C. for 3 hours. The cooled mixture is concentrated in vacuo and the residue is purified by column chromatography (30% EtOAc/Hexane) to give the ethyl ester of the title compound. The ethyl ester is then hydrolyzed via treatment with LiOH as elucidated in Example 2 to give the title compound.

Example 51

Compound of Formula I, wherein A=tBOC, G=OH, L=absent, X and Y taken together with the carbon atoms to which they are attached are

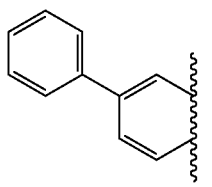

,

W is absent, Z=thiophen-2-yl, j=3, m=s=1, and $R_5=R_6$=hydrogen.

To a mixture of the title compound of Example 49 (0.055 mmol), phenyl boronic acid (0.28 mmol), cesium carbonate (0.22 mmol), potassium fluoride monohydrate (0.44 mmol) is placed in a round bottom flask and is flushed twice with nitrogen. To this mixture is added DME and the resulting solution is flushed again with nitrogen before palladium tetrakis(triphenylphopshine) (10 mol %) is added. After flushing two more times with nitrogen, the mixture is heated to reflux for 20 hours. The mixture is then cooled and then diluted with water and extracted three times with EtOAc. The combined EtOAc layers are washed once with brine, dried ($MgSO_4$), filtered and concentrated in vacuo. The residue is purified by column chromatography eluting with 20–40% EtOAc-hexane to yield the ethyl ester precursor of the title compound. The ethyl ester is then hydrolyzed to the free acid via treatment with LiOH as elucidated in Example 2 to arrive at the title compound.

Example 52

Compound of Formula I, wherein A=tBOC, G=OH, L=absent, X and Y taken together with the carbon atoms to which they are attached are

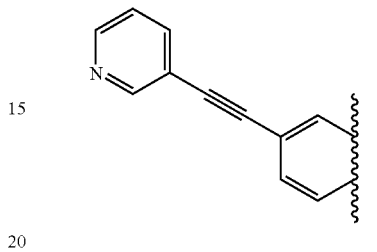

,

W is absent, Z=thiophen-2-yl, j=3, m=s=1, $R_5=R_6$=hydrogen.

The title compound is prepared by reaction of a degassed solution of the title compound from Example 49 (4 mmol), 2-pyrid-3-yl acetylene (4 mmol), and 1 ml of triethylamine and 10 ml of acetonitrile with $PdCl_2(PPh_3)_2$ (0.2 mmol) and CuI (0.1 mmol). The resulting reaction mixture is degassed and stirred for 5 minutes at room temperature. The reaction is then heated to 90° C. and stirred for 12 hours. Subsequently, the reaction mixture is concentrated in vacuo and purified by silica column to afford the ethyl ester of the title compound. The ethyl ester is then hydrolyzed to the free acid via treatment with LiOH as elucidated in Example 2 to arrive at the title compound.

Example 53

Compound of Formula I, wherein A=tBOC, G=OH, L=absent, X and Y taken together with the carbon atoms to which they are attached are

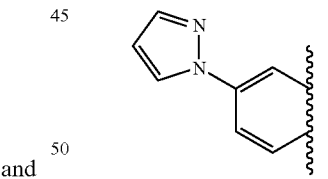

,

W is absent, Z=thiophen-2-yl, j=3, m=s=1, $R_5=R_6$=hydrogen.

The title compound is prepared by adding to a dry mixture of the title compound from Example 49 (0.068 mmol), imidazole (2 eq.), $Cs_2CO_3$ (3 eq.), Xantphos (30 mol %), and $Pd(OAc)_2$ under nitrogen dioxane. The reaction mixture is then degassed and stirred at 75° C. for 18 hours. Upon completion of the reaction, monitored via TLC, the reaction mixture is diluted with DCM, filtered, and concentrated in vacuo. The reaction mixture is then purified via silica column chromatography with 5% $MeOH/CHCl_3$ to afford the ethyl ester of the title compound. The ethyl ester is then hydrolyzed by the conditions set forth in Example 2 to afford the title compound.

Example 54

Compound of Formula I, wherein A=—(C=O)—O—R$^1$, wherein R$^1$=cyclopentyl, G=OH, L=absent, X and Y taken together with the carbon atoms to which they are attached are phenyl, W is absent, Z=thiophen-2-yl, j=3, m=s=1, and R$_5$=R$_6$=hydrogen.

54a—Amine Deprotection.

0.041 mmol of the title compound of Example 2 is dissolved in 4 ml of a 4M solution of HCl in dioxane and stirred for 1 hour. The reaction residue 54a is concentrated in vacuo.

54b—Chloroformate Reagent

The chloroformate reagent 54b is prepared by dissolving 0.045 mmol of cyclopentanol in THF (3 ml) and adding 0.09 mmol of phosgene in toluene (20%). The resulting reaction mixture is stirred at room temperature for 2 hours and the solvent is removed in vacuo. To the residue is added DCM and subsequently concentrated to dryness twice in vacuo yielding chloroformate reagent 54b.

54c—Carbamate Formation

The title carbamate is prepared by dissolving residue 54a in 1 ml of THF, adding 0.045 mmol of TEA, and cooling the resulting reaction mixture to 0° C. To this 0° C. reaction mixture is added chloroformate reagent 54b in 3 ml of THF. The resulting reaction mixture is reacted for 2 hours at 0° C., extracted with EtOAc, washed by 1M sodium bicarbonate, water and brine, dried over MgSO$_4$, and concentrated in vacuo to dryness. The crude compound is purified by silica column and the ethyl ester is subsequently hydrolyzed by the procedure set forth in Example 2.

Example 55

Compound of Formula I, wherein A=—(C=O)—O—R$^1$, wherein R$^1$=cyclobutyl, G=OH, L=absent, X and Y taken together with the carbon atoms to which they are attached are phenyl, W is absent, Z=thiophen-2-yl, j=3, m=s=1, and R$_5$=R$_6$=hydrogen.

The title compound is prepared by the method described in Example 54 with the title compound of Example 2 and cyclobutanol.

Example 56

Compound of Formula I, wherein A=—(C=O)—O—R$^1$, wherein R$^1$=cyclohexyl, G=OH, L=absent, X and Y taken together with the carbon atoms to which they are attached are phenyl, W is absent, Z=thiophen-2-yl, j=3, m=s=1, and R$_5$=R$_6$=hydrogen.

The title compound is prepared by the method described in Example 54 with the title compound of Example 2 and cyclohexanol.

Example 57

Compound of Formula I, wherein A=—(C=O)—O—R$^1$, wherein R$^1$=

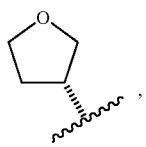

G=OH, L=absent, X and Y taken together with the carbon atoms to which they are attached are phenyl, W is absent, Z=thiophen-2-yl, j=3, m=s=1, and R$_5$=R$_6$=hydrogen.

The title compound is prepared by the method described in Example 54 with the title compound of Example 2 and (R)-3-hydroxytetrahydrofuran.

Example 58

Compound of Formula I, wherein A=—(C=O)—O—R$^1$, wherein R$^1$=

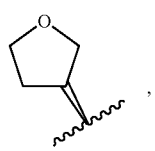

G=OH, L=absent, X and Y taken together with the carbon atoms to which they are attached are phenyl, W is absent, Z=thiophen-2-yl, j=3, m=s=1, and R$_5$=R$_6$=hydrogen.

The title compound is prepared by the method described in Example 54 with the title compound of Example 2 and (S)-3-hydroxytetrahydrofuran.

Example 59

Compound of Formula I, wherein A=—(C=O)—O—R$^1$, wherein R$^1$=

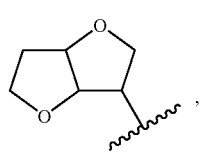

G=OH, L=absent, X and Y taken together with the carbon atoms to which they are attached are phenyl, W is absent, Z=thiophen-2-yl, j=3, m=s=1, and R$_5$=R$_6$=hydrogen.

The title compound is prepared by the method described in Example 54 with the title compound of Example 2 and

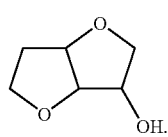

Example 60

Compound of Formula I, wherein A=—(C=O)—R$^1$, wherein R$^1$=cyclopentyl, G=OH, L=absent, X and Y taken together with the carbon atoms to which they are attached are phenyl, W is absent, Z=thiophen-2-yl, j=3, m=s=1, and R$_5$=R$_6$=hydrogen.

The title compound is prepared with the title compound from Example 2 in 4 ml of a 4M solution of HCl in dioxane and stirring the reaction mixture for 1 hour. The reaction residue is concentrated in vacuo. To this residue, 4 ml of THF and 0.045 mmol of TEA is added, the mixture is cooled to 0° C., to which is added 0.045 mmol of the cyclopentyl acid chloride. The resulting reaction mixture is stirred for 2 hours at 0° C. The reaction mixture is then extracted with EtOAc, washed with 1M sodium bicarbonate, water and brine, dried over MgSO$_4$ and concentrated to dryness in vacuo. The crude compound is purified by silica column and the ethyl ester is subsequently hydrolyzed by the procedure set forth in Example 2.

Example 61

Compound of Formula I, wherein A=—(C=O)—NH—R$^1$, wherein R$^1$=cyclooentyl, G=OH, L=absent, X and Y taken together with the carbon atoms to which they are attached are phenyl, W is absent, Z=thiophen-2-yl, j=3, m=s=1, and R$_5$=R$_5$=hydrogen The title compound is prepared with the title compound from Example 2 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isocyanate and the resulting reaction mixture is stirred at room temperature for 4 hours. The solution is then extracted with EtOAc, washed with 1% HCl, water and brine, dried over MgSO$_4$, and concentrated in vacuo to dryness. The crude compound is purified by silica column and the ethyl ester is subsequently hydrolyzed by the procedure set forth in Example 2.

Example 62

Compound of Formula I, wherein A=—(C=S)—NH—R$^1$, wherein R$^1$=cyclopentyl G=OH, L=absent, X and Y taken together with the carbon atoms to which they are attached are phenyl, W is absent, Z=thiophen-2-yl, j=3, m=s=1, and R$_5$=R$_6$=hydrogen The title compound is prepared with the title compound from Example 2 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isothiocyanate and the resulting reaction mixture is stirred at room temperature for 4 hours. The solution is then extracted with EtOAc, washed with 1% HCl, water and brine, dried over MgSO$_4$, and concentrated in vacuo to dryness. The crude compound is purified by silica column and the ethyl ester is subsequently hydrolyzed by the procedure set forth in Example 2.

Example 63

Compound of Formula I, wherein A=—S(O)$_2$—R$^1$, wherein R$^1$=cyclopentyl, G=OH, L=absent, X and Y taken together with the carbon atoms to which they are attached are phenyl, W is absent, Z=thiophen-2-yl, j=3, m=s=1, and R$_5$=R$_6$=hydrogen.

The title compound is prepared with the title compound from Example 2 in 4 ml of a 4M solution of HCl in dioxane and stirring for 1 hour. To the resulting concentrated reaction residue, which has been dissolved in 4 ml THF, is added 0.045 mmol of TEA, and cooled to 0° C. To the 0° C. solution is added 0.045 mmol of cyclopentyl sulfonyl chloride and the resulting reaction mixture is stirred at 0° C. for 2 hours. The solution is then extracted with EtOAc, washed with 1M sodium bicarbonate, water and brine, dried over MgSO$_4$, and concentrated in vacuo to dryness. The crude compound is purified by silica column and the ethyl ester is subsequently hydrolyzed by the procedure set forth in Example 2.

Example 64

Compound of Formula I, wherein A=—(C=O)—O—R$^1$, R$^1$=cyclopentyl, G=—O-phenethyl, L=absent, X and Y taken together with the carbon atoms to which they are attached are phenyl, W is absent, Z=thiophen-2-yl, j=3, m=s=1 and R$_5$=R$_6$=hydrogen.

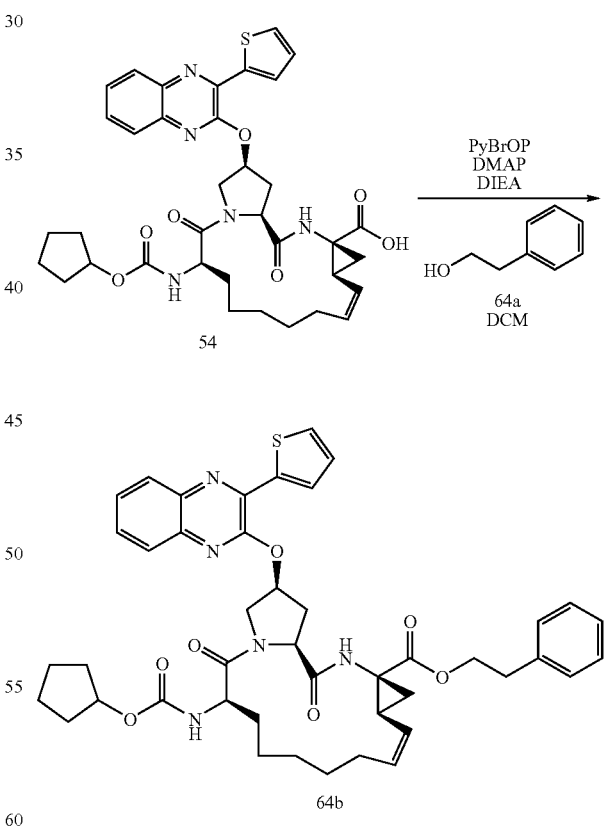

The title compound is prepared by adding to a solution of the title compound of Example 54 and phenethyl alcohol 64a in 0.5 ml DCM, is added 1.2 eq. PyBrOP, 4 eq. DIEA, and catalytic amount of DMAP at °0 C. The resulting reaction mixture is stirred for 1 hour at 0° C. and then warmed to room temperature over a period of 4–12 hours. The reaction mixture is purified by silica gel flash chromatography using different ratios of hexanes:EtOAc as elution phase (9:1→5:1→3:1→1:1) to afford the title compound isolated phenethyl ester 64b.

Other esters can be made using the same procedures.

Example 65

Compound of Formula I, wherein A=—(C=O)—O—$R^1$, $R^1$=cyclopentyl, G=—NH-phenethyl, L=absent, X and Y taken together with the carbon atoms to which they are attached are phenyl, W is absent, Z=thiophen-2-yl, j=3, m=s=1, and $R_5$=$R_6$=hydrogen.

Example 66

Compound of Formula I, wherein A=—(C=O)—O—$R^1$, $R^1$=cyclopentyl, G=—NHS(O)-phenethyl L=absent, X and Y taken together with the carbon atoms to which they are attached are phenyl, W is absent, Z=thiophen-2-yl, j=3, m=s=1, and $R_5$=$R_6$=hydrogen

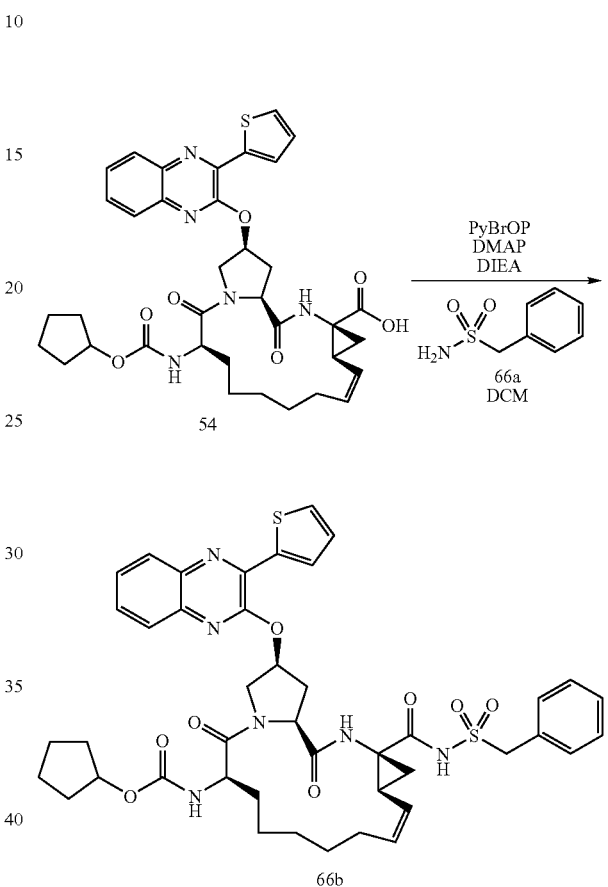

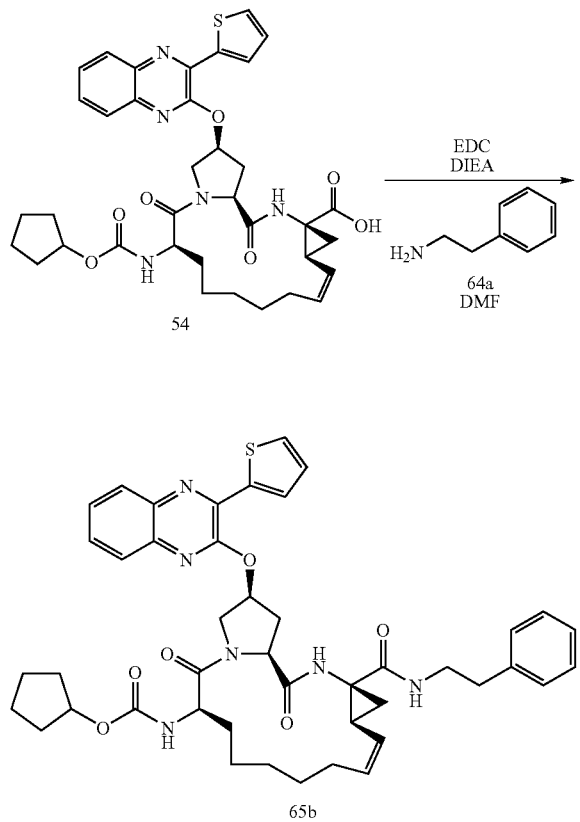

The title compound is prepared by adding to a solution of the title compound of Example 54 and α-toluenesulfonamide 66a (10 mg) in 0.5 ml DCM, is added 1.2 eq. PyBrOP, 4 eq. DIEA, and catalytic amount of DMAP at °0 C. The resulting reaction mixture is stirred for 1 hour and then allowed to warm to room temperature over a period of 4–12 hours. The reaction mixture is purified by silica gel flash chromatography using different ratios of hexanes:EtOAc as elution phase (9:1→5:1→3:1→1:1) to afford the title compound sulfonamide 66b. Other sulfonamides can be made via the same procedure.

Example 67

Compound of Formula I, wherein A=—(C=O)—O—$R^1$, $R^1$=cyclopentyl G=—(C=O)—OH, L=absent, X and Y taken together with the carbon atoms to which they are attached are phenyl, W is absent, Z=thiophen-2-yl, j=3 m=s=1, and $R_5$=$R_6$=hydrogen.

The title compound is prepared by adding to a solution of the title compound of Example 54 and phenethylamine 65a (0.05 ml) in 0.5 ml DMF, EDC (1.2 eq.) and DIEA (4 eq.) at °0 C. The resulting reaction mixture is stirred at 1 hour. Subsequently, the reaction is warmed to room temperature over a period of 4–12 hours. The reaction mixture is purified by silica gel flash chromatography using different ratios of hexanes:EtOAc as elution phase (9:1→5:1→3:1→1:1) to afford title compound phenethyl amide 65b. Other amides can be made via the same procedure.

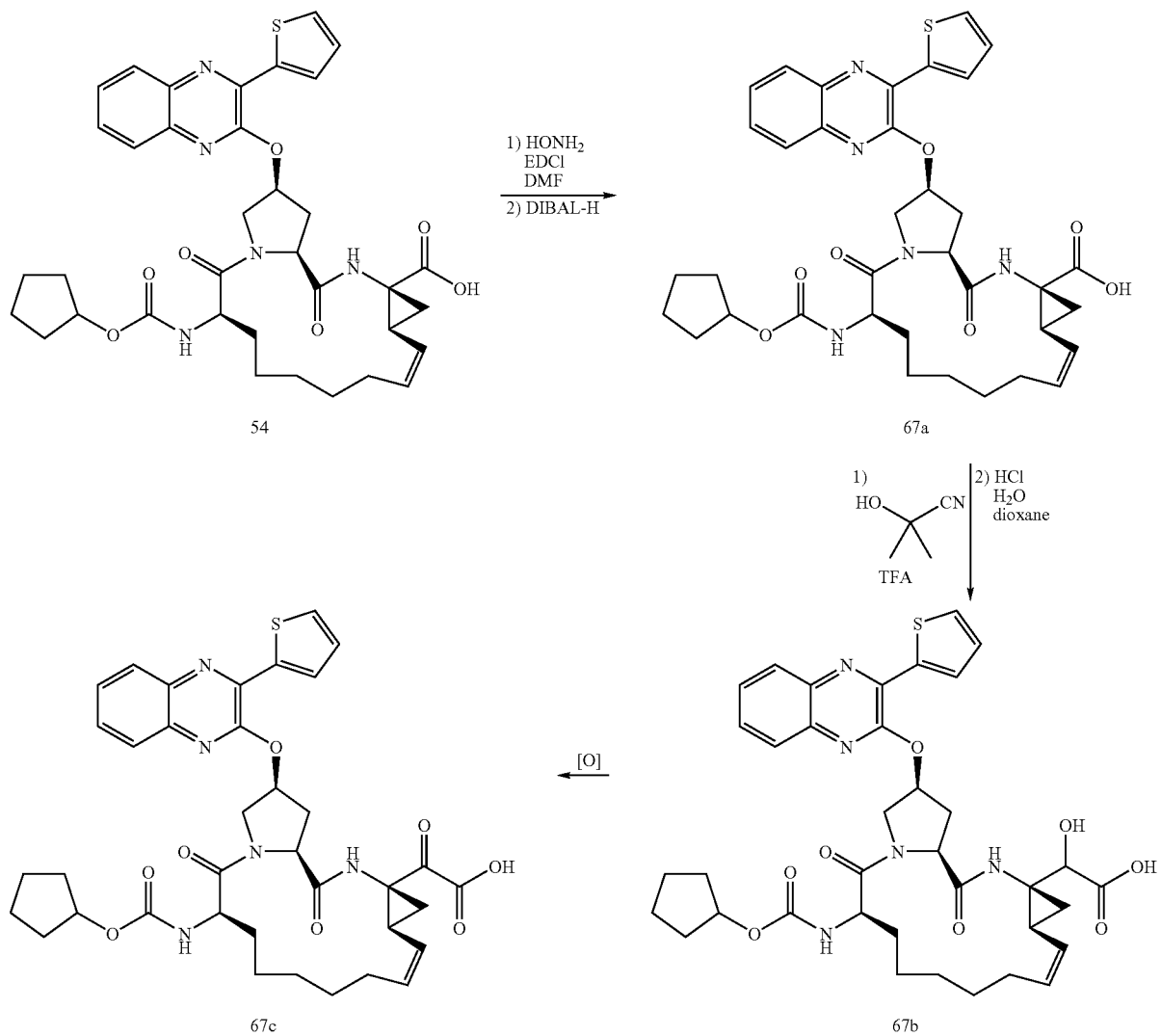

The title compound is prepared by adding to a solution of the title compound of Example 54 in 0.5 ml DMF, EDC (1.2 eq.) and DIEA (4 eq.) at °0 C. The resulting reaction mixture is stirred at 1 hour. Subsequently, the reaction is warmed to room temperature over a period of 4–12 hours. The reaction mixture is purified by silica gel flash chromatography to afford hydroxyamide. The hydroyamide is then treated with DIBAL-H at −78° C. in THF for 2 hours. The reaction mixture is then diluted with 8 ml EtOAc, washed with water and brine, dried over $Na_2SO_4$, and concentrated in vacuo to yield aldehyde 67a. To a solution of aldehyde 67a in 0.5 ml THF, is added α-hydroxy-α-methyl-propionitrile (0.1 ml) and catalytic amount TFA at °0C. The resulting reaction mixture is warmed from °0 C. to room temperature over a period of 4–12 hours followed by hydrolysis with concentrated hydrochloric acid in dioxane. The reaction is then extracted with EtOAc, and washed with water and brine to yield α-hydroxy compound 67b in its crude form. The crude compound 67b undergoes a Dess-Martin oxidation in THF (0.5 ml), providing the α-carbonyl compound 67c in crude form. The crude 67c is purified by silica gel flash chromatography using different ratios of hexanes:EtOAc as elution phase (9:1→5:1→3:1→1:1) to afford the title compound isolated keto acid 67c.

Example 68

Compound of Formula I, wherein A=—(C=O)—O—$R^1$, $R^1$=cyclopentyl, G=—(C=O)—O-phenethyl, L=absent, X and Y taken together with the carbon atoms to which they are attached are phenyl, W is absent, Z=thiophen-2-yl, j=3, m=s=1, and $R_5$=$R_6$=hydrogen The title compound is prepared with the title compound keto acid of Example 67 and phenethanol according to the procedure set forth in Example 64.

Example 69

Compound of Formula I, wherein A=—(C=O)—O—$R^1$, $R^1$=cyclopentyl, G=—(C=O)—NH-phenethyl, L=absent, X and Y taken together with the carbon atoms to which they are attached are phenyl, W is absent, Z=thiophen-2-yl, j=3, m=s=1, and $R_5$=$R_6$=hydrogen The title compound is prepared with the title compound keto acid of Example 67 and phenethyl amine according to the procedure set forth in Example 65.

Example 70

Compound of Formula I, wherein A=—(C=O)—O—$R^1$, $R^1$=cyclopentyl, G=—(C=O)—NH—S(O)$_2$-benzyl, L=absent, X and Y taken together with the carbon atoms to which they are attached are phenyl, W is absent, Z=thiophen-2-yl, j=3, m=s=1, and $R_5$=$R_6$=hydrogen.

The title compound is prepared with the title compound keto acid of Example 67 and α-toluenesulfonamide according to the procedure set forth in Example 66.

Example 71

Compound of Formula I, wherein A=tBOC, G=OH, L=—(C=O)CH$_2$—, X and Y taken together with the carbon atoms to which they are attached are phenyl, W is absent, Z=thiophen-2-yl, j=3, m=s=1, and $R_5$=$R_6$=hydrogen.

for 16 hours. The mixture then is diluted with ethyl acetate and the organic solution is washed with 0.5 N HCl (at 0° C.) and brine, dried and evaporated. The residue obtained is resolved via silica chromatography with a 35–40% ethyl acetate in hexanes eluent system to yield diester 71c.

71B. To a stirred solution of tetrakis (triphenylphosphine) Pd (0) in dry DMF is added the diester in DMF. The mixture is stirred at room temperature for 3.5 hours. The DMF is evaporated under reduced pressure and the residue diluted with EtOAc. The EtOAc solution is washed with 0.5N 0° C. HCl, brine, dried and evaporated. The residue is chromatographed on silica gel using 15% to 20% EtOAc in hexane as eluent to afford the methyl ester intermediate.

The methyl ester intermediate is then diluted with THF and water, LiOH.H$_2$O is added and the resulting mixture is stirred at room temperature for 25 hours, wherein the completion of the hydrolysis is monitored by TLC. The reaction mixture is concentrated under vacuum to remove a majority of the THF and further diluted with methylene chloride. The resulting solution is washed with 1 N HCl,

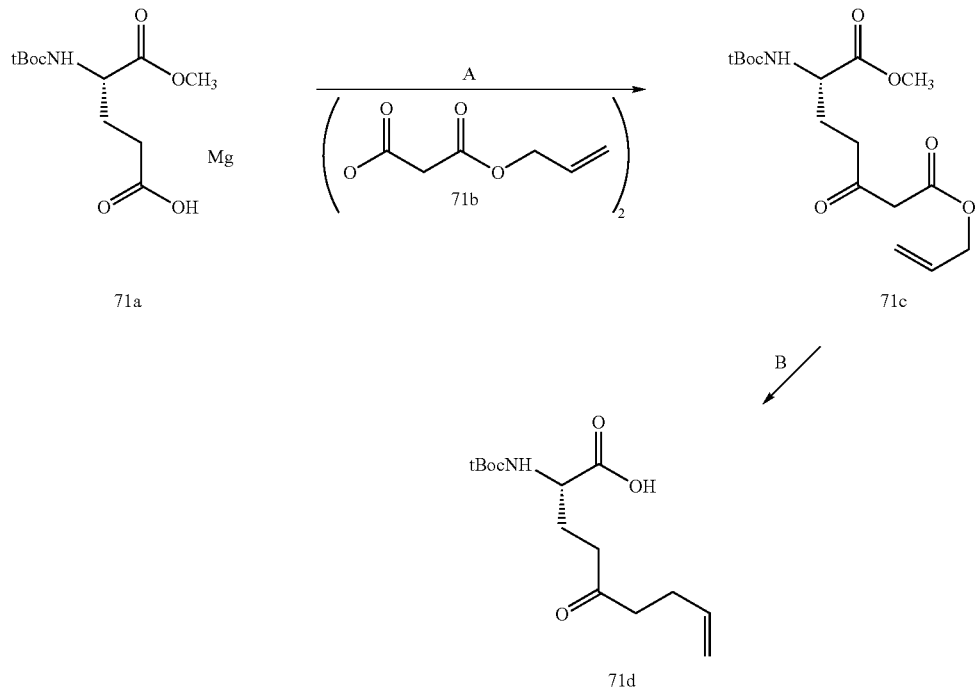

Synthesis of (2S)—N-Boc-amino-5-oxo-non-8-enoic acid

71A. The aforementioned amino acid is prepared by adding to a solution of monoallyl ester of malonic acid in dry THF under N$_2$ at −78° C., n-Bu$_2$Mg dropwise over a period of 5 min. The resulting suspension is then stirred at room temperature for 1 hour and evaporated to dryness. Solid Mg salt 71b, is dried under vacuum.

Glutamic acid derivative 71a is first mixed with 1,1'-carbonyldiimidazole in anhydrous THF and the mixture is stirred at room temperature for 1 hour to activate the free acid moiety. Subsequently, the activated glutamic acid derivative is cannulated into a solution of Mg salt 49b and the reaction mixture obtained is stirred at room temperature dried with anhydrous Na$_2$SO$_4$ and concentrated under vacuum. To remove minor impurities and excess Boc$_2$O, the crude product is purified via flash chromatography using a solvent gradient from 100% hexane →100% EtOAc as the eluent. (2S)—N-Boc-amino-5-oxo-non-8-enoic acid 71d is obtained. For further details of the preceding amino acid synthesis may be found in T. Tsuda et al., *J. Am. Chem. Soc.,* 1980, 102, 6381–6384 and WO 00/59929.

71C. Synthesis of Modified Cyclic Peptide Precursor Mesylate

The modified cyclic peptide precursor mesylate is prepared using the synthetic route detailed in Example 1 using (2S)—N-Boc-amino-5-oxo-non-8-enoic acid 71d in place of Boc-L-2-amino-8-nonenoic acid 1a followed by conversion to the corresponding mesylate via the method described in Example 2.

The title compound is prepared with the modified cyclic peptide precursor mesylate formed in 71C and 3-(thiophen-2-yl)-1H-quinoxylin-2-one by the Mitsunobu conditions elucidated in Example 2 followed by hydrolysis of the ethyl ester via the method set forth in Example 2.

Example 72

Compound of Formula I, wherein A=tBOC, G=OH, L=—CH(CH$_3$)CH$_2$—, X and Y taken together with the carbon atoms to which they are attached are phenyl, W is absent, Z=thiophen-2-yl, j=3, m=s=1, and R$_5$=R$_6$=hydrogen.

vacuum and then the mixture is extracted with ethyl acetate. The organic layer is further washed with water and brine, dried over anhydrous MgSO$_4$ and evaporated to dryness. The diol 72e is obtained in high purity after flash column chromatography using 1% ethanol in ethyl acetate as the eluent.

72D. To a solution of diol 72e in THF/H$_2$O (1:1) at 0° C., NaIO$_4$ is added and the reaction mixture is stirred at room temperature for 3.5 hours. A majority of the THF solvent is subsequently removed by evaporation under vacuum and the remaining mixture is extracted with EtOAc. The combined organic layers are further washed with 5% aqueous citric acid solution, 5% aq. NaHCO$_3$ and brine, then the organic phase is dried over MgSO$_4$ and evaporated to dryness under vacuum. Aldehyde intermediate 72f is used in the following step in its crude form.

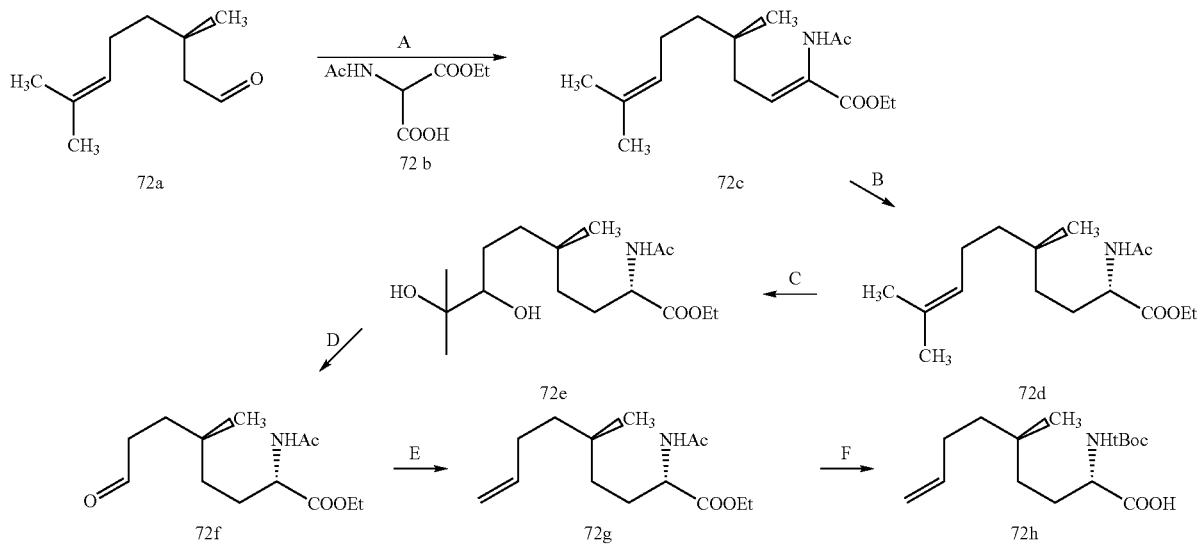

Synthesis of (2S,5R)—N-Boc-2-amino-5-methyl-non-8-enoic acid (72h)

72A. To solid ethyl 2-acetamidomalonate 72b is added (R)-(+)-citronellal 72a in a solution of pyridine over 1 min. The resulting solution is cooled in a 10° C. bath and acetic anhydride is added over 4 min. The resulting solution is stirred for 3 hours at room temperature and another portion of ethyl 2-acetamidomalonate 72a is added. The resulting mixture is stirred at room temperature for an additional 11 hours. Ice is then added and the solution is stirred for 1.5 hours, then the mixture is diluted with 250 ml water and extracted with two portions of ether. The organic phase is washed with 1N HCl, sat. NaHCO$_3$, dried Na$_2$SO$_4$, concentrated and purified by flash chromatography (40% EtOAc/hexane) to afford compound 72c.

72B. To a degassed solution of 72c in dry ethanol is added (S,S)-Et-DUPHOS Rh(COD)OTf. The mixture is subjected to 30 psi of hydrogen and stirred on a Parr shaker for 2 hours. The resulting mixture is evaporated to dryness to obtain the crude compound 72d, which is used in the subsequent step without purification.

72C. Compound 72d is dissolved in a mixture of tBuOH/acetone/H$_2$O (1:1:1) and placed in an ice bath (0° C.). NMMO and O$_s$O$_4$ is consecutively added and the reaction mixture is stirred at room temperature for 4 hours. A majority of the acetone is removed by evaporation under 72E. To a solution of Ph$_3$PCH$_3$Br in anhydrous toluene, KHMDS is added forming a suspension which is stirred at room temperature for 30 min. under N$_2$. After stirring, the suspension is cooled to 0° C., a solution of aldehyde intermediate 72f in THF is added, the mixture is warmed to room temperature, and stirred for 1 hour. A majority of the THF is evaporated under vacuum, EtOAc is added to the mixture and the organic phase is washed with water, 5% aq. NaHCO$_3$ and brine. The organic phase is then dried over MgSO$_4$ and evaporated to dryness under vacuum. Pure compound 72g is isolated after purification via flash chromatography on silica gel, using hexane:EtOAc (3:2) as the eluent.

72F. To a solution of crude 72g in THF, Boc$_2$O, and DMAP is added and the reaction mixture is heated to reflux for 2.5 hours. Subsequently, a majority of the THF is evaporated, the crude mixture is diluted with methylene chloride and washed with 1N HCl to remove DMAP. The organic layer is further extracted with saturated aq. NaHCO$_3$, dried with anyhrous Na$_2$SO$_4$ and concentrated under vacuum. The crude product is then diluted with THF and water, LiOH.H$_2$O is added and the resulting mixture is stirred at room temperature for 25 hours, wherein the completion of the hydrolysis is monitored by TLC. The reaction mixture is concentrated under vacuum to remove a majority of the THF and further diluted with methylene chloride. The resulting solution is washed with 1N HCl, dried with anhydrous Na$_2$SO$_4$ and concentrated under vacuum. To remove minor impurities and excess Boc$_2$O, the crude product is purified via flash chromatography using a solvent gradient from 100% hexane →100% EtOAc as the eluent. (2S, 5R)—N-Boc-2-amino-5-methyl-non-8-enoic acid 72 h is obtained. For further details of the preceding amino acid synthesis see WO 00/59929.

Synthesis of Modified Cyclic Peptide Precursor Mesylate

The modified cyclic peptide precursor mesylate is prepared using the synthetic route detailed in Example 1 using ((2S, 5R)—N-Boc-2-amino-5-methyl-non-8-enoic acid 72h in place of Boc-L-2-amino-8-nonenoic acid 1a followed by conversion to the corresponding mesylate via the method described in Example 2.

The title compound is prepared with the modified cyclic peptide precursor mesylate formed in 72G and 3-(thiophen-2-yl)-1H-quinoxylin-2-one by the Mitsunobu conditions elucidated in Example 2 followed by hydrolysis of the ethyl ester via the method set forth in Example 2.

Example 73

Compound of Formula I, wherein A=tBOC, G=OH, L=—O—, X and Y taken together with the carbon atoms to which they are attached are phenyl, W is absent, Z=thiophen-2-yl, j=3, m=s=1, R$_5$=methyl, and R$_6$=hydrogen.

Synthesis of N-Boc-O-allyl-(L)-threonine (73d)

73A. Boc-(L)-threonine 73a is partially dissolved in methylene chloride/methanol at 0° C. A solution of diazomethane in diethyl ether is added until yellow, indicating the presence of diazomethane. Upon evaporation of the solvents, crude methyl ester 73b is obtained.

73B. Intermediate 73b is dissolved in anhydrous diethyl ether, Ag$_2$O is added and freshly activated 4 Å molecular sieves. Finally, allyl iodide is added to the reaction mixture and is stirred at reflux. Two additional portions of allyl iodide are added to the reaction mixture after a period of 20 hours and 30 hours and stirring is continued for a total of 36 hours. The mixture is then filtered through celite and purified by flash chromatography on silica gel, using EtOAc/hexane (1:4) as the eluent, to afford compound 73c.

73C. Compound 73c is dissolved in a mixture of THF/MeOH/H$_2$O (2:1:1) and LiOH.H$_2$O is added. The solution is stirred at room temperature for 2 hours, and is acidified with 1 N HCl to pH ~3 before the solvents are removed under vacuum. The resulting crude compound 73d is obtained. For further details of the preceding synthesis see WO 00/59929, which is herein incorporated by reference in its entirety.

73D. Synthesis of Modified Cyclic Peptide Precursor Mesylate

The modified cyclic peptide precursor mesylate is prepared using the synthetic route detailed in Example 1 using N-Boc-O-allyl-(L)-threonine 73d in place of Boc-L-2-amino-8-nonenoic acid 1a followed by conversion to the corresponding mesylate via the method described in Example 2.

The title compound is prepared with the modified cyclic peptide precursor mesylate formed in 73D and 3-(thiophen-2-yl)-1H-quinoxylin-2-one by the Mitsunobu conditions elucidated in Example 2 followed by hydrolysis of the ethyl ester via the method set forth in Example 2.

Example 74

Compound of Formula I, wherein A=tBOC, G=OH, L=—S—, X and Y taken together with the carbon atoms to which they are attached are phenyl, W is absent, Z=thiophen-2-yl, j=3, m=s=1, R$_5$=methyl, and R$_6$=hydrogen.

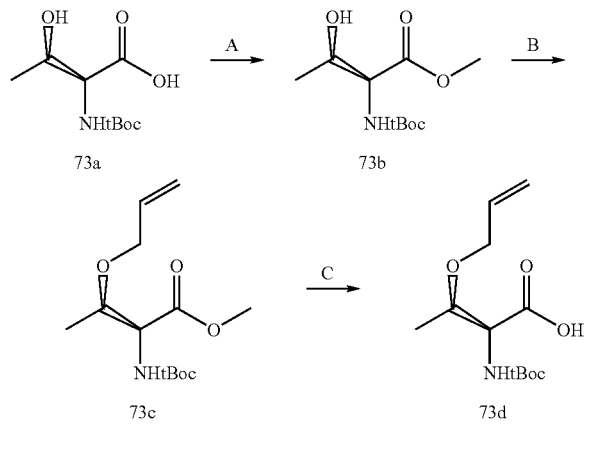

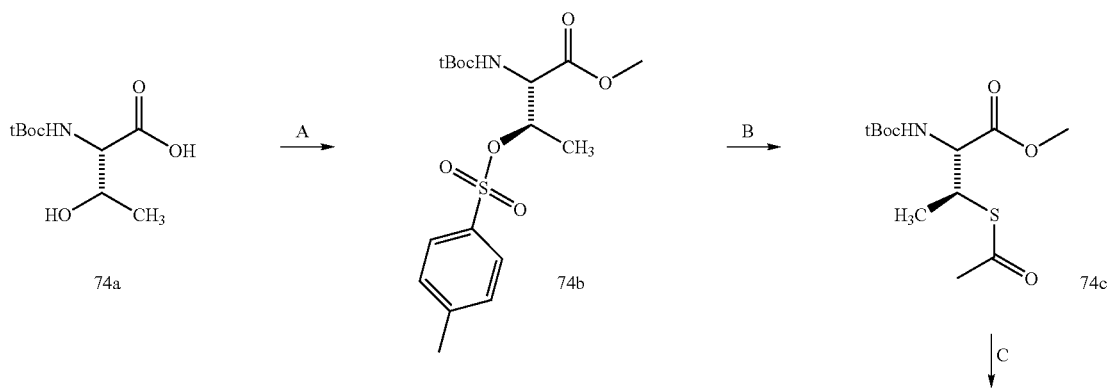

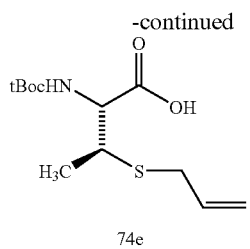 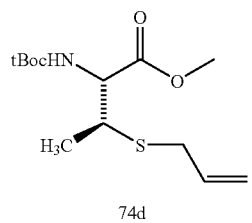

74e                            74d

Synthesis of (2S, 3S)—N-Boc-2 amino-3(mercaptoallyl)butanoic acid (74e)

74A. Compound 74a is dissolved in pyridine and the solution is cooled to 0° C. in an ice bath, tosyl chloride is added in small portions and the reaction mixture is partitioned between diethyl ether and H$_2$O. The ether layer is further washed with 0.2 N HCl and brine, dried over anhydrous MgSO$_4$, filtered and concentrated to dryness under vacuum. Purification of the crude material by flash chromatography on silica gel, using hexane/EtOAc (gradient from 8:2 to 7:3 ratio) as the eluent, leads to isolation of tosyl derivative 74b.

74B. To a solution of tosyl derivative 74b in anhydrous DMF, potassium thioacetate is added and the reaction mixture is stirred at room temperature for 24 hours. A majority of the DMF is then evaporated under vacuum and the remaining mixture is partitioned between EtOAc and H$_2$O. The aqueous layer is re-extracted with EtOAc, the combined organic layers are washed with brine, dried over anhydrous MgSO$_4$ and evaporated to dryness. Purification of the crude material by flash chromatography on silica gel using hexane/EtOAc (4:1 ratio) as the eluent, affords thioester 74c.

74C. To a solution of thioester 74c is H$_2$O/EtOH (3:5 ratio) and aqueous solution of 0.2M NaOH is added and the mixture is stirred at room temperature for 1.5 hours. Allyl iodide is then added and stirring is continued at room temperature for an additional 30 min. The reaction mixture is concentrated to half of its original volume and then extracted with EtOAc. The aqueous layer is acidified to pH ~3 with cold, aqueous 0.5N HCl and re-extracted with EtOAc. The combined organic layers are washed with brine, dried over anhydrous MgSO$_4$ and evaporated to dryness under vacuum. The crude reaction mixture contains at least four products; all of the products are isolated after flash chromatography on silica gel, using hexane/EtOAc (gradient from 9:1 to 3:1). The desired product 74d is the least polar compound.

74D. A solution of compound 74d in MeOH/H$_2$O (3:1) is mixed with aqueous NaOH (0.3 N) for 24 hours at room temperature and for 1 hour at 40° C. The reaction mixture is acidified with cold aqueous 0.5 N HCl, the MeOH is removed under vacuum and the remaining aqueous mixture is extracted with EtOAc. The organic phase is dried over MgSO$_4$ and evaporated to dryness in order to obtain compound 74e. For further details of the synthesis of amino acid 74e, see WO 00/59929, which is herein incorporated by reference in its entirety.

74E. Synthesis of Modified Cyclic Peptide Precursor Mesylate

The modified cyclic peptide precursor mesylate is prepared using the synthetic route detailed in Example 1 using (2S, 3S)—N-Boc-2 amino-3(mercaptoallyl)butanoic acid 74e in place of Boc-L-2-amino-8-nonenoic acid 1a followed by conversion to the corresponding mesylate via the method described in Example 2.

The title compound is prepared with the modified cyclic peptide precursor mesylate formed in 74E and 3-(thiophen-2-yl)-1H-quinoxylin-2-one by the Mitsunobu conditions elucidated in Example 2 followed by hydrolysis of the ethyl ester via the method set forth in Example 2.

Example 75

Compound of Formula I, wherein A=tBOC, G=OH, L=—S(O)—, X and Y taken together with the carbon atoms to which they are attached are phenyl, W is absent, Z=thiophen-2-yl, j=3, m=s=1, R$_5$=methyl, and R$_6$=hydrogen.

Formation of Modified Amino Acid

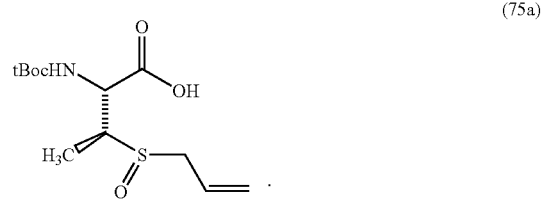

(75a)

75A. The modified amino acid is prepared by dissolving sodium metaperiodate (1.1 eq.) in water and cooled to 0° C. in an ice bath followed by adding dropwise a solution of compound 75d in dioxane. The resulting reaction mixture is stirred for one hour at 0° C. and 4 hours at 40° C. The reaction mixture is concentrated, water is added, and the mixture is extracted with methylene chloride twice. The combined organic layers are washed with water, brine, dried with anhydrous MgSO$_4$ and concentrated in vacuo. The methyl ester is then reduced via the method set forth in Example 74D to arrive upon the modified amino acid 75a. For further details concerning the sulfur oxidation reaction, see S. A. Burrage et al., *Tett. Lett.*, 1998, 39, 2831–2834, which is herein incorporated by reference in its entirety.

75B. Synthesis of Modified Cyclic Peptide Precursor Mesylate

The modified cyclic peptide precursor mesylate is prepared using the synthetic route detailed in Example 1 using the modified amino acid 75a in place of Boc-L-2-amino-8-nonenoic acid 1a followed by conversion to the corresponding mesylate via the method described in Example 2.

The title compound is prepared with the modified cyclic peptide precursor mesylate formed in 75B and 3-(thiophen-2-yl)-1H-quinoxylin-2-one by the Mitsunobu conditions elucidated in Example 2 followed by hydrolysis of the ethyl ester via the method set forth in Example 2.

Example 76

Compound of Formula I, wherein A=tBOC, G=OH, L=—S(O)$_2$—, X and Y taken together with the carbon atoms to which they are attached are phenyl, W is absent, Z=thiophen-2-yl, j=3, m=s=1, R$_5$=methyl, and R$_6$=hydrogen.

Formation of Modified Amino Acid

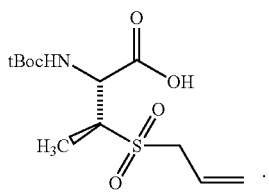

(76a)

76A. The modified amino acid is prepared by dissolving sodium metaperiodate (1.1 eq.) in water and cooled to 0° C. in an ice bath followed by adding dropwise a solution of compound 76d in dioxane. The resulting reaction mixture is stirred for one hour at 0° C. and 4 hours at 40° C. The reaction mixture is concentrated, water is added, and the mixture is extracted with methylene chloride twice. The combined organic layers are washed with water, brine, dried with anhydrous MgSO$_4$ and concentrated in vacuo. The methyl ester is then reduced via the method set forth in Example 74D to arrive upon the modified amino acid 76a. For further details concerning the sulfur oxidation reaction, see S. A. Burrage et al., *Tett. Lett.*, 1998, 39, 2831–2834.

76B. Synthesis of Modified Cyclic Peptide Precursor Mesylate

The modified cyclic peptide precursor mesylate is prepared using the synthetic route detailed in Example 1 using the modified amino acid 76a in place of Boc-L-2-amino-8-nonenoic acid 1a followed by conversion to the corresponding mesylate via the method described in Example 2.

The title compound is prepared with the modified cyclic peptide precursor mesylate formed in 76B and 3-(thiophen-2-yl)-1H-quinoxylin-2-one by the Mitsunobu conditions elucidated in Example 2 followed by hydrolysis of the ethyl ester via the method set forth in Example 2.

Example 77

Compound of Formula I, wherein A=tBOC, G=OH, L=—SCH$_2$CH$_2$—, X=Y=thiophen-3-yl, Z=hydrogen, j=0, m=s=1, and R$_5$=R$_6$=CH$_3$

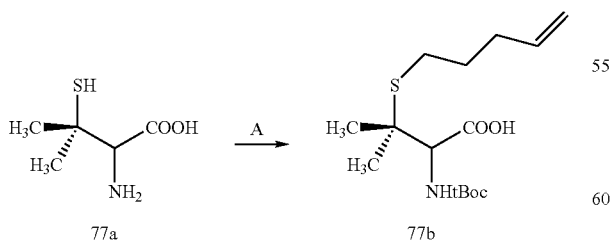

77A. Synthesis of (S)—N-Boc-2-amino-3-methyl-3(1-mercapto-4-butenyl)butanoic acid (77b)

L-Penicillamine 77a is dissolved in DMF/DMSO (5:1), subsequently, 4-bromopentene and CsOH.H$_2$O are added to the mixture and stirring is continued for an additional 12 hours. The DMF is subsequently removed in vacuo, the remaining mixture is diluted with 0.5 N HCl (at 0° C.) to adjust the pH to ~4–5 and then extracted with 2 portions of EtOAc. The organic phase is washed with brine (2×), dried over MgSO$_4$ and evaporated to dryness to afford the crude carboxylic acid 77a.

77B. Synthesis of Modified Cyclic Peptide Precursor Mesylate

The Modified Cyclic peptide precursor mesylate is prepared using the synthetic route detailed in Example 1 using the modified amino acid 77a in place of Boc-L-2-amino-8-nonenoic acid 1a followed by conversion to the corresponding mesylate via the method described in Example 2.

The title compound is prepared with the modified cyclic peptide precursor mesylate formed in 77B and 3-(thiophen-2-yl)-1H-quinoxylin-2-one by the Mitsunobu conditions elucidated in Example 2 followed by hydrolysis of the ethyl ester via the method set forth in Example 2.

Example 78

Compound of Formula I, wherein A=tBOC, G=OH, L=CF$_2$CH$_2$, X and Y taken together with the carbon atoms to which they are attached are phenyl, W is absent, Z=thiophen-2-yl, j=3, m=s=1, and R$_5$=R$_6$=hydrogen.

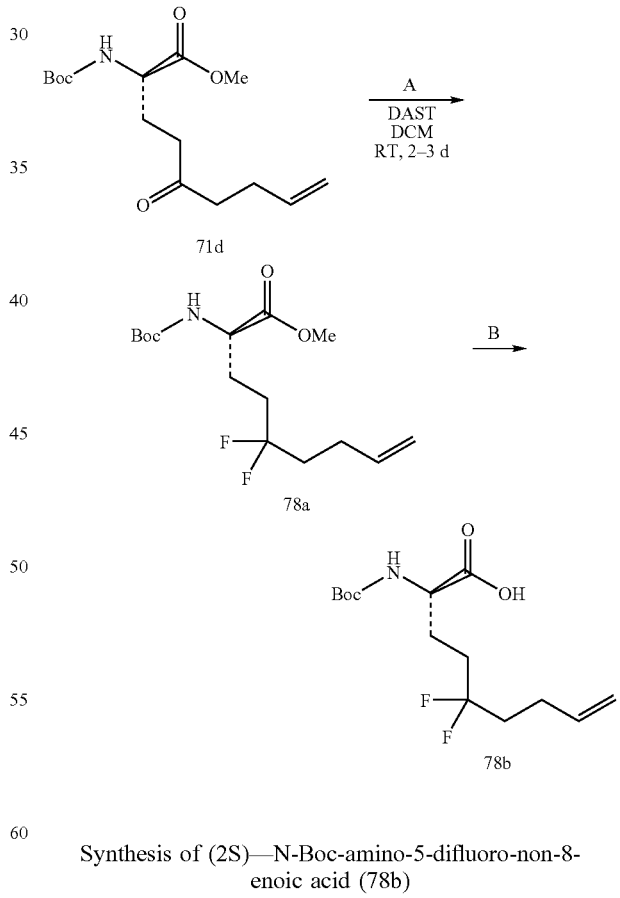

Synthesis of (2S)—N-Boc-amino-5-difluoro-non-8-enoic acid (78b)

78A. To a solution of the ketone compound 71d (0.30 g, 1 mmol) in 5 ml DCM, DAST (Diethylaminosulfurtrifluoride, 0.2 g, 1.2 eq) is added. The reaction is kept at room temperature over a period of 2–3 days. The solvent is evaporated and the residue is purified by silica gel flash chromatography using different ratios of hexanes:EtOAc as eluent (9:1→5:1→3:1→1:1), providing the isolated methyl ester 78a. For further details concerning the preceding synthesis, see Tius, Marcus A et al., *Tetrahedron*, 1993, 49, 16; 3291–3304, which is herein incorporated by reference in its entirety.

78B. Methyl ester 78a is dissolved in THF/MeOH/H$_2$O (2:1:1) and LiOH.H$_2$O is added. The solution is stirred at room temperature for 2 hours, and is then acidified with 1N HCl to pH ~3 before the solvents are removed in vacuo to afford the crude (2S)—N-Boc-amino-5-difluoro-non-8-enoic acid 78b.

78C. Synthesis of Modified Cyclic Peptide Precursor Mesylate

The modified cyclic peptide precursor mesylate is prepared using the synthetic route detailed in Example 1 using crude (2S)—N-Boc-amino-5-difluoro-non-8-enoic acid 78b in place of Boc-L-2-amino-8-nonenoic acid 1a followed by conversion to the corresponding mesylate via the method described in Example 2.

The title compound is prepared with the modified cyclic peptide precursor mesylate formed in 78C and 3-(thiophen-2-yl)-1H-quinoxylin-2-one by the Mitsunobu conditions elucidated in Example 2 followed by hydrolysis of the ethyl ester via the method set forth in Example 2.

Example 79

Compound of Formula I, wherein A=tBOC, G=OH, L=—CHFCH$_2$—, X and Y taken together with the carbon atoms to which they are attached are phenyl, W is absent, Z=thiophen-2-yl, j=3, m=s=1 and R$_5$=R$_6$=hydrogen.

stirred at room temperature over a period of 2–6 hours, and then quenched by 1M ammonium chloride and extracted with EtOAc (30 ml). The solvent is evaporated and the crude hydroxy compound 79a is obtained.

79B. The hydroxy compound 79a is dissolved in 5 ml DCM to which DAST (0.2 g, 1.2 eq) is added and stirred at −45° C. for 1 hour. The reaction mixture is then warmed to room temperature and stirred over a period of 2–3 days. The solvent is evaporated and the residue is purified by silica gel flash chromatography using different ratios of hexanes: EtOAc as eluent (9:1→5:1→3:1→1:1), providing the isolated monofluoro compound methyl ester 79b. For further details concerning the preceding reaction, see Buist, Peter H et al., *Tetrahedron Lett.*, 1987, 28, 3891–3894, which is herein incorporated by reference in its entirety.

79C. Methyl ester 79b is dissolved in THF/MeOH/H$_2$O (2:1:1) and LiOH.H$_2$O is added. The solution is stirred at room temperature for 2 hours, and is then acidified with 1N HCl to pH ~3 before the solvents are removed in vacuo to afford the crude (2S)—N-Boc-amino-5-difluoro-non-8-enoic acid 79c.

79D. Synthesis of Modified Cyclic Peptide Precursor Mesylate

The modified cyclic peptide precursor mesylate is prepared using the synthetic route detailed in Example 1 using crude (2S)—N-Boc-amino-5-monofluoro-non-8-enoic acid 79b in place of Boc-L-2-amino-8-nonenoic acid 1a followed by conversion to the corresponding mesylate via the method described in Example 2.

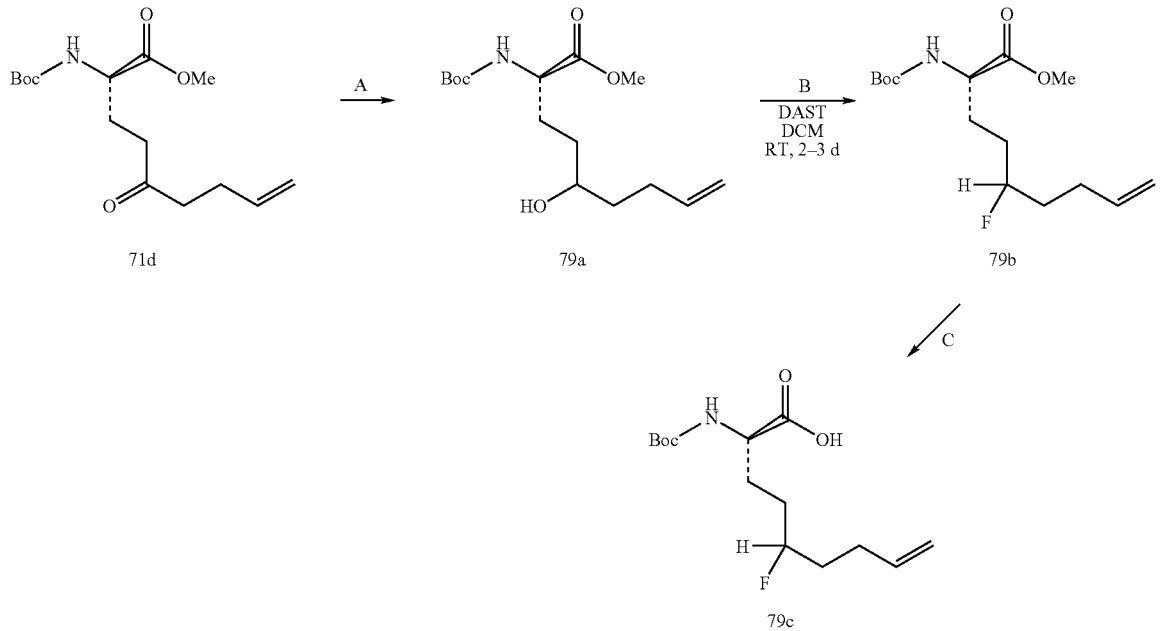

Synthesis of (2S)—N-Boc-amino-5-fluoro-non-8-enoic acid (79c)

79A. To a solution of the ketone compound 71d in 5 ml methanol, NaBH$_4$ (2.2 eq) is added. The reaction mixture is The title compound is prepared with the modified cyclic peptide precursor mesylate formed in 79C and 3-(thiophen-2-yl)-1H-quinoxylin-2-one by the Mitsunobu conditions elucidated in Example 2 followed by hydrolysis of the ethyl ester via the method set forth in Example 2.

Example 80

Compound of Formula II, wherein A=tBOC, G=OH, L=absent, X and Y taken together with the carbon atoms to which they are attached are phenyl, W is absent, Z=thiophen-2-yl, j=3, m=s=1, and $R_5=R_6$=hydrogen.

80A. The saturated cyclic peptide precursor is prepared by catalytic reduction of the cyclic peptide precursor of Example 1 with Pd/C in MeOH in the presence of $H_2$.

The title compound is prepared with the saturated cyclic peptide precursor mesylate formed in 80A and 3-(thiophen-2-yl)-1H-quinoxylin-2-one by the Mitsunobu conditions elucidated in Example 2 followed by hydrolysis of the ethyl ester via the method set forth in Example 2.

The compounds of the present invention exhibit potent inhibitory properties against the HCV NS3 protease. The following examples elucidate assays in which the compounds of the present invention are tested for anti-HCV effects.

Example 81

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence was measured with a Molecular Devices Fluoromax (or equivalent) using an excitation wavelength of 355 nm and an emission wavelength of 485 nm.

The assay is run in Corning white half-area 96-well plates (VWR 29444-312 [Corning 3693]) with full-length NS3 HCV protease 1b tethered with NS4A cofactor (final enzyme concentration 1 to 15 nM). The assay buffer is complemented with 10 µM NS4A cofactor Pep 4A (Anaspec 25336 or in-house, MW 1424.8). RET S1 (Ac-Asp-Glu-Asp (EDANS)-Glu-Glu-Abu-[COO]Ala-Ser-Lys-(DABCYL)-$NH_2$, AnaSpec 22991, MW 1548.6) is used as the fluorogenic peptide substrate. The assay buffer contained 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, [−20° C.] and HCV Inh 2 (Anaspec 25346, MW 913.1) Ac-Asp-Glu-Dif-Cha-Cys-OH, were used as reference compounds.

IC50 values were calculated using XLFit in ActivityBase (IDBS) using equation 205: $y=A+((B-A)/(1+((C/x)^D)))$.

Example 82

Cell-Based Replicon Assay

Quantification of HCV Replicon RNA in Cell Lines (HCV Cell Based Assay)

Cell lines, including Huh-11-7 or Huh 9-13, harboring HCV replicons (Lohmann, et al Science 285:110–113, 1999) are seeded at $5\times10^3$ cells/well in 96 well plates and fed media containing DMEM (high glucose), 10% fetal calf serum, penicillin-streptomycin and non-essential amino acids. Cells are incubated in a 5% $CO_2$ incubator at 37° C. At the end of the incubation period, total RNA is extracted and purified from cells using Qiagen Rneasy 96 Kit (Catalog No. 74182). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the Taq-Man One-Step RT-PCR Master Mix Kit (Applied Biosystems catalog no. 4309169). The nucleotide sequences of the RT-PCR primers, which are located in the NS5B region of the HCV genome, are the following:

```
HCV Forward primer "RBNS5bfor"
5'GCTGCGGCCTGTCGAGCT:

HCV Reverse primer "RBNS5Brev":
5'CAAGGTCGTCTCCGCATAC
```

Detection of the RT-PCR product was accomplished using the Applied Biosystems (ABI) Prism 7700 Sequence Detection System (SDS) that detects the fluorescence that is emitted when the probe, which is labeled with a fluorescence reporter dye and a quencher dye, is processed during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

```
5' FAM-CGAAGCTCCAGGACTGCACGATGCT-TAMRA
```

FAM=Fluorescence reporter dye.
TAMRA:=Quencher dye.

The RT reaction is performed at 48° C. for 30 minutes followed by PCR. Thermal cycler parameters used for the PCR reaction on the ABI Prism 7700 Sequence Detection System were: one cycle at 95° C., 10 minutes followed by 35 cycles each of which included one incubation at 95° C. for 15 seconds and a second incubation for 60° C. for 1 minute.

To normalize the data to an internal control molecule within the cellular RNA, RT-PCR is performed on the cellular messenger RNA glyceraldehydes-3-phosphate dehydrogenase (GAPDH). The GAPDH copy number is very stable in the cell lines used. GAPDH RT-PCR is performed on the same exact RNA sample from which the HCV copy number is determined. The GAPDH primers and probes, as well as the standards with which to determine copy number, are contained in the ABI Pre-Developed TaqMan Assay Kit (catalog no. 431 0884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines The effect of a specific anti-viral compound on HCV replicon RNA levels in Huh-11-7 or 9–13 cells was determined by comparing the amount of HCV RNA normalized to GAPDH (e.g. the ratio of HCV/GAPDH) in the cells exposed to compound versus cells exposed to the 0% inhibition and the 100% inhibition controls. Specifically, cells were seeded at 5×10³ cells/well in a 96 well plate and were incubated either with: 1) media containing 1% DMSO (0% inhibition control), 2) 100 international units, IU/ml Interferon-alpha 2b in media/1% DMSO or 3) media/1% DMSO containing a fixed concentration of compound. 96 well plates as described above were then incubated at 37° C. for 3 days (primary screening assay) or 4 days (IC50 determination). Percent inhibition was defined as:

% Inhibition=[100−((S−C2)/C1−C2))]×100 where

S=the ratio of HCV RNA copy number/GAPDH RNA copy number in the sample;

C1=the ratio of HCV RNA copy number/GAPDH RNA copy number in the 0% inhibition control (media/1% DMSO); and C2=the ratio of HCV RNA copy number/GAPDH RNA copy number in the 100% inhibition control (100 IU/ml Interferon-alpha 2b).

The dose-response curve of the inhibitor was generated by adding compound in serial, three-fold dilutions over three logs to wells starting with the highest concentration of a specific compound at 10 uM and ending with the lowest concentration of 0.01 uM. Further dilution series (1 uM to 0.001 uM for example) was performed if the IC50 value was not in the linear range of the curve. IC50 was determined based on the IDBS Activity Base program using Microsoft Excel "XL Fit" in which A=100% inhibition value (100 IU/ml Interferon-alpha 2b), B=0% inhibition control value (media/1% DMSO) and C=midpoint of the curve as defined as C=(B−A/2)+A. A, B and C values are expressed as the ratio of HCV RNA/GAPDH RNA as determined for each sample in each well of a 96 well plate as described above. For each plate the average of 4 wells were used to define the 100% and 0% inhibition values.

Although the invention has been described with respect to various preferred embodiments, it is not intended to be limited thereto, but rather those skilled in the art will recognize that variations and modifications may be made therein which are within the spirit of the invention and the scope of the appended claims.

The invention claimed is:

1. A compound of Formula I or II:

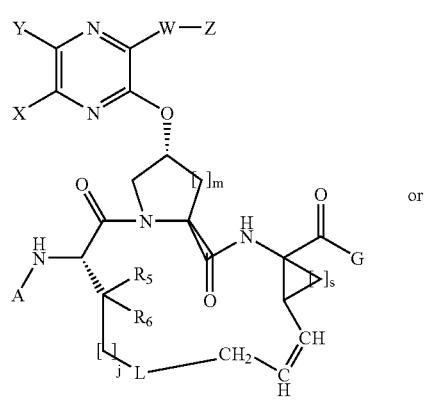

(I)

or

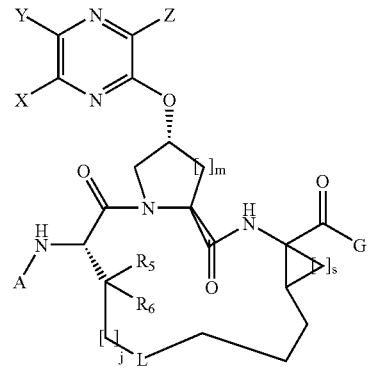

(II)

A is independently selected from hydrogen; —(C=O)—O—$R_1$, —(C=O)—$R_2$, —C(=O)—NH—$R_2$, —C(=S)—NH—$R_2$, or —S(O)$_2$—$R_2$;

G is independently selected from —OH, —O—($C_1$–$C_{12}$ alkyl), —NHS(O)$_2$—$R_1$, —(C=O)—$R_2$,; —(C=O)—O—$R_1$, or —(C=O)—NH—$R_2$;

L is independently selected from —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, or —CF$_2$CH$_2$—;

X and Y taken together with the carbon atoms to which they are attached form a cyclic moiety selected from aryl, substituted aryl, heteroaryl, or substituted heteroaryl;

W is absent, or independently selected from —O—, —S—, —NH—, —C(O)NR$_1$— or —NR$_1$—;

Z is independently selected from hydrogen; —CN, —SCN, —NCO, —NCS, —NHNH$_2$, —N$_3$, halogen, —R$_4$, —C$_3$–C$_{12}$ cycloalkyl, substituted —C$_3$–C$_{12}$ cycloalkyl, aryl, substituted aryl, heteroaryl, substituted heteroaryl, heterocycloalkyl, substituted heterocycloalkyl, and —NH—N=CH(R$_1$);

each R$_1$ is independently selected from hydrogen, C$_1$–C$_6$ alkyl, substituted C$_1$–C$_6$ alkyl, C$_1$–C$_6$ alkenyl, substituted C$_1$–C$_6$ alkenyl, C$_1$–C$_6$ alkynyl, substituted C$_1$–C$_6$ alkynyl, C$_3$–C$_{12}$ cycloalkyl, substituted C$_3$–C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;

each R$_2$ is independently selected from hydrogen, C$_1$–C$_6$ alkyl, C$_1$–C$_6$ alkyl, substituted C$_1$–C$_6$ alkyl, C$_1$–C$_6$ alkenyl, substituted C$_1$–C$_6$ alkenyl, C$_1$–C$_6$ alkynyl, substituted C$_1$–C$_6$ alkynyl, C$_3$–C$_{12}$ cycloalkyl, substituted C$_3$–C$_{12}$ cycloalkyl, alkylamino, dialkylamino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;

each R$_4$ is independently selected from:

(i) —C$_1$–C$_6$ alkyl containing 0, 1, 2, or 3 heteroatoms selected from O, S, or N, optionally substituted with one or more substituent selected from halogen, aryl, substituted aryl, heteroaryl, or substituted heteroaryl;

(ii) —C$_2$–C$_6$ alkenyl containing 0, 1, 2, or 3 heteroatoms selected from O, S, or N, optionally substituted with one or more substituent selected from halogen, aryl, substituted aryl, heteroaryl, or substituted heteroaryl; or (iii) —$C_2$–$C_6$ alkynyl containing 0, 1, 2, or 3 heteroatoms selected from O, S, or N, optionally substituted with one or more substituent selected from halogen, aryl, substituted aryl, heteroaryl, or substituted heteroaryl;

$R_5$ and $R_6$ are each independently selected from hydrogen or methyl;

each $R_7$ and $R_8$ is independently selected from:

(i) —$C_1$–$C_6$ alkyl containing 0, 1, 2, or 3 heteroatoms selected from O, S, or N, optionally substituted with one or more substituent selected from halogen, aryl, substituted aryl, heteroaryl, or substituted heteroaryl;

(ii) —$C_2$–$C_6$ alkenyl containing 0, 1, 2, or 3 hetematorns selected from O, S, or N, optionally substituted with one or more substituent selected from halogen, aryl, substituted aryl, heteroaryl, or substituted heteroaryl; or (iii) —$C_2$–$C_6$ alkynyl containing 0, 1, 2, or 3 heteroatoms selected from O, S, or N, optionally substituted with one or more substituent selected from halogen, aryl, substituted aryl, heteroaryl, or substituted heteroaryl;

j=0, 1, 2, 3, or 4;

m=0, 1, or 2;

s=0, 1 or 2;

wherein each substituted alkyl, substituted alkynyl, substituted alkynyl, substituted aryl, substituted arylalkyl, substituted heteroaryl, substituted $C_3$–$C_{12}$-cycloalkyl, substituted heterocycloalkyl, and substituted heteroarylalkyl may independently replace one, two or three of the hydrogen atoms thereon with F, Cl, Br, I, OH, $NO_2$, CN, $C_1$–$C_6$-alkyl-OH, C(O)—$C_1$–$C_6$-alkyl, $OCH_2$—$C_3$–$C_{12}$-cycloalkyl, C(O)H, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)H, NHC(O)—$C_1$–$C_6$-alkyl, NHC(O)-aryl, NHC(O)-heteroaxyl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2$NH—$C_1$–$C_6$-alkyl, $SO_2$NH-aryl, $SO_2$NH-heteroaryl, $C_1$–$C_6$-alkyl, $C_3$–$C_{12}$-cycloalkyl, $CF_3$, $CH_2CF_3$, $CHCl_2$, $CH_2NH_2$, $CH_2SO_2CH_3$, $C_1$–$C_6$ alkyl, halo alkyl, $C_3$–$C_{12}$ cycloalkyl, substituted $C_3$–$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, di-$C_1$–$C_3$-alkylamino, thio, aryl-thio, heteroarylthio, benzyl-thio, $C_1$–$C_6$-alkyl-thio, or methylthiomethyl.

2. The compound of claim 1, wherein the compound is of Formula III:

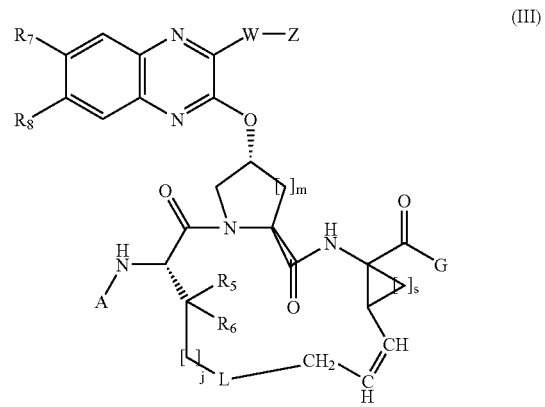

wherein $R_7$ and $R_8$ are independently selected from $R_4$ as defined in claim 1.

3. The compound of claim 1, wherein the compound is of Formula IV:

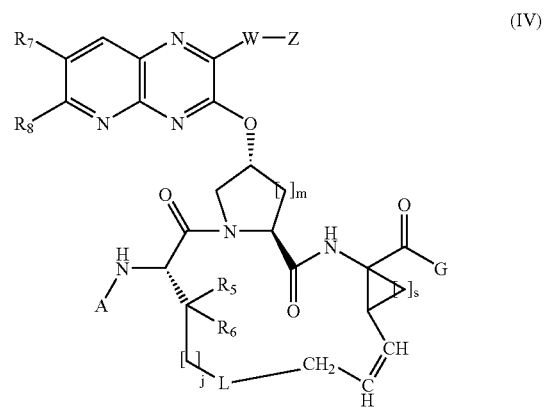

wherein $R_7$ and $R_8$ are independently selected from $R_4$ as defined in claim 1.

4. A compound according to any one of claims 1–3, wherein W is absent and Z is thiophenyl.

5. A compound according to any one of claims 1–3, wherein W is —CH=CH— and Z is thiophenyl.

6. A compound according to claim 1 which is selected from:

Compound of Formula I, wherein A=tBOC, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=tBOC, G=OH, L=absent, X and Y taken together with the carbon atoms to which they are attached are phenyl, W is absent, Z=2-(formamido)-thiazol-4-yl, j=3, m=s=1, and $R_5$=$R_6$=hydrogen;

Compound of Formula I, wherein A=tBOC, G=OH, L=absent, X and Y taken together with the carbon atoms to which they are attached are phenyl, W is absent, Z=ethyl, j=3, m=s=1, and $R_5$=$R_6$=hydrogen;

Compound of Formula I, wherein A=tBOC, G=OH, L=absent, X and Y taken together with the carbon atoms to which they are attached are phenyl, W is absent, Z=phenyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=4-methoxyphenyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=4-ethoxyphenyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=5-bromothiophen-2-yl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=2-pyrid-3-yl ethylenyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=3,4-Dimethoxy-phenyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=2-thiophen-2-yl ethylenyl, j=3, m=s=1, and $R_5=R_6$=hydrogen;

Compound of Formula I, wherein A=tBOC, G=OH, L=absent, X and Y taken together with the carbon atoms to which they are attached are phenyl, Z=indole-2-yl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=1H-indol-3-yl methyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=furan-2-yl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=1H-benzoimidazol-2-yl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=1H-imidazol-2-ylmethyl, j=3, m=s=1, and $R_5=R_6$=hydrogen;

Compound of Formula I, wherein A=tBOC, G=OEt, L=absent, X and Y taken together with the carbon atoms to which they are attached are phenyl, W is absent, Z=chloro, j=3, m=s=1, and $R_5=R_6$=hydrogen;

Compound of Formula I, wherein A=tBOC, G=OH, L=absent, X and Y taken together with the carbon atoms to which they are attached are phenyl, Z=thiophen-3-yl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=2-pyrid-3-yl acetylenyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=2,3-dihydrobenzofuran-5-yl, j=3, m=s=1, and $R_5=R_6$=hydrogen;

Compound of Formula I, wherein A=tBOC, G=OH, L=absent, X and Y taken together with the carbon atoms to which they are attached are phenyl, W=—NH—, Z=propargyl, j=3, m=s=1, and $R_5=R_6$=hydrogen;

Compound of Formula I, wherein A=tBOC, G=OH, L=absent, X and Y taken together with the carbon atoms to which they are attached are phenyl, W=—N(ethyl)-, Z=benzyl, j=3, m=s=1, and $R_5=R_6$=hydrogen;

Compound of Formula I, wherein A=tBOC, G=OH, L=absent, X and Y taken together with the carbon atoms to which they are attached are phenyl, W=—NH—, Z=pyrid-3-yl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=tetrazolyl, j=3, m=s=1, and $R_5=R_6$=hydrogen;

Compound of Formula I, wherein A=tBOC, G=OH, L=absent, X and Y taken together with the carbon atoms to which they are attached are phenyl, W is absent, Z=morpholino, j=3, m=s=1, and $R_5=R_6$=hydrogen;

Compound of Formula I, wherein A=tBOC, G=OH, L=absent, X and Y taken together with the carbon atoms to which they are attached are phenyl, W=—O—, Z=thiophen-3-yl-methyl, j=3, m=s=1, and $R_5=R_6$=hydrogen;

Compound of Formula I, wherein A=tBOC, G=OH, L=absent, X and Y taken together with the carbon atoms to which they are attached are

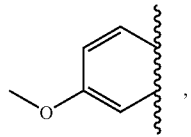

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

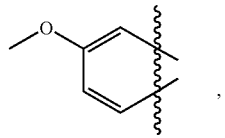

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

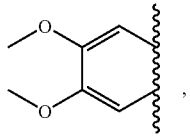,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

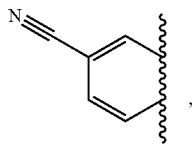,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

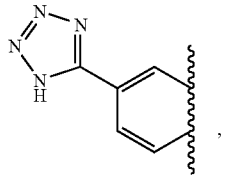,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

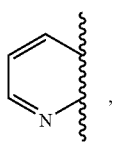,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

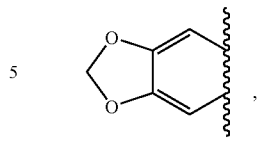,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

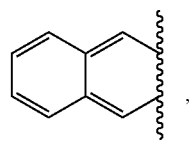,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

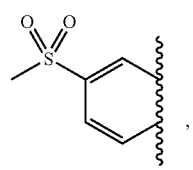,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

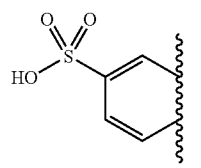,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

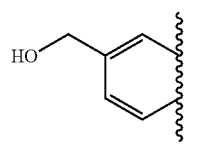,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

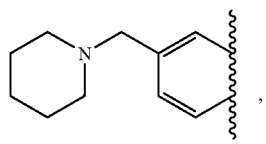,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

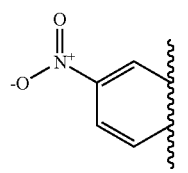,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

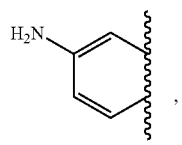,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

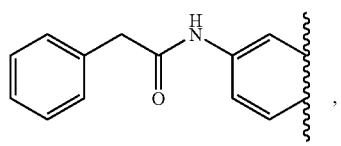,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

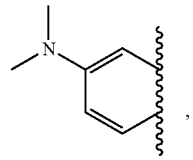,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

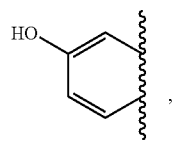,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

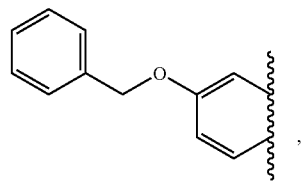,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

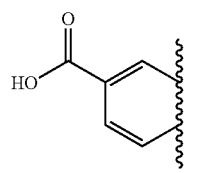,

W is absent, Z=thiophen-2-yl, j=3, m=s=1, and R$_5$=R$_6$=hydrogen;

Compound of Formula I, wherein A=tBOC, G=OH, L=absent, X and Y taken together with the carbon atoms to which they are attached are

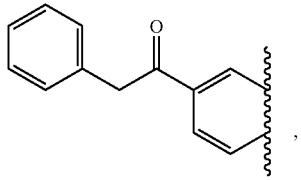,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

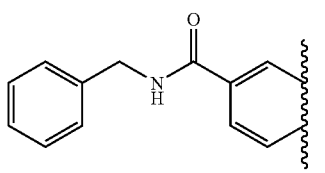,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

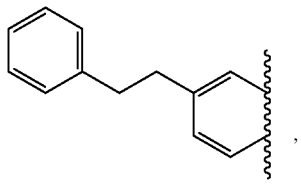,

W is absent, Z=thiophen-2-yl, j=3, m=s=1, and $R_5=R_6$=hydrogen;

Compound of Formula I, wherein A=tBOC, G=OEt, L=absent, X and Y taken together with the carbon atoms to which they are attached are

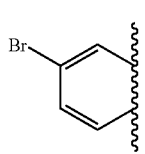,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

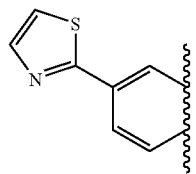,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

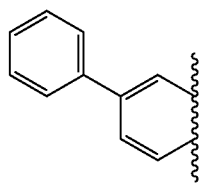,

W is absent, Z=thiophen-2-yl, j=3, m=s=1, and $R_5=R_6$=hydrogen;

Compound of Formula I, wherein A=tBOC, G=OH, L=absent, X and Y taken together with the carbon atoms to which they are attached are

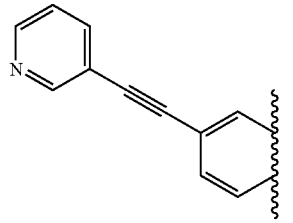,

W is absent, Z=thiophen-2-yl, j=3, m=s=1, $R_5=R_6$=hydrogen;

Compound of Formula I, wherein A=tBOC, G=OH, L=absent, X and Y taken together with the carbon atoms to which they are attached are

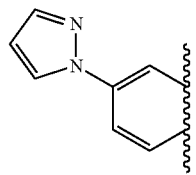,

W is absent, Z=thiophen-2-yl, j=3, m=s=1, $R_5=R_6$=hydrogen;

Compound of Formula I, wherein A=—(C=O)—O—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, wherein $R^1$=cyclobutyl, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, wherein $R^1$=cyclohexyl, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, wherein $R^1$=

[structure: tetrahydrofuran-3-yl]

G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, wherein $R^1$=

[structure: dihydrofuran]

G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, wherein $R^1$=

[structure: bicyclic furan]

G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—NH—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=S)—NH—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—S(O)$_2$—$R^1$, wherein $R^1$=cyclopentyl, G=OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, $R^1$=cyclopentyl, G=—O-phenethyl, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, $R^1$=cyclopentyl, G=—NH-phenethyl, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, $R^1$=cyclopentyl, G=—NHS(O)$_2$-phenethyl L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, $R^1$=cyclopentyl, G=—(C=O)—OH, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, $R^1$=cyclopentyl, G=—(C=O)—O-phenethyl, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, $R^1$=cyclopentyl, G=—(C=O)—NH-phenethyl, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=—(C=O)—O—$R^1$, $R^1$=cyclopentyl, G=—(C=O)—NH—S(O)$_2$-benzyl, L=absent, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=tBOC, G=OH, L=—(C=O)CH$_2$—, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=tBOC, G=OH, L=—CH(CH$_3$)CH$_2$—, X and Y taken together with the carbon atoms to which they are attached are phenyl, W is absent, Z=thiophen-2-yl, j=3, m=s=1, and $R_5$=$R_6$=hydrogen;

Compound of Formula I, wherein A=tBOC, G=OH, L=—O—, X and Y taken together with the carbon atoms to which they are attached are phenyl, W is absent, Z=thiophen-2-yl, j=3, m=s=1, $R_5$=methyl, and $R_6$=hydrogen;

Compound of Formula I, wherein A=tBOC, G=OH, L=—S—, X and Y taken together with the carbon atoms to which they are attached are phenyl, W is absent, Z=thiophen-2-yl, j=3, m=s=1, $R_5$=methyl, and $R_6$=hydrogen;

Compound of Formula I, wherein A=tBOC, G=OH, L=—S(O)—, X and Y taken together with the carbon atoms to which they are attached are phenyl, W is absent, Z=thiophen-2-yl, j=3, m=s=1, $R_5$=methyl, and $R_6$=hydrogen;

Compound of Formula I, wherein A=tBOC, G=OH, L=—S(O)$_2$, X and Y taken together with the carbon atoms to which they are attached are phenyl, W is absent, Z=thiophen-2-yl, j=3, m=s=1, $R_5$=methyl, and $R_6$=hydrogen;

Compound of Formula I, wherein A=tBOC, G=OH, L=—SCH$_2$CH$_2$—, X and Y taken together with the carbon atoms to which they are attached are phenyl, W is absent, Z=thiophen-2-yl, j=3, m=s=1, $R_5$=methyl, and $R_6$=hydrogen;

Compound of Formula I, wherein A=tBOC, G=OH, L=CF$_2$CH$_2$, X and Y taken together with the carbon atoms to which they are attached are phenyl, W is absent, Z=thiophen-2-yl, j=3, m=s=1, and $R_5$=$R_6$=hydrogen; and Compound of Formula I, wherein A=tBOC, G=OH, L=—CHFCH$_2$—, X and Y taken together with the carbon atoms to which they are attached are phenyl, W is absent, Z=thiophen-2-yl, j=3, m=s=1, and $R_5$=$R_6$=hydrogen.

7. A compound of Formula V:

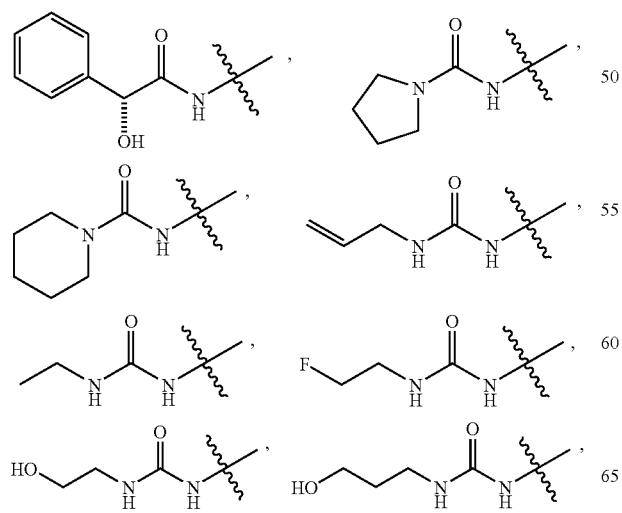

(V)

wherein A is selected from:

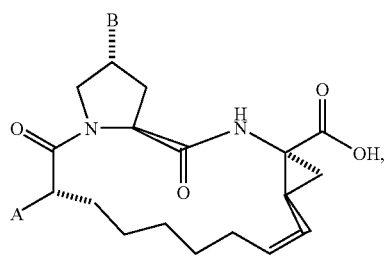

and B is selected from:

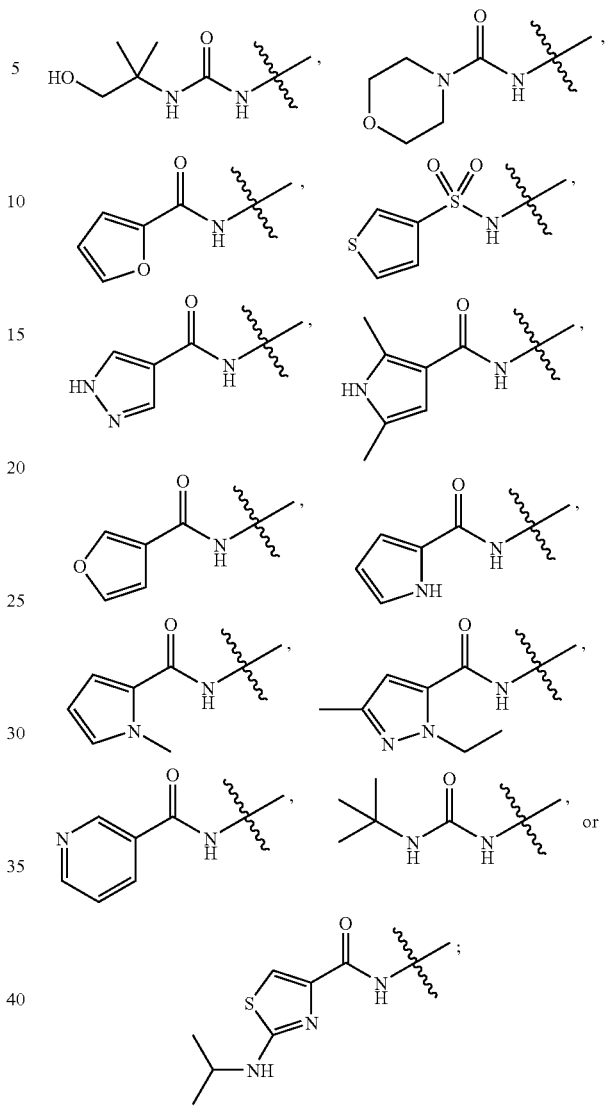

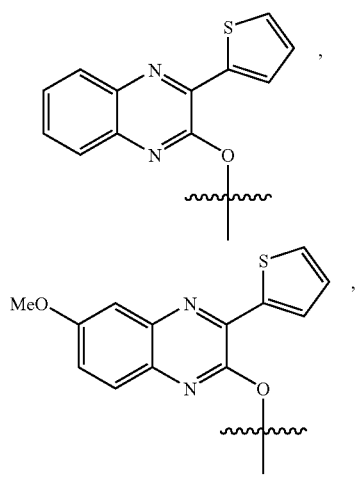

-continued
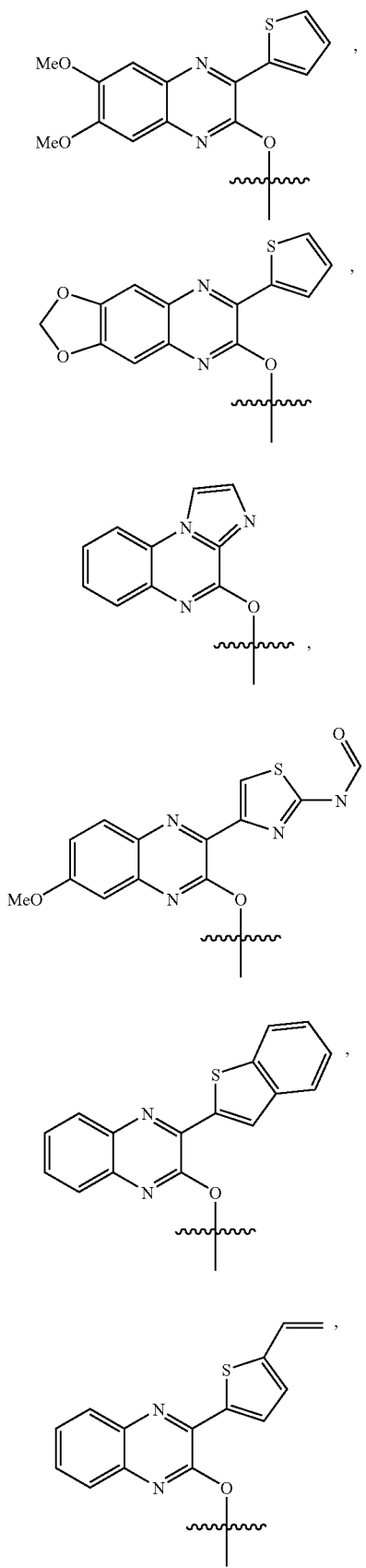
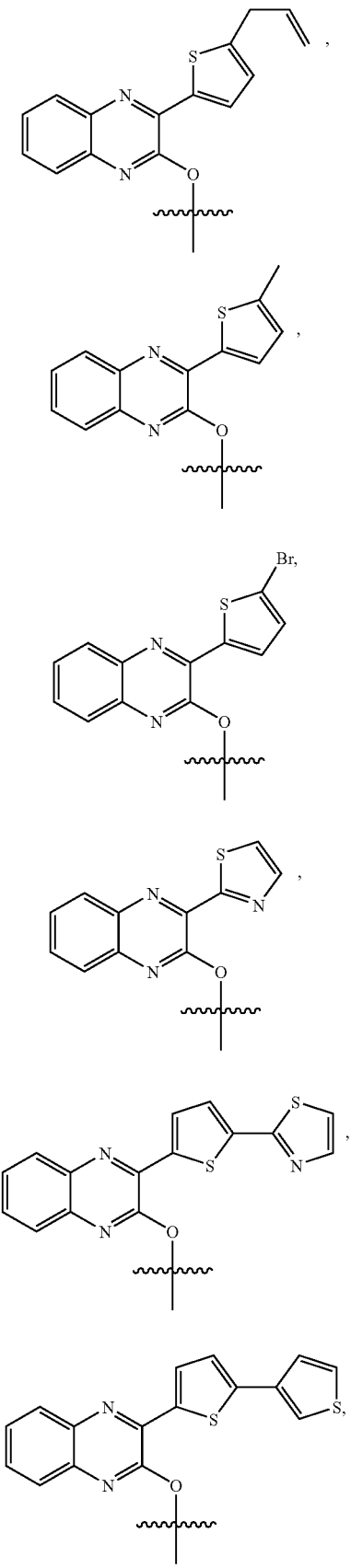

-continued
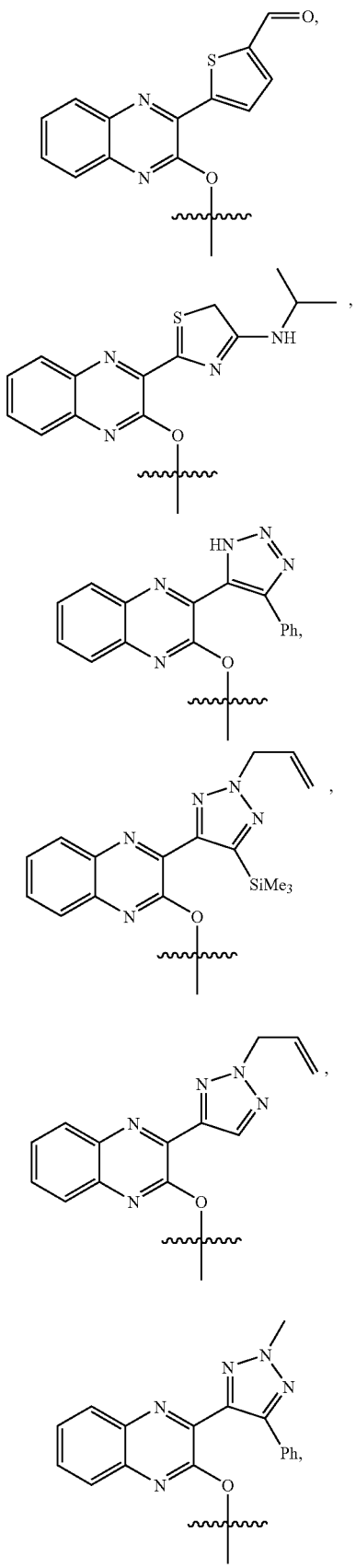
-continued
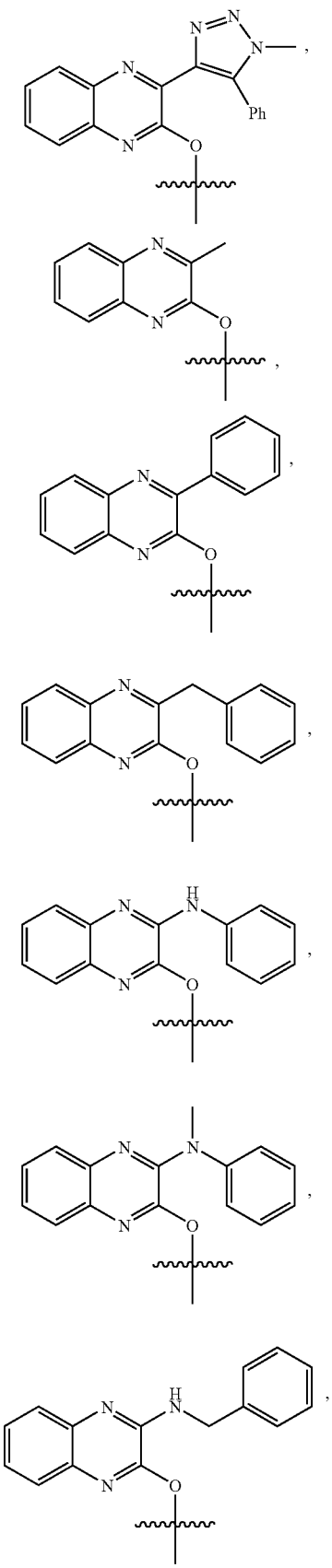

-continued
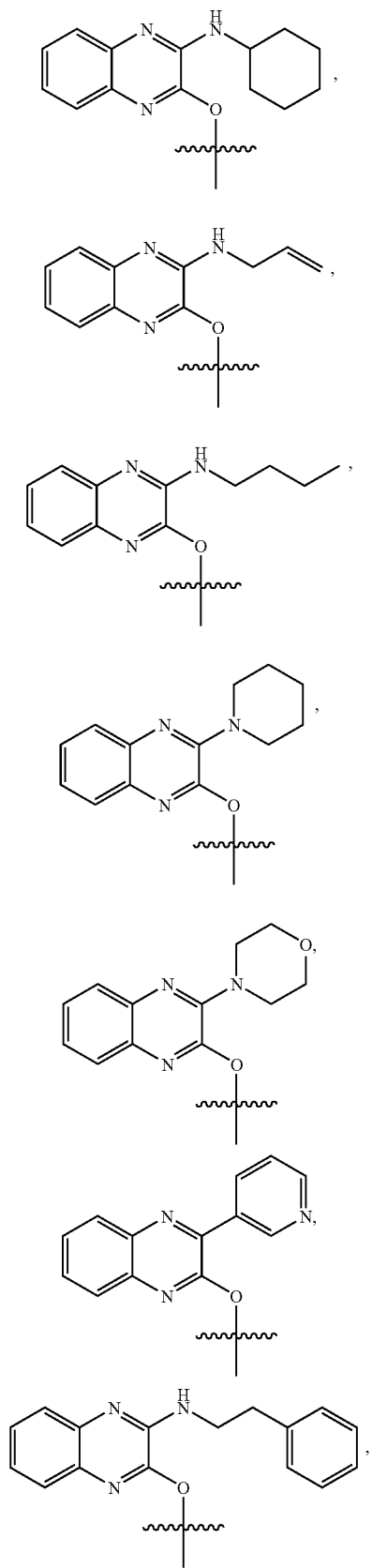
-continued
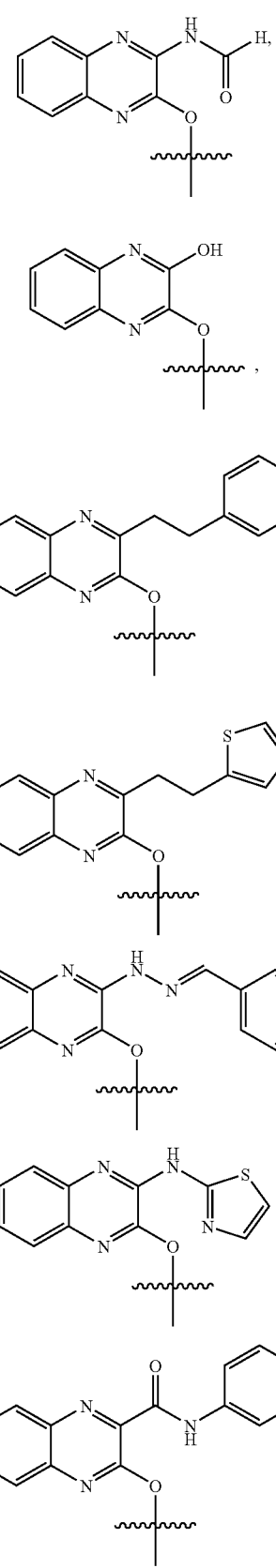

127
-continued
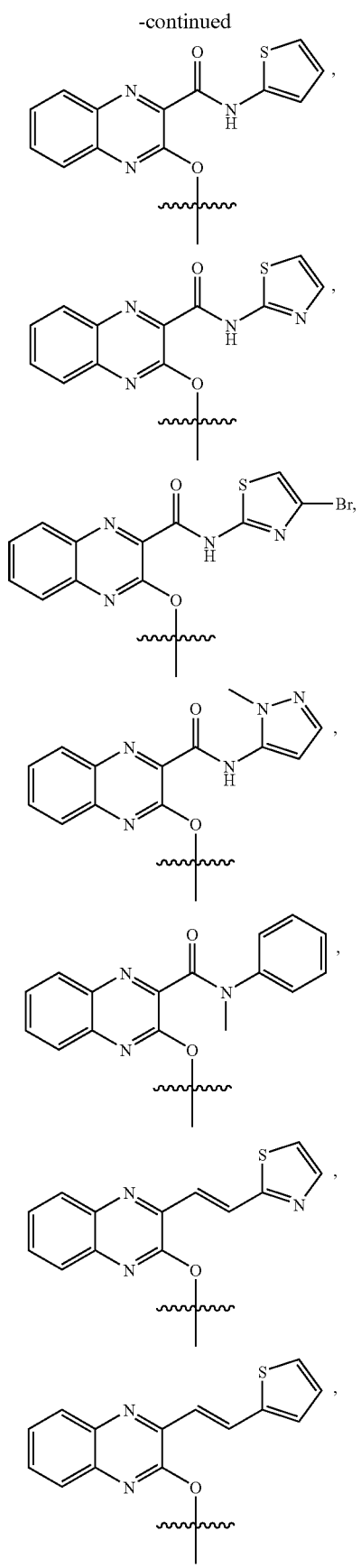
128
-continued
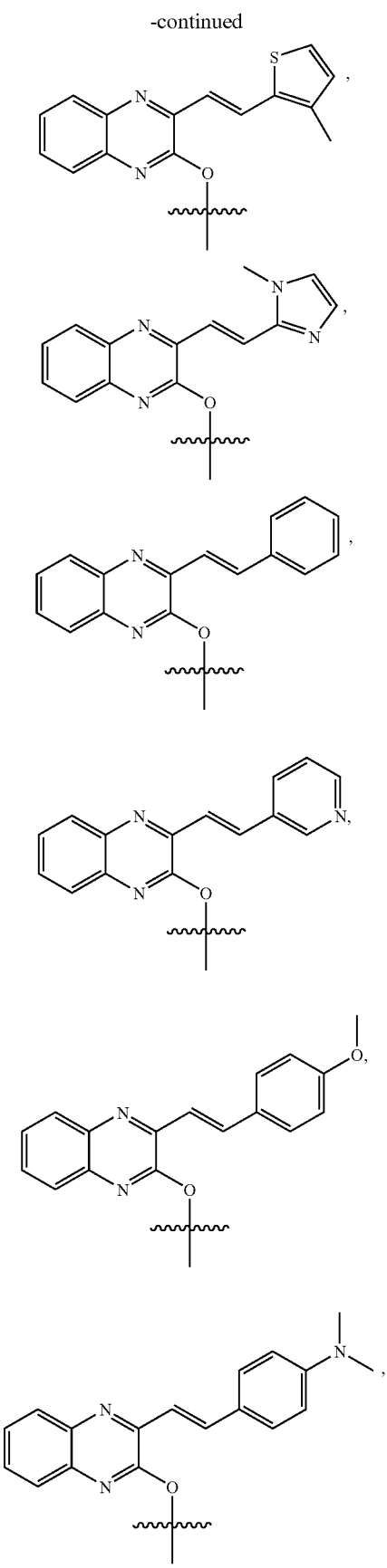

129
-continued
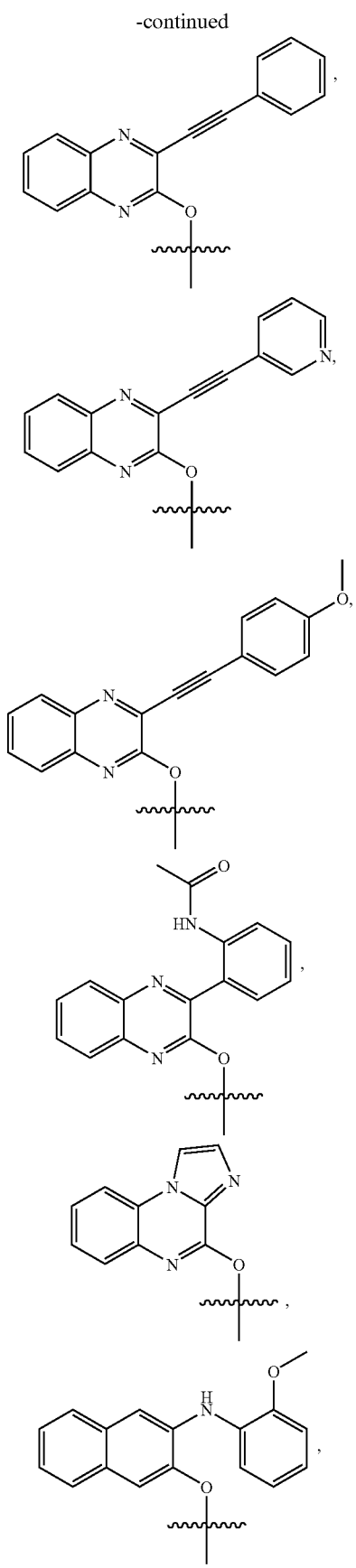
130
-continued
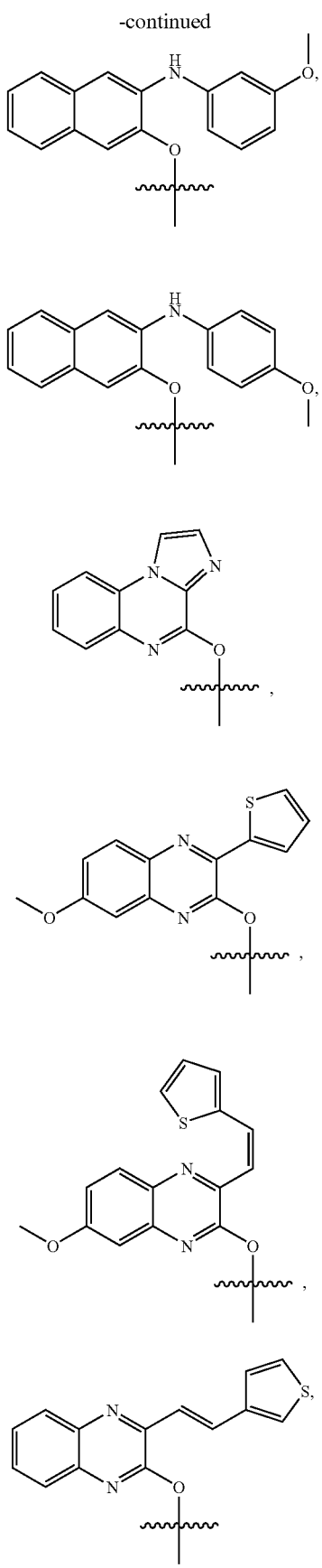

131
-continued
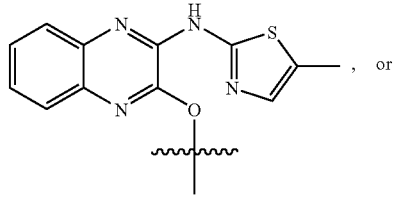
, or
132
-continued
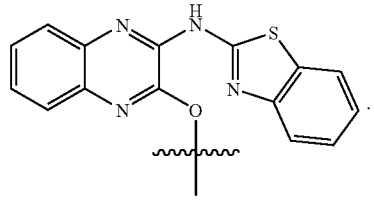
.
8. A compound of claim 7 selected from the following compounds:
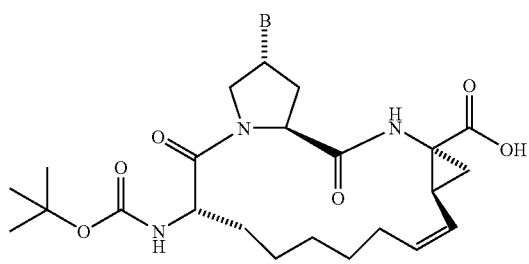
| Compound | B | Compound | B |
|---|---|---|---|
| 101301 | 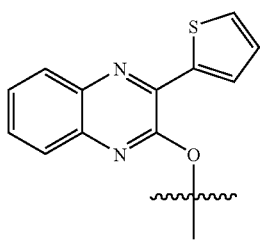 | 101358 | 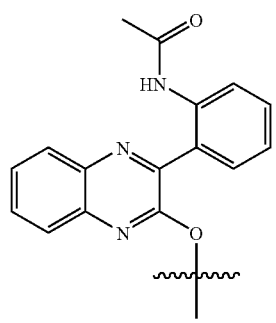 |
| 101306 | 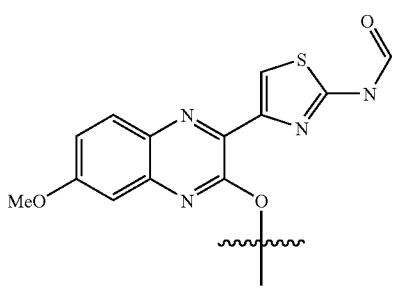 | 101302 | 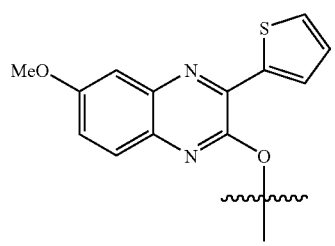 |
| 101322 | 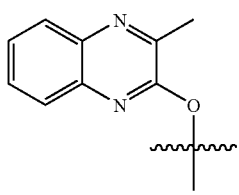 | 101311 | 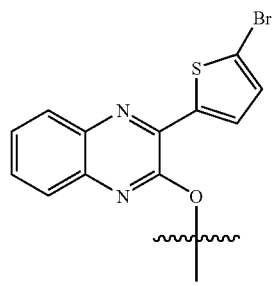 |

-continued
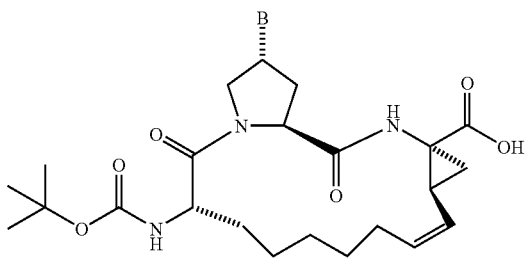
| Compound | B | Compound | B |
|---|---|---|---|
| 101325 | 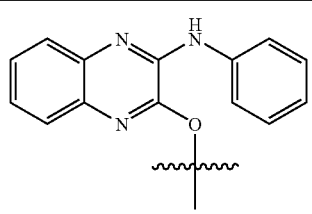 | 101303 | 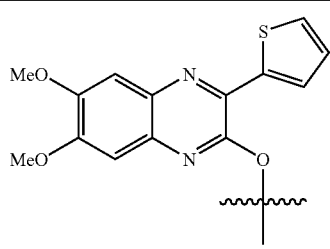 |
| 101326 | 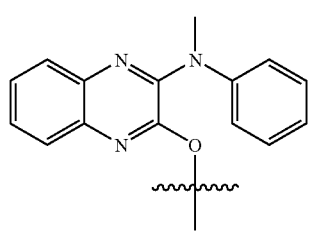 | 101327 | 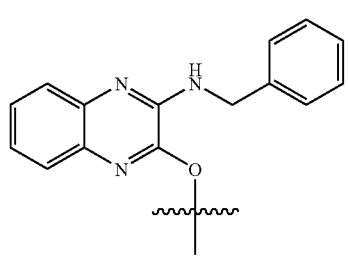 |
| 101330 | 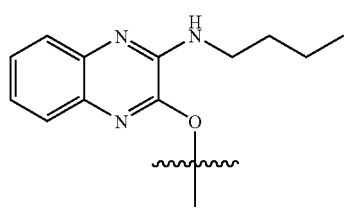 | 101331 | 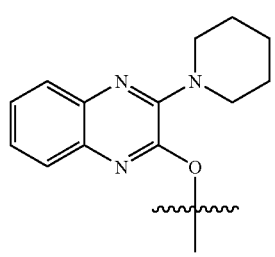 |
| 101332 | 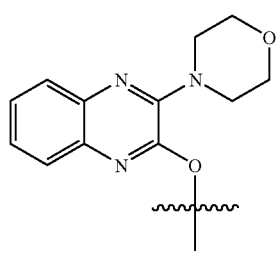 | 101335 | 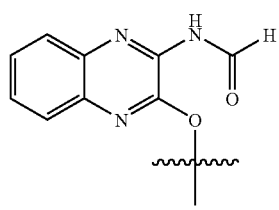 |
| 101336 | 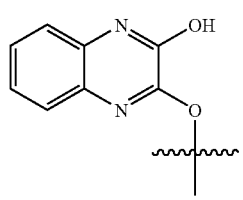 | 101348 | 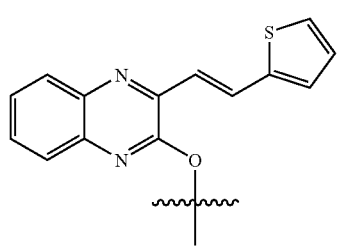 |

-continued
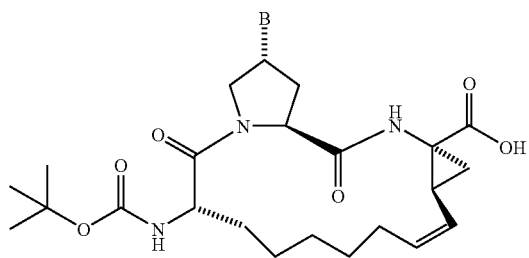
| Compound | B | Compound | B |
|---|---|---|---|
| 101340 | 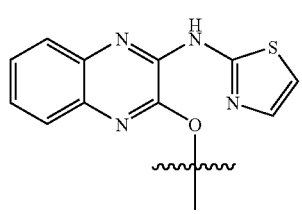 | 101334 | 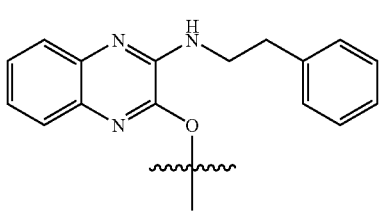 |
| 101348 | 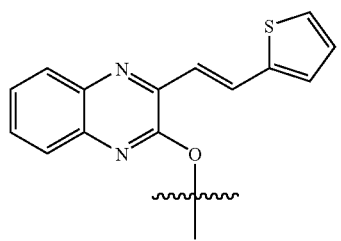 | 101359 | 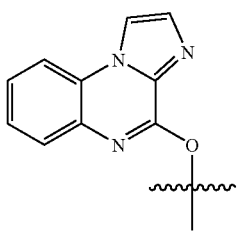 |
| 101328 | 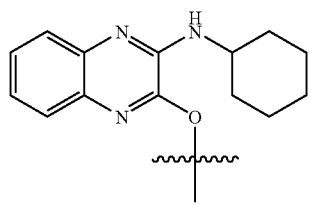 | 101360 | 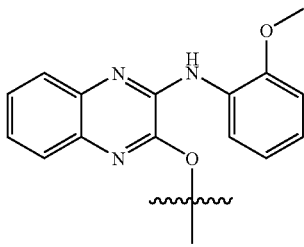 |
| 101361 | 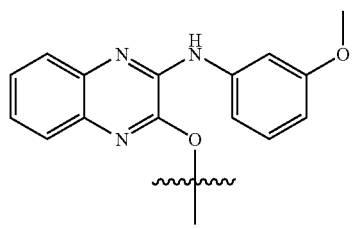 | 101362 | 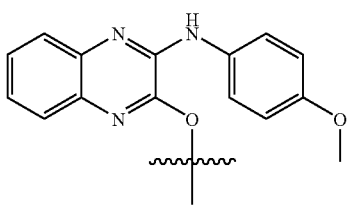 |
| 101329 | 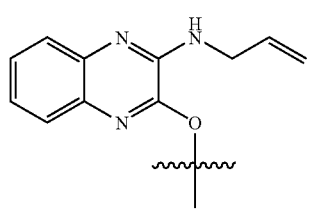 | 101324 | 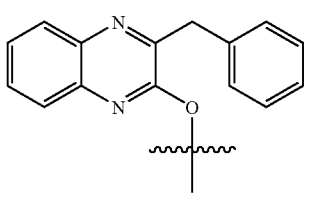 |

-continued
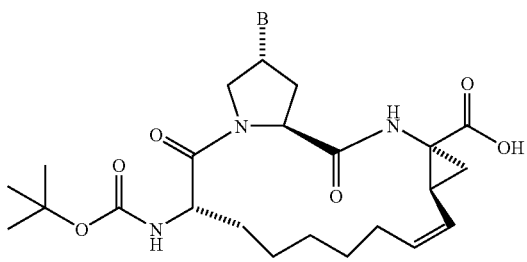
| Compound | B | Compound | B |
|---|---|---|---|
| 101304 | 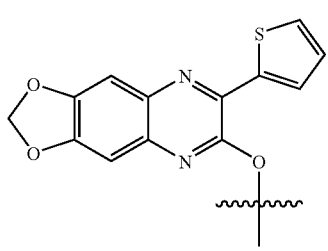 | 101355 | 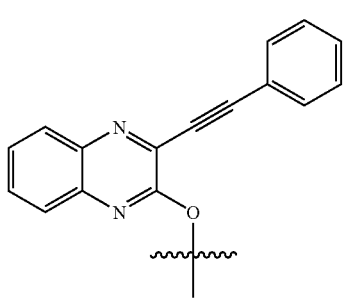 |
| 101356 | 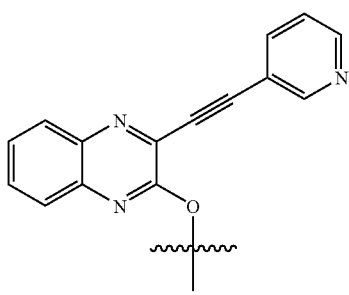 | 101307 | 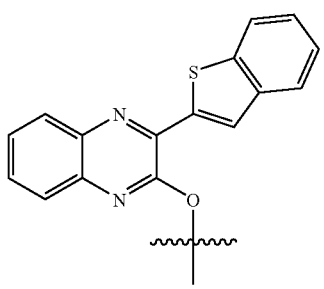 |
| 101357 | 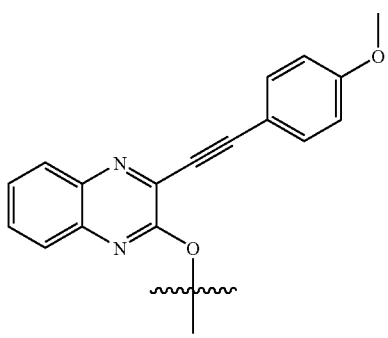 | 101347 | 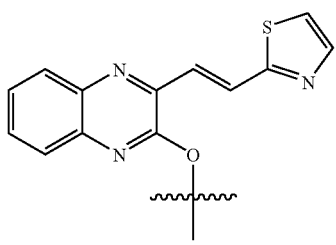 |
| 101352 | 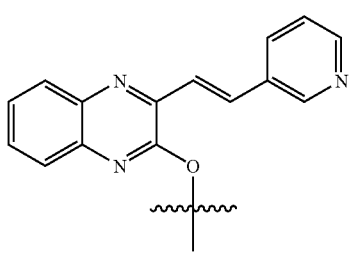 | 101364 | 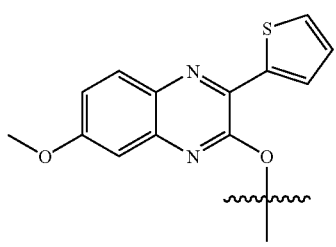 |

-continued
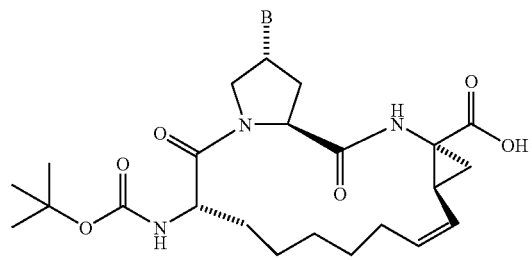
| Compound | B | Compound | B |
|---|---|---|---|
| 101308 | 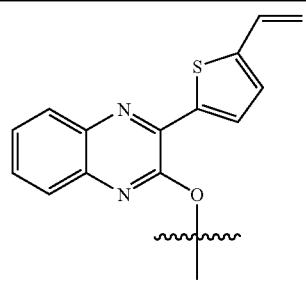 | 101309 | 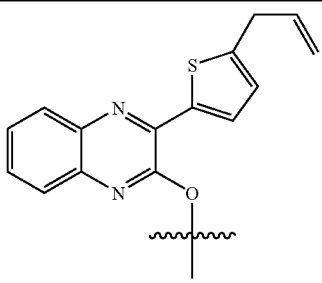 |
| 101367 | 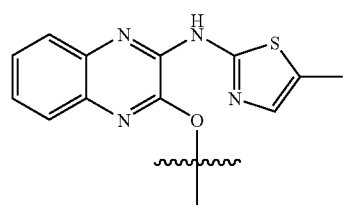 | 101368 | 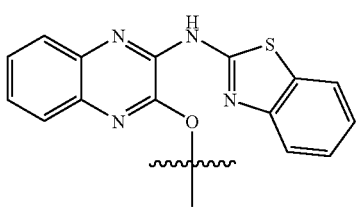 |
| 101323 | 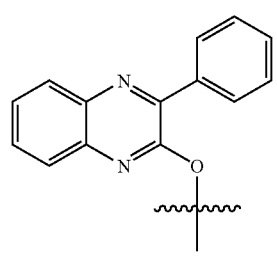 | 101317 | 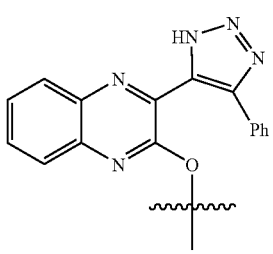 |
| 101318 | 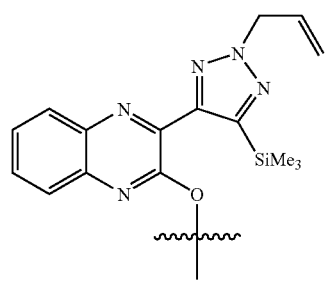 | 101319 | 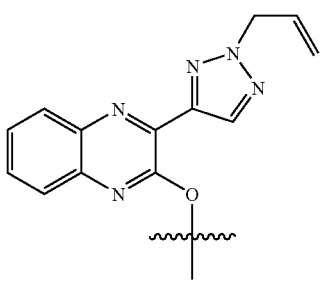 |
| 101351 | 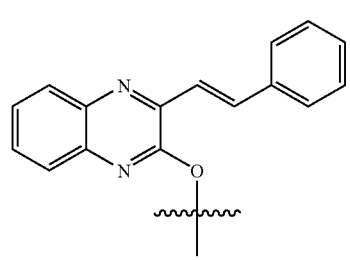 | 101353 | 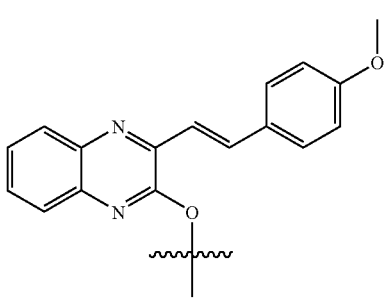 |

-continued
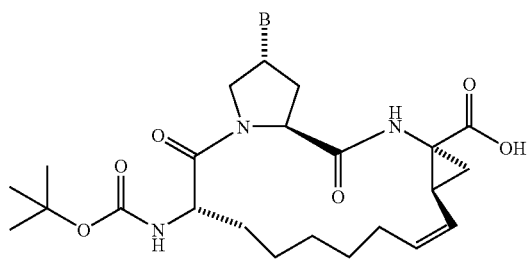
| Compound | B | Compound | B |
|---|---|---|---|
| 101349 | 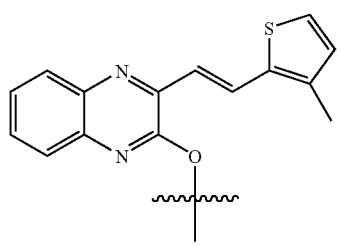 | 101333 | 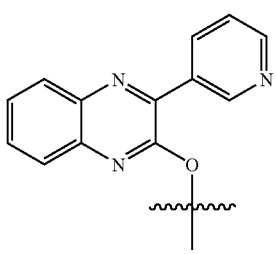 |
| 101320 | 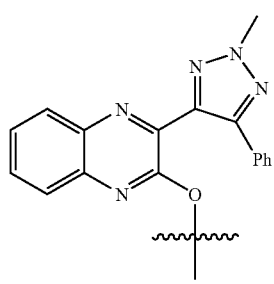 | 101321 | 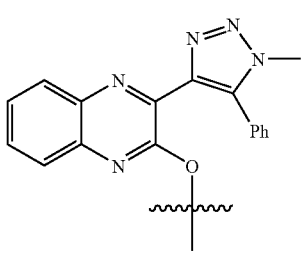 |
| 101347 | 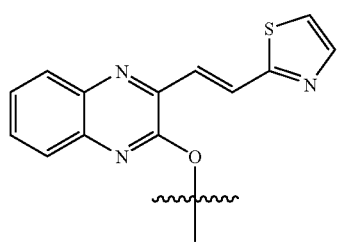 | 101350 | 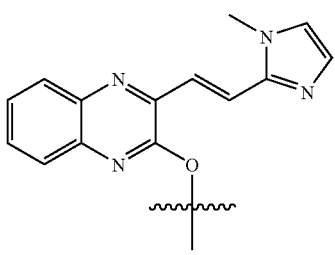 |
| 101313 | 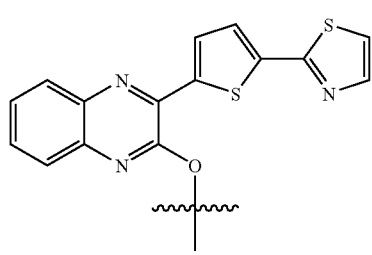 | 101366 | 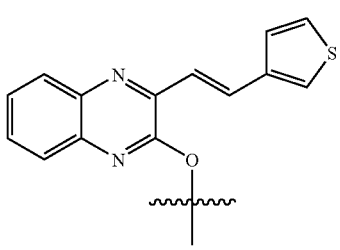 |

-continued
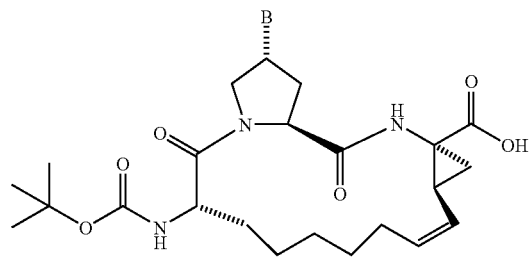
| Compound | B | Compound | B |
|---|---|---|---|
| 101354 | 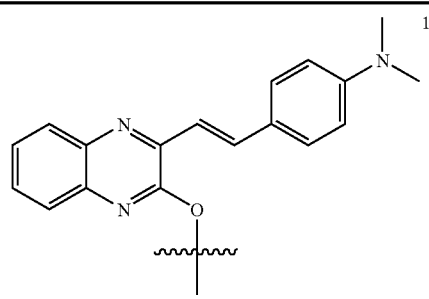 | 101343 | 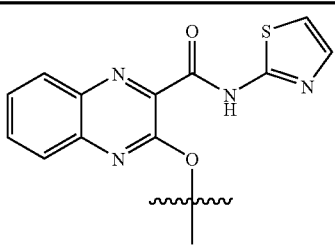 |
| 101314 | 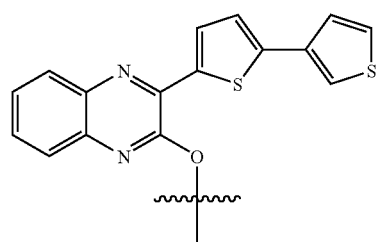 | 101339 | 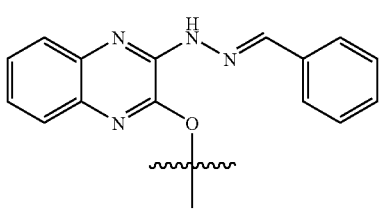 |
| 101341 | 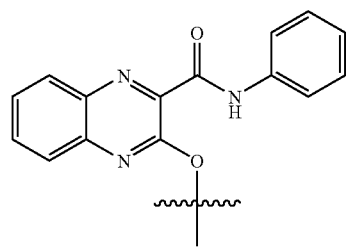 | 101345 | 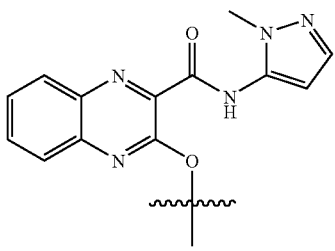 |
| 101344 | 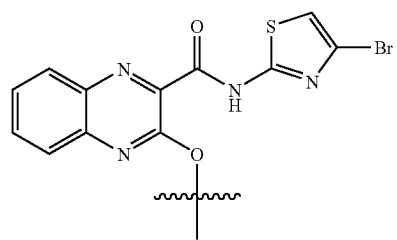 | 101342 | 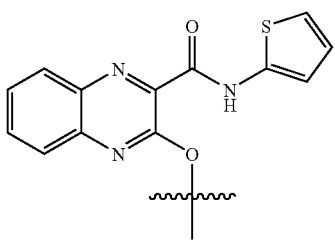 |
| 101315 | 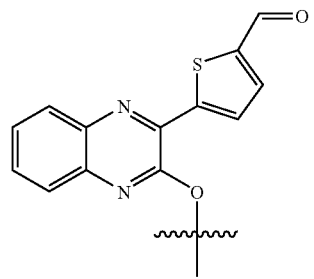 | 101346 | 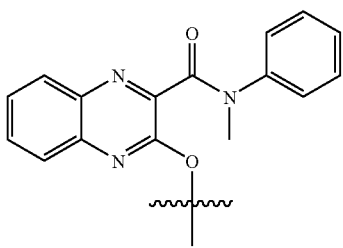 |

-continued
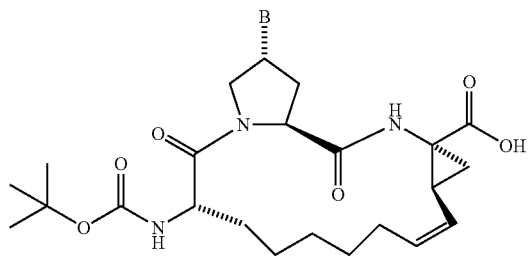
| Compound B | Compound B |
|---|---|
| 101337 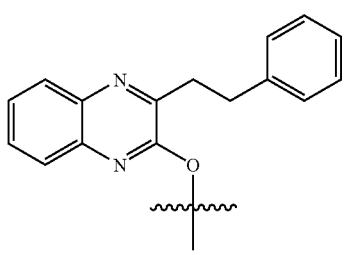 | 101338 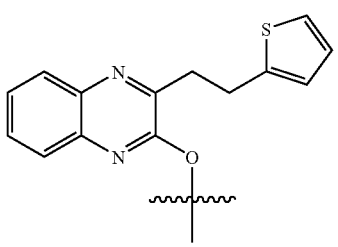 |
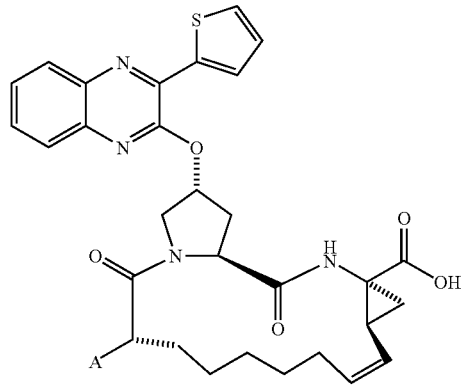
| Compound A | Compound A |
|---|---|
| 105301 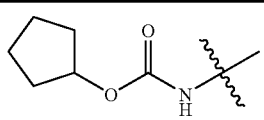 | 123301 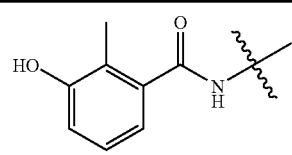 |
| 112301 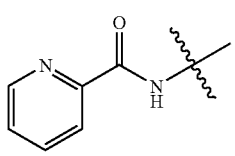 | 124301 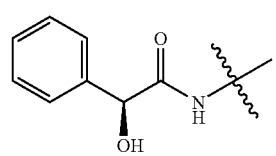 |
| 109301 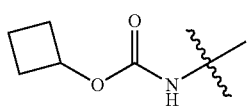 | 122301 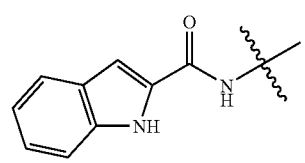 |

-continued
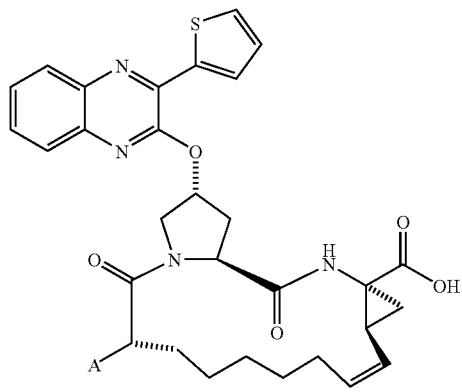
| Compound | A | Compound | A |
|---|---|---|---|
| 111301 | 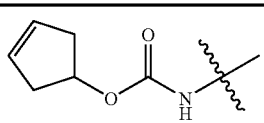 | 114301 | 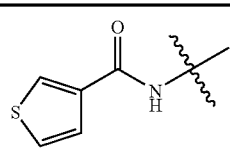 |
| 107301 | 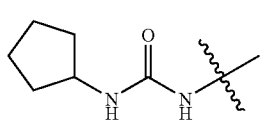 | 104301 | 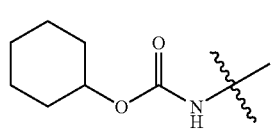 |
| 110301 | 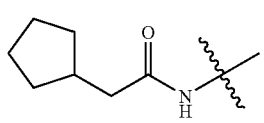 | 128301 | 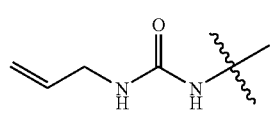 |
| 124301 | 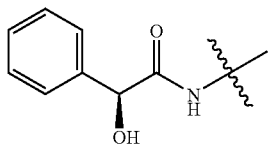 | 113301 | 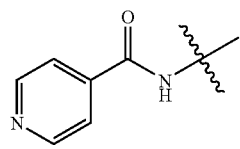 |
| 143301 | 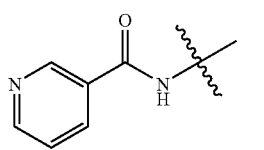 | 115301 | 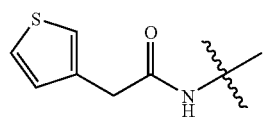 |
| 108301 | 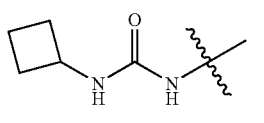 | 118301 | 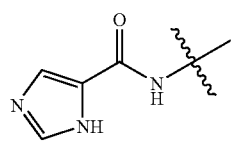 |
| 120301 | 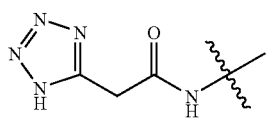 | 129301 | 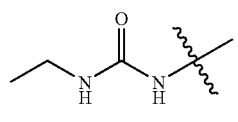 |
| 121301 | 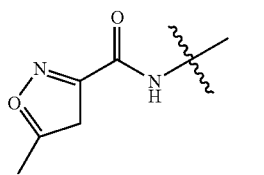 | 117301 | 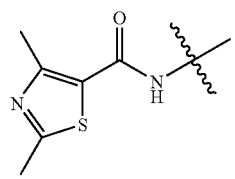 |

-continued
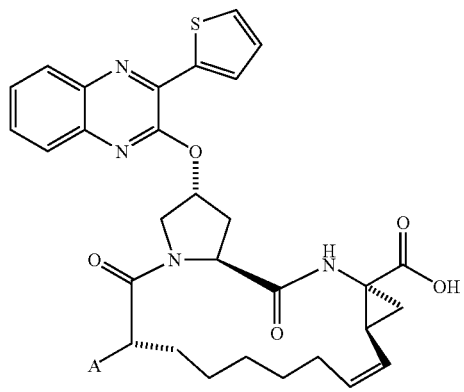
| Compound | A | Compound | A |
|---|---|---|---|
| 145301 | 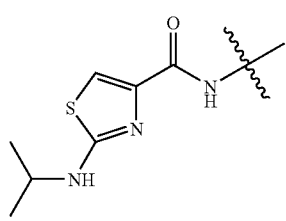 | 106301 | 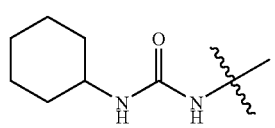 |
| 144301 | 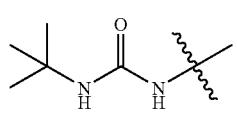 | 126301 | 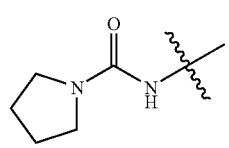 |
| 127301 | 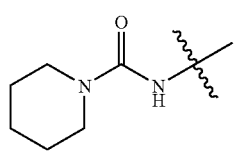 | 130301 | 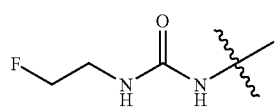 |
| 116301 | 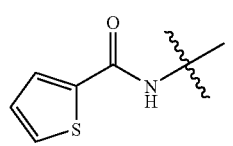 | 102301 | 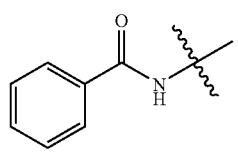 |
| 140301 | 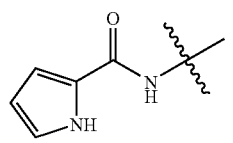 | 141301 | 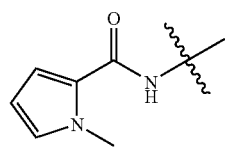 |
| 139301 | 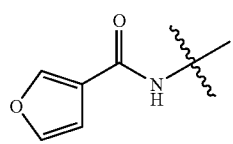 | 138301 | 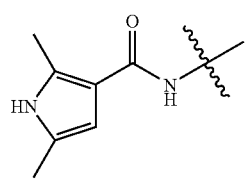 |

-continued
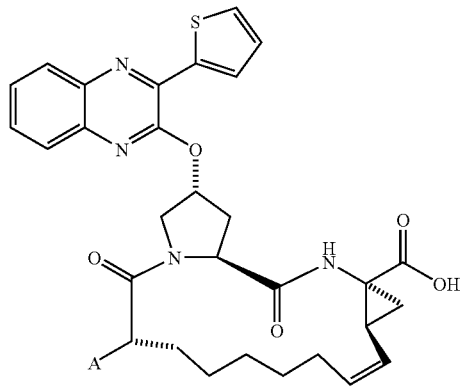
| Compound | A | Compound | A |
|---|---|---|---|
| 142301 | 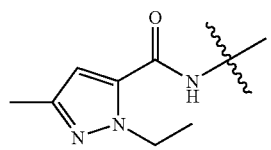 | 137301 | 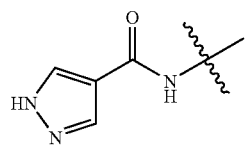 |
| 135301 | 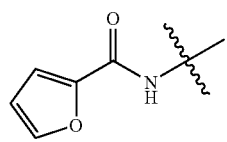 | 134301 | 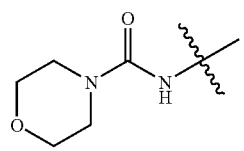 |
| 133301 | 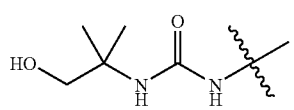 | 131301 | 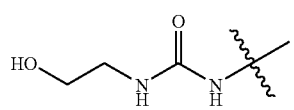 |
| 132301 | 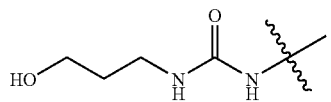 | 136301 | 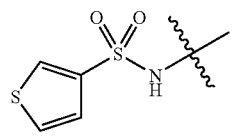 |
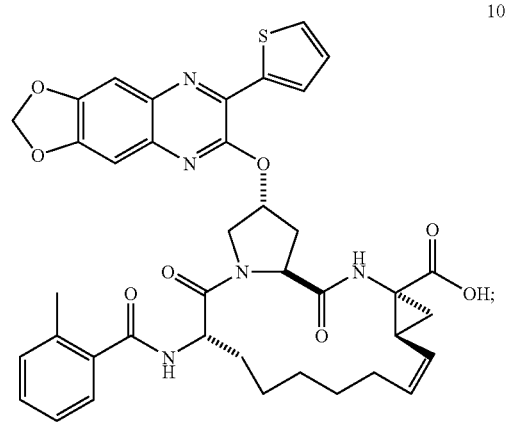
103304
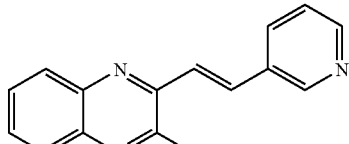
123352
-continued
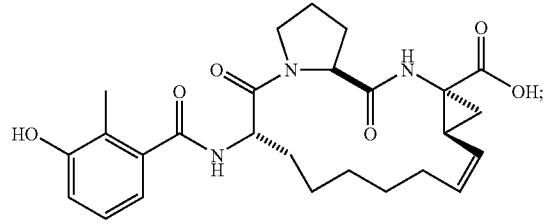

-continued

107365

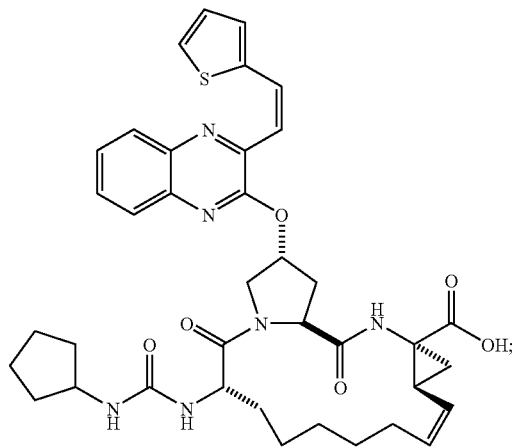

107341

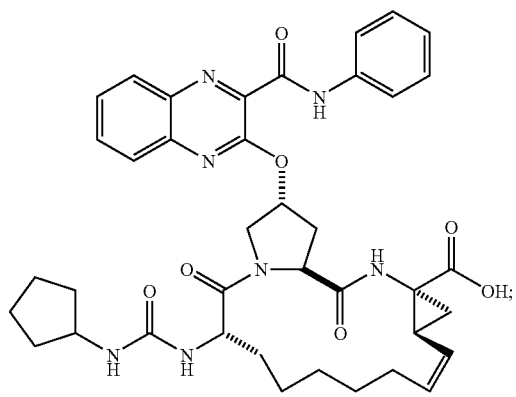
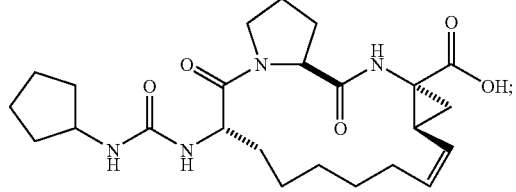

114341

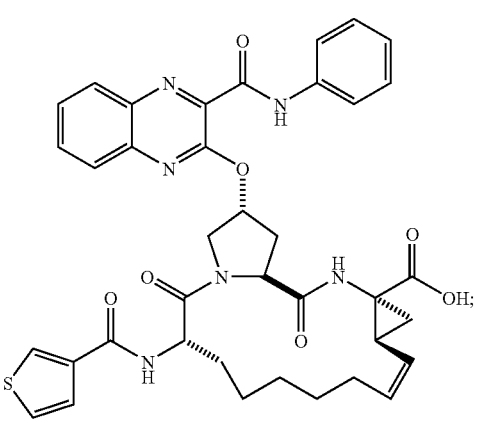

-continued

105316

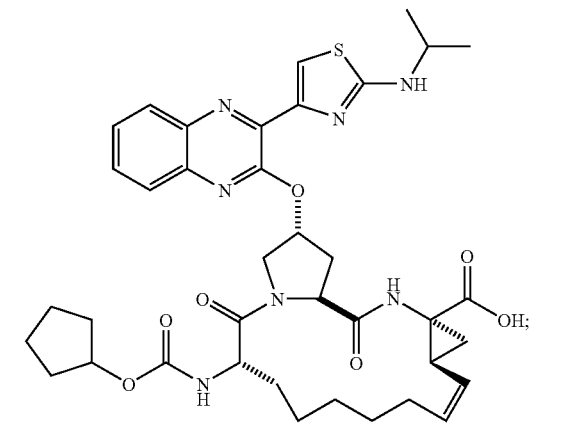

107316

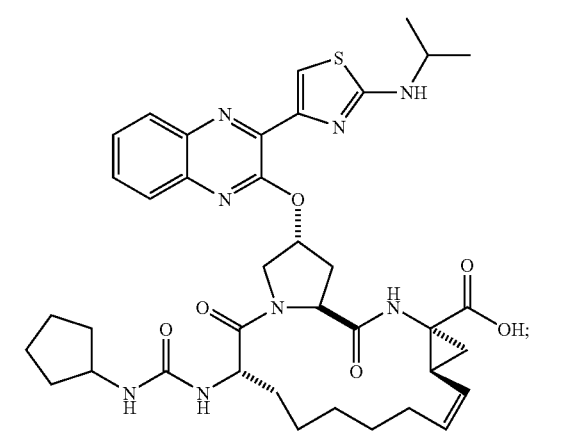

116365

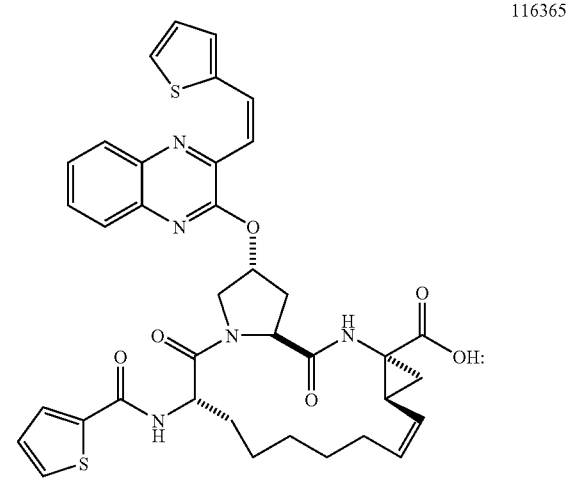

9. A pharmaceutical composition comprising an inhibitory amount of a compound according to claim 1 or 7 alone or in combination with a pharmaceutically acceptable carrier or excipient.

10. A method of treating a hepatitis C viral infection in a subject, comprising administering to the subject an inhibitory amount of a pharmaceutical composition according to claim 9.

* * * * *